United States Patent
Segarini et al.

(10) Patent No.: US 6,555,322 B1
(45) Date of Patent: Apr. 29, 2003

(54) α2-MACROGLOBULIN RECEPTOR AS A RECEPTOR FOR CTGF

(75) Inventors: Patricia R. Segarini, San Jose, CA (US); James E. Nesbitt, Menlo Park, CA (US); David F. Carmichael, Pacifica, CA (US)

(73) Assignee: FibroGen, Inc., South San Francisco, CA (US)

( * ) Notice: Subject to any disclaimer, the term of this patent is extended or adjusted under 35 U.S.C. 154(b) by 0 days.

(21) Appl. No.: 09/644,442

(22) Filed: Aug. 23, 2000

Related U.S. Application Data

(60) Provisional application No. 60/151,195, filed on Aug. 27, 1999.

(51) Int. Cl.$^7$ ............................................. G01N 33/53
(52) U.S. Cl. ...................... 435/7.1; 424/143.1; 436/501; 530/350; 435/69.1
(58) Field of Search ................ 435/7.1, 69.1; 424/143.1; 530/350; 436/501

(56) References Cited

U.S. PATENT DOCUMENTS

| | | | |
|---|---|---|---|
| 5,408,040 A | | 4/1995 | Grotendorst |
| 6,323,177 B1 | * | 11/2001 | Curran et al. .................. 514/8 |

FOREIGN PATENT DOCUMENTS

| | | |
|---|---|---|
| WO | WO 95/28955 | 11/1995 |
| WO | WO 96/38168 | 12/1996 |
| WO | WO 96/38172 | 12/1996 |
| WO | WO 97/04794 | 2/1997 |

OTHER PUBLICATIONS

T. Nishida et al. Demonstration of receptors specific for connective tissue growth factor on a human chondrocytic cell line (HCS–2/8). 1998. Biochem. Biophy. Res. Comm., 247:905–909.*
Babic, A.M. et al. (1999) Mol. Cell. Biol. 19:2958–2966.
Ball, D.K. et al. (1998) Biol. Reprod. 59:828–835.
Bradham, D. et al. (1991) J. Cell Biology 114:1285–1294.
Brigstock, D.R. et al. (1997) J. Biol. Chem. 272(32):20275–20282.
Bu, G. et al. (1998) J. Biol. Chem. 273:13359–13365.
Casslen, B. et al. (1998) Mol. Hum. Reprod. 4:585–593.
Gliemann, J. (1998) Biol. Chem. 379:951–964.
Gotthardt, M. et al. (2000) J. Biol. Chem., 275–25616–25624.
Handschug, K. et al., (1998) J. Mol. Med. 76:596–600.
Herz, J. et al. (1988) EMBO J. 7:4119–4127.
Herz, J. et al. (1992) Cell 71:411–421.
Herz, NCBI Entrez Database, Apr. 18, 1996, GenBank No. GI 34338 (Genbank Accession No. X13916).
Herz, NCBI Entrez Database, Apr. 18, 1996, GenBank No. GI34339 (Genbank Accession No. CAA32112).
Hussaini, I.M. et al. (1999) Antisense and Nucleic Acid Drug Development, 9:183–190.
Jedsadayanmata, A. et al. (1999) J. Biol. Chem. 274:24321–24327.
Kristensen, T. et al. (1990) FEBS Lett. 276:151–155.
Kounnas, M.Z. et al. (1996) J. Biol. Chem. 27:6523–6529.
Mikhailenko, I. et al. (1995) J. Biol. Chem. 270:9543–9549.
Mikhailenko, I. et al. (1997) J. Biol. Chem. 272:6784–6791.
Neels, J. (1998) Fibrinolysis and Proteolysis, 12:219–240.
Nishida, T. et al. (1998) Biochem. Biophys. Res. Comm. 247:905–909.
Nishida, T. et al. (2000) J. Cell. Physiol. 184:197–206.
Pinson, K.I. et al. (2000) Nature 407:535–538.
Strickland, D.K. et al. (1990) J. Biol. Chem. 265:17401–17404.
Tamai, K. et al. (2000) Nature 407:530–535.
Trommsdorff, M. et al. (1998). J. Biol. Chem. 273:33556–33560.
Ulery, P.G. et al. (2000) J. Biol. Chem. 275:7410–7415.
Warshawsky, I. et al. (1993) J. Biol. Chem. 268:22046–22054.
Warshawsky, I. et al. (1993) J. Clin. Invest. 92:937–944.
Wehrli, M. et al. (2000) Nature 407:527–530.
Willnow, T. E. and J. Herz (1994) J. Cell. Sci. 107:719–726.

* cited by examiner

*Primary Examiner*—Lorraine Spector
*Assistant Examiner*—Dong Jiang
(74) *Attorney, Agent, or Firm*—FibroGen, Inc.

(57) ABSTRACT

The invention provides a connective tissue growth factor (CTGF) receptor and biochemical and/or biological equivalents, homologs, derivatives, subunits, fragments, and complexes thereof. The CTGF receptor is useful in the treatment and diagnosis of CTGF-associated disorders and in methods of screening for agents that effect CTGF receptor expression and activity. The invention further provides nucleic acid sequences encoding the CTGF receptor, recombinant DNA molecules comprising these sequences, and transformed hosts carrying the recombinant DNA molecules, antisense sequences and antibodies directed against CTGF receptor, and pharmaceutical compositions for use in treatment of CTGF-associated disorders.

7 Claims, 32 Drawing Sheets

A.   B.

α2-MACROGLOBULIN RECEPTOR AS A RECEPTOR FOR CTGF

RELATED APPLICATIONS

This application claims the benefit of prior application U.S. Provisional Application Serial No. 60/151,195, filed Aug. 27, 1999, the specification of which is incorporated herein by reference in its entirety.

FIELD OF THE INVENTION

This invention relates generally to connective tissue growth factor (CTGF) and to receptors thereof.

BACKGROUND OF THE INVENTION

Growth factors are a class of secreted polypeptides that stimulate target cells to proliferate, differentiate, and organize developing tissues. Typically, a growth factor's activity is dependent on its ability to bind to specific receptors, thereby stimulating a signaling event within the cell. Examples of some well-studied growth factors include platelet-derived growth factor (PDGF), insulin-like growth factor (IGF-I), transforming growth factor beta (TGF-β), transforming growth factor alpha (TGF-α), epidermal growth factor (EGF), and fibroblast growth factor (FGF). Efforts to characterize the receptors corresponding to these growth factors are ongoing and have met with varying degrees of success.

Low Density Lipoprotein Receptor-Related Protein (LRP)

A low density lipoprotein receptor-related protein (LRP) has been reported previously in the literature. (See, e.g., Kristensen et al., 1990, *FEBS Lett.* 276:151–155.) This protein is also known as the α2-macroglobulin receptor. (See, e.g., Strickland, D. K. et al. (1990) *J. Biol. Chem.* 265:17401–17404; and Herz et al. (1988) *EMBO J.* 7:4119–4127.) LRP is encoded by a protein sequence of about 4544 amino acids in length (human mRNA for LDL-receptor related protein, GenBank Accession No. X13916; human LDL-receptor related precursor protein, GenBank Accession No. CAA32112; Herz et al., id; Myklebost et al. (1989) *Genomics*, 5:65–69, each of which references is incorporated by reference herein in its entirety.) The mature protein consists of a 4419 amino acid ectodomain, a twenty-five amino acid transmembrane domain and a 100 amino acid intracellular domain. As reported in the literature, the ectodomain contains a furin cleavage site which is processed during transport from a late Golgi compartment, producing a 510 kDa α subunit that is noncovalently associated with an 85 kDa β subunit anchored to the membrane through the transmembrane sequence. (See, e.g., Strickland, D. K. et al., supra.)

The α2-macroglobulin receptor has been widely studied and a number of subdomains have been identified within the α and β subunits. These subdomains include twenty-two EGF-like domains, of which two such domains are $Ca^{2+}$ binding, eight are EGF precursor spacer regions, and thirty-one are LDL receptor ligand-binding repeats. Additionally, thirty-one copies of complement-type repeats arranged in four clusters spanning the receptor sequence have been identified. It has been reported that the receptor protein sequence is highly conserved (more than 97% homology) between the human and murine systems. (See, e.g., Van Leuven et al. (1993) *Biochim. Biophys. Acta.*, 1173:71–74.)

The cytoplasmic domain of the α2-macroglobulin receptor has no homology with known protein kinase domains. Genetic analysis of the protein function by disruption of the α2-macroglobulin receptor gene in order to create α2-macroglobulin receptor-deficient mice has indicated that the protein is essential during development. A number of ligands have been reported to bind to the α2-macroglobulin receptor, including α2 macroglobulin, activated; apolipoprotein E (apo E); low density lipoprotein, apo E enriched; Pseudomonas exotoxin A; receptor-associated protein (RAP); plasminogen activator inhibitor (PAI) I; thrombin-PAI complex; tissue plasminogen activator (tPA); urokinase plasminogen activator (uPA); thrombospondin I; lipoprotein lipase; hepatic lipase; lactoferrin; pregnancy zone protein; α1-inhibitor-3; α1-inhibitor-3/α1 microglobulin complex; β amyeloid precursor protein; suramin; and vitellogenin. The adaptor molecule mDab1 has been shown to bind to the cytoplasmic tail of LRP in neuronal cells. (See, e.g., Le, N., and M. A. Simon (1998) *Mol. Cell. Bio.* 18:4844–54; and Trommsdorff, M. et al. (1998) *J. Biol. Chem.* 273:33556–60.) When tyrosine-phosphorylated, mDab1 binds non-receptor tyrosine kinases, such as src, fyn, and abl. (See, e.g., Howell, B. W. et al. (1997) *Embo Journal.* 16:121–32.) Another member of this family, Dab2, is expressed more widely, and has recently been shown to bind Grb2, an adaptor protein which couples tyrosine kinase receptors to Sos which is part of Ras signaling cascade. (See, e.,g., Xu, X.X. et al. (1998) *Oncogene.* 16:1561–9; and Fazili, Z. et al. (1999) *Oncogene.* 18:3104–13.) Recent findings indicate broad physiological functions for LRP and other members of the LDL receptor family, suggesting that interfering with any associated signaling cascade would provide methods of modulating activities associated with LRP. (Gotthardt et al. (2000) *J. Biol. Chem.*, 275:25616–25624.)

Connective Tissue Growth Factor (CTGF)

Connective tissue growth factor (CTGF) has been reported and described previously. (See, e.g., U.S. Pat. No. 5,408,040; Bradham et al., 1991, *J. Cell Biology* 114:1285–1294.) CTGF is characterized as a polypeptide that exists as a monomer with a molecular weight of approximately 36 to 38 kD. CTGF has been shown to be one of seven cysteine-rich secreted proteins belonging to the CCN family, which includes CTGF, cyr-61, and nov. (See, e.g., Oemar et al. (1997) *Arteriosclerosis, Thrombosis and Vascular Biology* 17(8):1483–1489.) CTGF is the product of an immediate early response gene that codes for a protein consisting of four modules and one signal peptide. (See, e.g., Oemar et al. (1997), supra.) The four modules include an insulin-like growth factor (IGF) binding domain, a von Willebrand factor type C repeat most likely involved in oligomerization, a thrombospondin type 1 repeat believed to be involved in binding to the ECM, and a C-terminal module which may be involved in receptor binding. Recent reports suggest that certain fragments of the whole CTGF protein possess CTGF activity. (See, e.g., Brigstock et al. (1997) *J. Bio. Chem.* 272(32):20275–282; International Publication No. WO 00/047114; and International Publication No. WO 00/047130, each of which references is incorporated herein by reference in its entirety.) Human, mouse, and rat CTGF are highly conserved, with greater than 90% amino acid homology (Bork (1993) *FEBS Lett.* 327:125–130), and a molecular weight of about 38 kDa (Bradham et al. (1991) *J Cell Biol.* 114:1285–1294). It was recently shown that the promoter of the CTGF gene contains a novel TGF-β responsive element. (Grotendorst et al. (1996) *Cell Growth & Differentiation* 7:469–480.)

CTGF plays a role in the production of collagen and other extracellular matrix proteins. CTGF has mitogenic and chemotactic activity, and its effects have been observed in connective tissue cells, e.g., fibroblasts, as well as in a number of other cell types. The ability of CTGF to effect cell proliferation and motility have led to its implication in a variety of disorders associated with excess growth and increased deposition of extracellular matrix, including disorders such as fibrosis, cancer, angiogenesis, and other proliferative disorders. For example, CTGF appears to be a causal factor in skin fibrosis and in atherosclerosis. (See, e.g., Igarashi et al. (1995) *The Journal of Investigative Dermatology* 105:280–284; Igarashi et al. (1996) *The Journal of Investigative Dermatology* 106:729–733; Oemar et al. (1997) *Circulation* 95:831–839).

CTGF is therefore an attractive target for the development of therapeutic agents useful in the treatment of a number of connective tissue diseases and proliferative disorders. The desirability of modulating, and, preferably, inhibiting, CTGF activity as a method for treating fibrotic diseases and disorders has been previously described. (See, e.g., PCT Application No. PCT/US96/08140.) Various inhibitors of CTGF activity, including peptides, antibodies to CTGF, and the like, have been described and are reported to have potential therapeutic effectiveness in the treatment of fibrotic disease. (Id.) It has also been determined that CTGF is capable of inducing bone and cartilage growth and tissue repair, such as wound healing. (See, e.g., U.S. Pat. No. 5,408,040 and PCT Application No. PCT/US96/08210.) Biological activities attributed to CTGF include stimulating fibroblast proliferation (Kothapalli et al. (1 997) *Cell Growth Differ.* 8:61–68; Frazier et al. (1996) *J. Invest. Dermatol.* 107:404–411; Kothapalli et al. (1998) *FASEB J.* 12:1151–1161; Kothapalli and Grotendorst (2000) *J. Cell. Physiol.* 182:119–126), cell adhesion, migration, angiogenesis (Babic et al. (1999) *Mol. Cell. Biol.* 19:2958–2966; Shimo et al. (1999) *J. Biochemistry (Tokyo)* 126:137–145), stimulating the expression of extracellular matrix components, such as collagen, fibronectin, and $_5$-integrin (Frazier et al. (1996) *J. Invest. Dermatol.* 107:404–411), and in some cells, apoptosis (Hishikawa et al. (1999) *Eur. J. Pharmacol.* 385:287–290; Hishikawa et al. (1999) *J. Biol. Chem.* 274:37461–37466). High expression of CTGF has also been associated with wound healing and granulation tissue formation (Frazier et al. (1996) *J. Invest. Dermatol.* 107:404–411; Moir et al. (1999) *J. Cell. Physiol.* 181:153–159). In embryonic development, CTGF has been observed specifically at sites of endochondral ossification (Nakonnishi and Takigawa (1999) *Seikagaku* 74:429–432), and embryo implantation within the uterus (Surveyor et al. (1998) *Biol. Reprod.* 59:1207–1213; Surveyor and Brigstock (1999) *Growth Factors* 17:115–124). CTGF mRNA and protein over-expression have been localized to affected tissues in disease states, including scleroderma and keloid fibroblasts (Igarishi et al. (1996) *J. Invest. Dermatol.* 106:729–733), mesangial cells within renal fibrosis (Riser et al. (2000) *J. Am. Soc. Nephrol.* 11:25–38), pancreatitis (di Mola et al. (1999) *Ann. Surg.* 230:63–71), bleomycin-induced pulmonary fibrosis (Lasky et al. (1998) *Am. J. Physiol.* 275:L365–371), systemic sclerosis (Igarashi et al. (1995) *Invest. Dermatol.* 105:280–284; Sato et al. (2000) *J. Rheumatol.* 27:149–154), fibrous stroma of mammary tumors (Frazier and Grotendorst (1997) *Int. J. Biochem. Cell. Biol.*, 29:153–161), advanced atherosclerotic lesions (Oemar et al. (1997) *Circulation* 95:831–839), the infarct zone of myocardial infarction (Ohnishi et al. (1998) *J. Mol. Cell. Cardiol.* 30:2411–2422), inflammatory bowel disease (Darnmeier et al. (1998) *Int. J. Biochem. Cell. Biol.* 30:909–922), and desmoplastic malignant melanoma (Kubo et al. (1998) *Br. J. Dermatol,* 139:192–197. The over-expression of CTGF in tissue has been highly correlated with the onset and extent of renal and liver fibrosis (Ito et al. (1998) *Kidney Int.* 53:853–861; Paradis et al. (1999) *Hepatology* 30:968–976. Therefore, understanding the role of CTGF within these disease states, therefore, is of great importance.

Substantial efforts have been directed to the isolation, characterization, and use of CTGF as a target in treating a variety of disorders. The potential benefits of the ability to modulate CTGF expression and activity, either to inhibit the overproduction of connective tissue and extracellular matrix, such as when treating fibrotic and other proliferative disorders, or to induce bone, tissue, and cartilage repair, when increased CTGF expression and activity would be desired, are evident. However, despite ongoing efforts, there has been no report of the identification, characterization, or isolation of receptors to CTGF. Likewise, means of modulating the activity of such receptors in order to achieve specific therapeutic effects, such as by administration of antibodies or other agents capable of effecting CTGF receptor activity, have not been reported in the literature.

In summary, CTGF plays a significant role in the normal development, growth, and repair of human tissue. The ability to enhance, inhibit, or otherwise modulate the activity or expression of CTGF could therefore be a valuable therapeutic tool. Affecting the ability of CTGF to bind to its receptor could be a useful means of modulating CTGF activity or expression. Therefore, there is a need for identification of a CTGF receptor and for means of modulating CTGF receptor activity.

The present invention is based on the discovery that CTGF binds to a particular protein, the low density lipoprotein receptor-related protein (LRP), also known as the α2-macroglobulin receptor, and the identification of LRP as a CTGF receptor. There has been no previous report that CTGF or fragments thereof bind to LRP. This discovery satisfies a need in the art as the receptor may be used to modulate and to identify other agents that modulate CTGF activity, and can provide a basis for the development of new therapeutic tools and methods for treatment of CTGF-associated disorders.

SUMMARY OF THE INVENTION

The present invention relates to the identification of a CTGF receptor and to methods of diagnosis, treatment, and screening.

In one aspect, the present invention provides a method of treating or preventing a CTGF-associated disorder, the method comprising administering to a subject in need an effective amount of an agent that effects the expression or activity of a CTGF receptor or fragments or subunits thereof. In a further embodiment, the method of treatment or prevention comprises administering to a subject in need an effective amount of an agent that inhibits the activity or expression of a CTGF receptor or fragments or subunits thereof. The agent can be, for example, an antibody that specifically binds to a CTGF receptor or fragments or subunits thereof, an antisense oligonucleotide having a sequence that binds to a sequence encoding a CTGF receptor or fragments or subunits thereof, or a small molecule. The present methods can be directed to the treatment of various disorders, including, for example, proliferative disorders, fibrotic disorders, sclerotic disorders, cancer, and angiogenesis.

In some methods according to the present invention, it can be desirable to increase the expression and activity of CTGF. Therefore, in one aspect, the present invention provides a method of treating or preventing a CTGF-associated disorder associated with decreased expression or activity of CTGF, the method comprising administering to a subject in need an effective amount of an agent that increases the activity or expression of a CTGF receptor or fragments or subunits thereof. In one embodiment, the agent is a CTGF receptor or fragments or subunits thereof.

The present invention further provides a method for identifying an agent that modulates the expression or activity of a CTGF receptor, the method comprising contacting a candidate compound with the CTGF receptor; detecting the level of CTGF receptor expression or activity in the sample; and comparing the level of CTGF receptor expression or activity in the sample to a standard level of CTGF receptor expression or activity.

In another aspect, the present invention encompasses pharmaceutical compositions comprising an effective amount of an agent that modulates the expression or activity of a CTGF receptor or fragments or subunits thereof and a suitable carrier. The agent can be a CTGF receptor agonist or antagonist, for example, or can comprise a CTGF receptor or fragments or subunits thereof and a suitable carrier.

In a further embodiment, the invention provides a method for diagnosing a CTGF-associated disorder, or identifying a predisposition or susceptibility to such a disorder, in a subject, the method comprising obtaining a sample from the subject; detecting the level of CTGF receptor expression or activity in the sample; and comparing the level of CTGF receptor expression or activity in the sample to a standard level of CTGF receptor expression or activity. In a preferred embodiment, the sample from the subject is a urine sample. In one aspect, the present invention provides for a diagnostic kit for use in diagnosing a CTGF-associated disorder, or identifying a predisposition or susceptibility to such a disorder, the kit comprising a means for detecting the level of CTGF receptor expression or activity in a sample; and a means for measuring the level of CTGF receptor expression or activity in the sample. In a preferred embodiment, the diagnostic kit of claim 17, wherein the sample is a urine sample.

Various other embodiments of the present invention are described herein.

DESCRIPTION OF THE INVENTION

Figure 1:
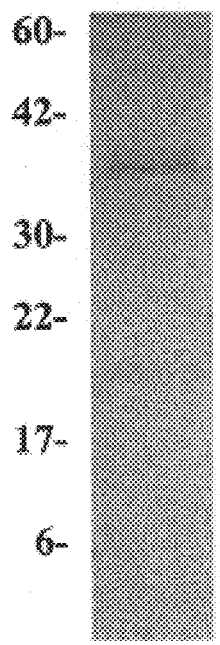
FIG. 1 sets forth data showing purified recombinant human CTGF (rhCTGF) and $^{125}$I-rhCTGF used in the examples illustrated.
Figure 1:
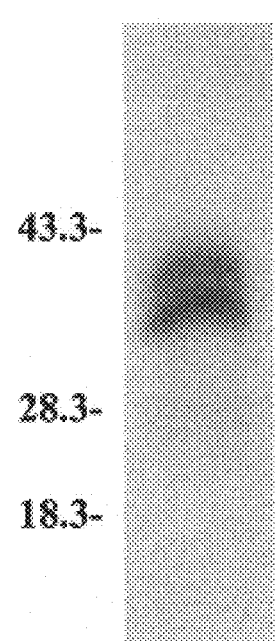

It is understood that this invention is not limited to the particular methodologies, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly-.understood by one of ordinary skill in the art to which this invention belongs. The preferred methods, devices, and materials are now described, although any methods and materials similar or equivalent to those described herein can be used in the practice or testing of the present invention. All publications mentioned herein are incorporated by reference herein for the purpose of describing and disclosing the cell lines, vectors, and methodologies reported in the publications which might be used in connection with the invention. Nothing herein is to be construed as an admission that the invention is not entitled to antedate such disclosure by virtue of prior invention. Each reference cited herein is incorporated by reference herein in its entirety.

Definitions

The term "CTGF receptor" refers to the amino acid sequences of substantially purified CTGF receptor obtained from any species, particularly a mammalian species, including bovine, porcine, murine, and, preferably, the human species, and from any source, natural, synthetic, or recombinant. "CTGF receptor" as used herein also encompasses any CTGF receptor derivative or any CTGF receptor-like compound and specifically includes any fragment or subunit of the CTGF receptor having at least one structural or functional characteristic of the CTGF receptor.

"CTGF receptor activity" refers to the ability to bind CTGF or to internalize CTGF or to otherwise effect the location, expression, and activity of CTGF.

The phrase "CTGF receptor coding sequence" refers to the polynucleotide sequence encoding the CTGF receptor or fragments or subunits thereof.

As used herein, the term "CTGF-responsive cell" refers to a cell carrying a receptor to which CTGF can bind, thereby causing the stimulation of proliferation or functional activation of that cell.

The term "agonist" refers to a molecule which, when bound to the CTGF receptor, increases or prolongs the duration of the effect of the CTGF receptor. Agonists may include proteins, nucleic acids, carbohydrates, or any other molecules which bind to and modulate the effects of the CTGF receptor.

"Amino acid" or "polypeptide" sequence as these terms are used herein refer to an oligopeptide, peptide, or protein sequence, or to a fragment of any of these, and to naturally occurring or synthetic molecules. "Fragments" can refer to any portion of a CTGF receptor sequence which retains at least one structural or functional characteristic of a CTGF receptor. Immunogenic fragments or antigenic fragments refer to fragments of CTGF receptor, preferably, fragments of about five to fifteen amino acids in length, that retain at least one biological or immunological aspect of CTGF receptor activity. Where "amino acid sequence" is recited to refer to the polypeptide sequence of a naturally occurring protein molecule, "amino acid sequence" and like terms are not meant to limit the amino acid sequence to the complete native sequence associated with the recited protein molecule.

The term "CTGF-associated disorders" as used herein refers to conditions and diseases associated with the expression or activity of CTGF. Such CTGF-associated disorders include, but are not limited to, excessive scarring resulting from acute or repetitive traumas, including surgery or radiation therapy, and systemic or acute fibrosis of organs such as the kidney, lungs, liver, eyes, heart, and skin, including scleroderma, keloids, and hypertrophic scarring. Abnormal expression of CTGF has been associated with general tissue scarring, tumor-like growths in the skin, and sustained scarring of blood vessels, leading to impaired blood-carrying ability, hypertension, hypertrophy, etc. Also associated with CTGF are various diseases caused by vascular endothelial cell proliferation or migration, such as cancer, including dermatofibromas, conditions related to abnormal endothelial cell expression, breast carcinoma desmoplasia, angiolipoma, and angioleiomyoma. Other related conditions include atherosclerosis and systemic sclerosis, including atherosclerotic plaques, inflammatory bowel disease, Chrohn's disease, angiogenesis, and other proliferative processes which play central roles in atherosclerosis, arthritis, cancer, and other disease states, neovascularization involved in glaucoma, inflammation due to disease or injury, including joint inflammation, tumor growth metastasis, interstitial disease, dermatological diseases, arthritis, including chronic rheumatoid arthritis, arteriosclerosis, diabetes, including diabetic nephropathy, hypertension, and other kidney disorders, and fibrosis resulting from chemotherapy, radiation treatment, dialysis, and allograft and transplant rejection.

The "proliferative" processes and disorders referred to herein include, but are not limited to, any of the diseases or disorders listed above, for example, kidney fibrosis, scleroderma, pulmonary fibrosis, arthritis, hypertropic scarring, and atherosclerosis. CTGF-associated proliferative disorders also include diabetic nephropathy and retinopathy, hypertension, and other kidney disorders, angiogenesis-related disorders, including but not limited to, growth of blood vessels associated with tumor formation, and other proliferative processes which play central roles in atherosclerosis, arthritis, and other disease states, including, for example, skin, cardiac, pulmonary, and renal fibrosis. In general, severe fibrosis involving kidney, liver, lung, and the cardiovascular system are included herein.

The term "antagonist" refers to a molecule which, when bound to the CTGF receptor, decreases the extent or duration of the effect of the biological or immunological activity of the CTGF receptor. Antagonists may include proteins, nucleic acids, carbohydrates, antibodies, or any other molecules which decrease the effect of the CTGF receptor.

The phrase "antibody" refers to intact molecules as well as to fragments thereof, such as Fab, F(ab')$_2$, and Fv fragments, which are capable of binding the epitopic determinant. Antibodies that bind the CTGF receptor can be prepared using intact polypeptides or using fragments containing small peptides of interest as the immunizing antigen. The polypeptide or oligopeptide used to immunize an animal (e.g., a mouse, rat, rabbit, etc.) can be derived from the translation of RNA, or synthesized chemically, and can be conjugated to a carrier protein if desired. Commonly used carriers chemically coupled to peptides include, for example, bovine serum albumin, thyroglobulin, and keyhole limpet hemocyanin (KLH).

The term "antisense" refers to any composition containing a nucleic acid sequence which is complementary to the "sense" strand of a specific nucleic acid sequence. Antisense molecules may be produced by any method available in the art including by synthesis or transcription. Once introduced into a cell, the complementary nucleotides combine with natural sequences produced by the cell to form duplexes and to block either transcription or translation.

The term "composition" as it refers to compositions containing the CTGF receptor or fragments or subunits thereof, or nucleic acid sequences encoding the same, refers broadly to any composition including CTGF receptor polypeptides or polynucleotides. The composition may comprise a dry formulation or an aqueous solution. Compositions comprising polynucleotide sequences encoding the CTGF receptor or fragments or subunits thereof, or polynucleotide sequences complementary to these, may be employed as hybridization probes. The probes may be stored in freeze-dried form and may be associated with a stabilizing agent such as a carbohydrate. In hybridizations, the probe may be deployed in an aqueous solution contaitning salts (e.g., NaCl), detergents (e.g., sodium dodecyl sulfate), and other components (e.g., Denhardt's solution, dry milk, salmon sperm DNA, etc.).

The terms "disorders" and "diseases" are used inclusively and refer to any condition deviating from normal.

As used herein, the term "extracellular matrix" refers broadly to non-cellular matrix, typically composed of proteins, glycoproteins, complex carbohydrates, and other macromolecules.

Extracellular matrix components include, for example, collagens, such as collagen types I and IV, fibronectin, laminin, and thrombospondin.

The term "fibrosis" refers to abnormal processing of fibrous tissue, or fibroid or fibrous degeneration. Fibrosis can result from various injuries or diseases, and can often result from chronic transplant rejection relating to the transplantation of various organs. Fibrosis typically involves the abnormal production, accumulation, or deposition of extracellular matrix components, including overproduction and increased deposition of, for example, collagen and fibronectin. "Fibrosis" is used herein in its broadest sense referring to any excess production or deposition of extracellular matrix proteins. There are numerous examples of fibrosis, including the formation of scar tissue following a heart attack, which impairs the ability of the heart to pump. Diabetes frequently causes damage/scarring in the kidneys which leads to a progressive loss of kidney function. Even after surgery, scar tissue can form between internal organs causing contracture, pain, and in some cases, infertility. Major organs such as the heart, kidney, liver, eye, and skin are prone to chronic scarring, commonly associated with other diseases. Hypertrophic scars (non-malignant tissue bulk) are common form of fibrosis caused by burns and other trauma. In addition, there are a number of other fibroproliferative disorders, including scleroderma, keloids, and atherosclerosis, which are associated respectively with general tissue scarring, tumor-like growths in the skin, or sustained scarring of blood vessels which impairs blood carrying ability. As CTGF is overexpressed in fibrotic disorders, it represents a very specific target for the development of anti-fibrotic therapeutics. CTGF can be inhibited through the use of small molecules and neutralizing antibodies, for example, in the treatment of fibroproliferative disorders. It is understood that "proliferative" refers to any of the above pathological instances and should not be limited to cellular proliferation.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example,-the concentrations of salt or formamide in the pre-hybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The phrases "nucleic acid" or "polynucleotide" sequence as used herein refer to an oligonucleotide or nucleotide sequence and to any fragments thereof. These terms also refer to DNA or RNA of genomic or synthetic origin which may be single-stranded or double-stranded and may represent a sense or antisense strand, to peptide nucleic acid (PNA), or to any DNA-like or RNA-like material, natural, recombinant, or synthetic in origin.

The term "substantial amino acid homology" refers to molecules having a sequence similarity of approximately 75% or more, preferably 85% or more and more preferably 90–95% to a specific sequence. The phrases "% similarity" or "% identity" refer to the percentage of sequence similarity or identity found in a comparison of two or more amino acid or nucleic acid sequences and can be determined by methods well-known in the art. Percent similarity between amino acid sequences can be calculated, for example, using the clustal method. (See, e.g., Higgins, D. G. and P. M. Sharp (1988) *Gene* 73:237–244.)

The term "sample" is used herein in its broadest sense. Samples may be derived from any source, for example, from bodily fluids, secretions, tissues, cells, or cells in culture including, but not limited to, saliva, blood, urine, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. A sample can be in solution or can be, for example, fixed or bound to a substrate. A sample can refer to any material suitable for testing for the presence of CTGF or the CTGF receptor or suitable for screening for molecules that bind to the CTGF receptor or fragments or subunits thereof. Methods for obtaining such samples are within the level of skill in the art.

The term "variant" as used in reference to the CTGF receptor refers to an amino acid sequence altered by one or more amino acids. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software. (DNASTAR Inc., Madison, Wis.)

The Invention

The present invention generally relates to the discovery and identification of a CTGF receptor. In particular, CTGF specifically bound and was cross-linked to a monomeric protein which migrated to greater than 400 kDa on SDS-PAGE. Further molecular weight characterization by gel filtration showed the CTGF receptor protein had a molecular mass of about 620 kDa. Little if any of the receptor mass was attributable to N-linked carbohydrate or glycosarninoglycan chains. CTGF bound with relatively high affinity to a single site on the surface of many cells tested; however, two-site binding was observed in a least one cell type examined. CTGF binding was specific, as other growth factors did not compete for binding. Cross-linking studies showed that CTGF bound to the 620 kDa protein with an affinity of approximately 1 nM. The CTGF receptor was affinity purified, and sequence analysis of the purified protein revealed that the receptor for CTGF is the low density lipoprotein receptor related protein, LRP. Expression of LRP and CTGF were coincident in most cells and tissues, including, but not limited to, the heart (adult and fetal), skeletal muscle, spleen, kidney (adult and fetal), liver (adult and fetal), placenta, lung, pituitary gland, spinal cord, thymus, mammary gland, adrenal gland, thyroid gland, bladder, and uterus.

Cells genetically deficient in LRP did not bind to CTGF, nor did CTGF cross-link to the CTGF receptor on such cells. The CTGF/CTGF receptor complex was immunoprecipitated with antibodies to LRP. Competitive binding experiments showed that CTGF binding to the CTGF receptor was inhibited by known ligands to LRP, and antibodies to LRP also competed for binding of CTGF to the CTGF receptor. Therefore, the mass spectrometry sequence data, cross-linking analysis with LRP deficient cells, and competition of CTGF binding with many LRP ligands, confirmed that LRP is a receptor for CTGF. Additionally, CTGF was internalized and subsequently degraded by an LRP-dependant mechanism. TGF-decreased the rate of internalization and degradation of CTGF by the CTGF receptor. Antibodies that block binding of CTGF to the CTGF receptor (for example, antibodies to LRP) greatly increased the concentration of CTGF in the culture media and cell layer.

The present invention provides for the identification and the production of compositions comprising the CTGF receptor or fragments or subunits thereof, and compositions comprising CTGF receptor coding sequences or fragments thereof. In one embodiment, the present invention comprises compositions containing polynucleotide sequences encoding the CTGF receptor or fragments or subunits thereof, or polynucleotide sequences complementary to these sequences, which polynucleotide sequences can hybridize to endogenous CTGF receptor-coding sequence and effect the expression and activity of the CTGF receptor. In a further embodiment, the compositions of the present invention comprise CTGF receptors or fragments or subunits thereof capable of specifically binding to CTGF or fragments thereof.

In preferred embodiments of the present invention, the CTGF receptor or fragments or subunits thereof, or the polynucleotide sequences encoding or complementary to sequences encoding the CTGF receptor or fragments or subunits thereof, are derived from a human source. In other embodiments, homologous receptors are derived from vertebrate species, including, but not limited to, piscine, avian, lapine, ovine, caprine, bovine, porcine, murine, equine, canine, and feline species.

The present invention also provides for cloning of the gene encoding for a CTGF receptor and fragments or subunits thereof, and provides for methods of obtaining the amino acid sequences of a CTGF receptor and fragments or subunits thereof, as well as oligonucleotide probes or primers which can hybridize to a gene encoding CTGF receptors or fragments or subunits thereof. The present invention also provides for recombinant organisms and progeny thereof comprising a gene encoding the CTGF receptor or fragments or subunits thereof, in which the recombinant organism does not express the CTGF receptor above background level or does not contain a CTGF receptor-encoding gene prior to transformation. In addition, the present invention also contemplates the use of anti-sense expression of the CTGF receptor to prevent expression of the CTGF receptor, as described infra.

Polynucleotide sequences of the present invention can be obtained by several methods. For example, CTGF receptor polynucleotides sequences can be isolated using any available hybridization procedure, including, but not limited to, hybridization of probes to genomic or cDNA libraries to detect shared nucleotide sequences; antibody screening of expression libraries to detect shared structural features; and screening for CTGF receptor sequences by use of direct ligand binding techniques.

Screening procedures that rely on nucleic acid hybridization make it possible to isolate any gene sequence from any organism, provided the appropriate probe is available. For example, oligonucleotide probes, which correspond to a part of the sequence encoding the protein in question, can be synthesized chemically. The nucleic acid sequence encoding the protein can be deduced from the genetic code. The invention contemplates each and every possible variation of nucleic acid sequence that could be made by selecting combinations based on possible codon choices, as known in the art. It will be appreciated by those skilled in the art that these combinations are made in accordance with the standard triplet genetic code. All possible variations are to be considered as being specifically disclosed.

It is possible to perform a mixed addition reaction when the sequence is degenerate. This includes, for example, a heterogeneous mixture of denatured double-stranded DNA. For such screening, hybridization is preferably performed on either single-stranded DNA or denatured double-stranded DNA. Hybridization is particularly useful, for example, in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to the specific probe in the mixture which is its complete complement. (See, e.g., Wallace, et al. (1981) *Nucleic Acid Research* 9:879.)

In accordance with the invention, polynucleotide sequences encoding the CTGF receptor or fragments or subunits thereof may be used to generate recombinant polynucleotides that direct the expression of CTGF receptors or functional equivalents thereof in appropriate host cells. Also encompassed by the invention are polynucleotide sequences which hybridize to sequences encoding the CTGF receptor or subunits or fragments thereof and can be used in nucleic acid hybridization assays, Southern and Northern blot analyses, etc. In one embodiment, for example, one of skill in the art could, using available methods, perform in situ hybridization studies mapping the distribution of CTGF receptors throughout the body and examine the potential physiological role of these receptors in the formation of connective tissue, or perform studies of receptor structure involving mutated or chimeric receptors to explore structure/function relations and second messenger interactions in order to identify specifically tailored agonist/antagonist molecules.

Due to the inherent degeneracy of the genetic code, other nucleic acid sequences which encode substantially the same or a functionally equivalent amino acid sequence, may be used in the practice of the invention for the cloning and expression of CTGF receptors and fragments or subunits thereof. Such sequences include those capable of hybridizing to human CTGF receptor sequence under stringent conditions.

Altered nucleic acid sequences which may be used in accordance with the invention include sequences having deletions, additions, or substitutions of different nucleotide residues, resulting in sequences that encode the same or functionally equivalent gene products. The gene product itself may contain deletions, additions, or substitutions of amino acid residues within the CTGF receptor sequence that result in silent changes, thus producing a functionally equivalent protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid;

positively charged amino acids include lysine and arginine; and amino acids with uncharged polar head groups having similar hydrophilicity values include leucine, isoleucine and valine; glycine and analine; asparagines and glutamine; serine and threonine; phenylalanine and tyrosine.

The nucleic acid sequences of the invention may be engineered in order to alter the CTGF-receptor coding sequence for a variety of purposes including, but not limited to, production of sequences with alterations which modify processing and expression of the gene product, or which modify activities of the gene product. Mutations may be introduced using techniques are well known in the art. For example, site-directed mutagenesis can be used to insert new restriction sites. In addition, in certain expression systems, such as yeast, host cells may over-glycosylate the gene product. When using such expression systems, it may be preferable to alter CTGF receptor coding sequences to eliminate any N-linked glycosylation sites.

The CTGF receptor sequence may be ligated to a heterologous sequence to encode a fusion protein. For example, in screening of peptide libraries, it may be useful to encode a chimeric CTGF receptor protein expressing a heterologous epitope recognized by a commercially available antibody. A fusion protein may also be engineered by methods well-known in the art to contain a cleavage site located between the CTGF receptor sequence and heterologous protein sequence, for example, a sequence encoding a growth factor related to PDGF, so that the CTGF receptor can be cleaved away from the heterologous moiety.

CTGF receptor coding sequences may also be synthesized in whole or in part, using chemical or synthetic methods well known in the art. (See, for example, Caruthers, et al. (1980) *Nucl. Acids Res. Symp. Ser.* 7:215–233; Crea and Horn (1980) *Nucl. Acids Res.* 9(10):2331; Matteucci and Caruthers (1980) *Tetrahedron Lett.* 21:719; and Chow and Kempe (1981) *Nucl. Acids Res.* 9(12):2807–2817.) For example, peptides can be synthesized by various solid phase techniques. (See, e.g., Creighton, T. (1983) "Proteins Structures And Molecular Principles," W. H. Freeman and Co., N.Y. pp. 34–60.) Automated synthesis can be achieved using, for example, the ABI 431A Peptide Synthesizer (Perkin Elmer) or other instrumentation and methodologies known in the art. The composition of the synthetic peptides may be confirmed by amino acid analysis or sequencing using, for example, the Edman degradation procedure, or other methods well-known in the art.

The invention also encompasses a polypeptide variant of the CTGF receptor amino acid sequence. In particular, such a variant amino acid sequence will have substantial amino acid sequence homology to the CTGF receptor sequence. Preferably, the variant will have at least about 75%, more preferably at least about 85%, and most preferably at least about 90 to 95% homology to the CTGF receptor amino acid sequence. The polypeptide variants of the invention have amino acid sequences having at least one functional or structural characteristic of a CTGF receptor.

Functional analysis of CTGF receptor expression, as described within the present invention, such as expression of CTGF receptor or CTGF receptor variants, or expression of CTGF receptor antisense sequences to inhibit CTGF receptor expression, may be performed by any number of CTGF bioassays well known in the art. (Bradham et al. (1991) *J. Cell Biol.* 114:1285–1294; Frazier et al. (1996) *J. Invest. Dermatol.* 107:404–411; Kothapalli et al. (1997) *Cell Growth Differ.* 8:61–68; Shinozaki et al. (1997) *Biochem Biophys. Res. Comm.* 237:292–296; Grotendorst (1997) *Cytokine Growth Factor Res,* 8:171–179; Kothapalli et al. (1998) *FASEB J.* 12:1151–61; Dammeier et al. (1998) *Int. J. Biochem. Cell Biol.* 30:909–922; Ball et al. (1998) *Biol. Reprod.* 59:828–835; Babic et al. (1999) *Mol. Cell. Biol.* 19:2958–2966; Shimo et al. (1999) *J. Biochem.* (Tokyo) 126:137–145; Nakanishi and Takigawa (1999) *Seikagaku* 71:429–432; Jedsadayanmata et al. (1 999) *J. Biol. Chem.* 274:24321–24327; Nakanishi and Takehara (1999) *J. Cell. Physiol.* 181:153–159; Duncan et al. (1999) *FASEB J.* 13:1774–1786; Hishikawa et al. (1999) *Circulation* 100:2108–2112; Kothapalli and Grotendorst (2000) *J. Cell. Physiol.* 182:119–126; Clarkson et al. (1999) *Curr. Opin. Nephrol. Hypertens.* 8:543–548; Hishikawa et al. (1999) *J. Biol. Chem.* 274:37461–37466; Hishikawa et al. (1999) *Eur. J. Pharmacol.* 385:287–290; Nakanishi et al. (2000) *Endocrinology* 141:264–273; Hong et al. (1999) *Lab. Invest.* 79:1655–1667; Hertel et al. (2000) *Eur. J. Neurosci.* 12:376–380; Hishikawa et a.l. (2000) *Eur. J. Pharmacol.* 392:19–22; Nishida et al. (2000) *J. Cell. Physiol.* 184:197–206; and Shi-wen et al. (2000) *Exp. Cell. Res.* 259:213–224.)

Expression

Nucleic acid sequences encoding a CTGF receptor can be expressed in vitro by nucleic acid transfer into a suitable host cell. The term also includes any progeny of the subject host cell. It is understood that all progeny may not be identical to the parental cell since there may be mutations that occur during replication. However, such progeny are included when the term "host cell" is used.

In order to express a CTGF receptor, fragment, or subunit, the polynucleotide sequence encoding for the protein, or a functional equivalent thereof, may be inserted into an appropriate expression vector, i.e., a vector which contains the necessary elements for the transcription and translation of the inserted coding sequence.

Methods well-known to those skilled in the art can be used to construct expression vectors containing CTGF receptor sequences and appropriate transcriptional and translational control signals. These methods can include in vitro and in vivo recombinant technologies and synthetic techniques. (See, e.g., Maniatis et al. (1989) *Molecular Cloning: A Laboratory Manual,* Chapters 4, 8, 16, and 17, Cold Spring Harbor Press, Plainview, N.Y.; and Ausubel, F. M. et al. (1995) *Current Protocols in Molecular Biology,* Chapters 9, 13, and 16, John Wiley and Sons, New York, N.Y.)

A variety of expression vector/host systems well-known in the art may be utilized to express sequences encoding the CTGF receptor. These systems include, but are not limited to, microorganisms such as bacteria transformed with recombinant bacteriophage, plasmid, or cosmid DNA expression vectors; yeast transformed with recombinant yeast expression vectors; insect cell systems transformed with recombinant virus expression vectors (e.g., baculovirus); plant cell systems transformed with recombinant virus expression vectors (e.g., cauliflower mosaic virus (CaMV), tobacco mosaic virus (TMV), etc.) or bacterial expression vectors (e.g., Ti or BR322 plasmids); filamentous fungi transformed with fungal vectors; animal cell systems, preferably mammalian systems, including those transformed with recombinant virus expression vectors (e.g., adenovirus, vaccinia virus) human tumor cells (including HT-1080), etc.; and cell lines engineered to contain multiple copies of the CTGF receptor DNA either stably amplified (CHO/dhfr) or unstably amplified in double-minute chromosomes (e.g., murine cell lines).

In bacterial systems, a number of expression vectors may be advantageously selected depending upon the use intended for the expressed CTGF receptor. For example, when large quantities of CTGF receptor for screening purposes are desired, vectors which direct the expression of high levels of fusion protein products that are readily purified may be desirable. Such vectors include, but are not limited to, multifunctional *E. coli* cloning and expression vectors such as pUR278, in which the CTGF receptor coding sequence may be ligated into the vector in frame with the lac Z coding region so that a hybrid AS-lac Z protein is produced; pIN vectors; BLUESCRIPT vectors (Stratagene, La Jolla, Calif.); and the like. (See, e.g., Ruther et al. (1983) *EMBO J.* 2:1791; Inouye and Inouye (1985) *Nucl. Acids Res.* 13:3101–3109; and Van Heeke and Schuster (1989) *J. Biol. Chem.* 264:5503–5509.) pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned polypeptide of interest can be released from the GST moiety.

A variety of yeast expression systems can be used to produce the present polypeptides. A number of vectors containing constitutive or inducible promoters may be used in yeast systems. (See, e.g., Ausubel et al, supra, Ch. 13; Grant et al. (1987) "Expression and Secretion Vectors for Yeast" in *Methods in Enzymology,* Wu and Grossman, eds., Acad. Press, N.Y. 153:516–544; Glover (1986) *DNA Cloning,* Vol. II, IRL Press, Wash., D.C., Ch. 3; Bitter (1987) "Heterologous Gene Expression in Yeast" in *Methods in Enzymology,* Berger and Kimmel, eds., Acad. Press, N.Y. 152:673–684; and Strathern et al., eds., *The Molecular Biology of the Yeast Saccharomyces* (1982) Cold Spring Harbor Press, Vols. I and II.

In one embodiment, the proteins of the invention can be expressed using host cells from the yeast *Saccharomyces cerevisiae. Saccharomyces cerevisiae* can be used with any of a large number of expression vectors available in the art, including a number of vectors containing constitutive or inducible promoters such as α factor, alcohol oxidase, and PGH. (See, e.g., Ausubel et al. supra; and Grant et al. (1987) *Methods Enzymol.* 153:516–544.) One of the most commonly employed expression vectors is the multi-copy $2\mu$ plasmid that contains sequences for propagation both in yeast and *E. coli,* including a yeast promoter and terminator for efficient transmission of the foreign gene. Vectors incorporating $2\mu$ plasmids include, but are not limited to, pWYG4, which has the $2\mu$ ORI-STB elements, the GALI promoter, and the $2\mu$ D gene terminator. Additional systems that can be used include host cells from *Pichia pastoris* or *Hansenula polymorpha,* which can provide high level expression of heterologous sequences.

A plant expression system can also be used in methods of producing the present polypeptides. In cases where plant expression vectors are used, the expression of the CTGF receptor coding sequence may be driven by any of a number of promoters, the selection and use of which is within the level of skill in the art. Such promoters include, for example, viral promoters such as the 35S RNA and 19S RNA promoters of CaMV or the coat protein promoter of TMV; plant promoters such as the small subunit of RUBISCO; and heat shock promoters, e.g., soybean hsp17.5-E or hsp17.3-B. (See, e.g., Brisson et al. (1984) *Nature* 310:511–514; Takamatsu et al. (1987) *EMBO J.* 6:307–311; Coruzzi et al. (1984) *EMBO J.* 3:1671–1680; Broglie et al. (1984) *Science* 224:838–843; Gurley et al. (1986) *Mol. Cell. Biol.* 6:559–565.) Constructs can be introduced into plant cells using Ti plasmids, Ri plasmids, plant virus vectors, direct DNA transformation, microinjection, electroporation, and other methods known in the art. (See, e.g., Weissbach and Weissbach (1988) "Methods for Plant Molecular Biology," Academic Press, NY, Section VIII, pages 421–463; and Grierson and Corey (1988) "Plant Molecular Biology," 2d Ed., Blackie, London, Chapters 7 through 9.)

Insect systems can allow for the production of the CTGF receptor or fragments or subunits thereof in large quantities. In one such system, *Autographa californica* nuclear polyhedrosis virus (AcNPV) is used as a vector to express foreign genes in, for example, *Spodoptera frugiperda* cells or in Trichoplusia larvae. Sequences encoding the CTGF receptor or precursors of the present invention may be cloned into non-essential regions of the virus, for example, the polyhedron gene, and placed under control of an AcNPV promoter, for example, the polyhedron promoter. Successful insertion of a coding sequence will result in inactivation of the polyhedron gene and production of non-occluded recombinant virus (i.e., virus lacking the proteinaceous coat encoded by the polyhedron gene). These recombinant viruses are then used to infect *Spodoptera frugiperda* cells or Trichoplusia larvae in which polynucleotides encoding the gelatins or gelatin precursors are expressed. (See, e.g., Engelhard, E. K. et al. (1994) *Proc. Nat. Acad. Sci.* 91:3224–3227; and Smith et al. (1983) *J. Virol.* 46:584; Smith, U.S. Pat. No. 4,215,051.) Further examples of this expression system may be found in, e.g., Ausubel et al., supra.

Recombinant production of the present polypeptides can also be achieved in insect cells by infection of baculovirus vectors containing the appropriate polynucleotide sequences, including those encoding any post-translational enzymes that might be necessary. Baculoviruses are very efficient expression vectors for the large scale production of various recombinant proteins in insect cells. Various methods known in the art can be employed to construct expression vectors containing a sequence encoding a polypeptide of the present invention and the appropriate transcriptional and translational control signals. (See, e.g., Luckow et al. (1989) *Virology* 170:31–39; and Gruenwald, S. and J. Heitz (1993) *Baculovirus Expression Vector System: Procedures & Methods Manual,* Pharmingen, San Diego, Calif.)

Filamentous fungi may also be used to produce the CTGF receptor polypeptides of the instant invention. Vectors for expressing and/or secreting recombinant proteins in filamentous fungi are well known in the art, and one of skill in the art could, using methods and products available in the art, use these vectors in the presently recite methods. (See, e.g., U.S. Pat. No. 5,834,191.)

In animal, particularly, in mammalian host cells, a number of viral-based expression systems may be utilized. In cases where an adenovirus is used as an expression vector, sequences encoding the CTGF receptor and fragments or subunits thereof of the present invention may be ligated into an adenovirus transcription/translation complex consisting of the late promoter and tripartite leader sequence. This chimeric gene may then be inserted in the adenovirus genome by in vitro or in vivo recombination. Insertion in a non-essential E1 or E3 region of the viral genome may be used to obtain a viable virus capable of expressing the CTGF receptor and fragments or subunits thereof of the present invention in infected host cells. (See, e.g., Logan, J. and Shenk, T. (1984) *Proc. Natl. Acad. Sci.* 81:3655–3659.) Alternatively, the vaccinia 7.5 K promoter may be used.

(See, e.g., Mackett et al. (1982) *Proc. Natl. Acad. Sci. USA* 79:7415–7419 (1982); Mackett et al (1984), *J. Virol.* 49:857–864; Panicali et al., (1982) *Proc. Natl. Acad. Sci. USA* 79:4927–4931.) In addition, transcription enhancers, such as the Rous sarcoma virus (RSV) enhancer or cytomegalovirus (CMV) enhancer, may be used to increase expression in mammalian host cells.

A preferred expression system in mammalian host cells is the Semliki Forest virus. Infection of mammalian host cells, for example, baby hamster kidney (BHK) cells and chinese hamster ovary (CHO) cells can yield very high recombinant expression levels. Semliki Forest virus is a preferred expression system as the virus has a broad host range such that infection of mammalian cell lines will be possible. More specifically, it is expected that the use of the Semliki Forest virus can be used in a wide range of hosts, as the system is not based on chromosomal intergration, and therefore will be a quick way of obtaining modifications of the recombinant CTGF receptor and fragments or subunits thereof, in studies aiming at identifying structure-function relationships and testing the effects of various hybrid molecules. Methods for constructing Semliki Forest virus vectors for expression of exogenous proteins in mammalian host cells are described in, for example, Olkkonen et al. (1994) *Methods Cell Biol.* 43:43–53.

Transgenic animals may also be used to express the CTGF receptor and fragments or subunits thereof of the present invention. Such system is constructed by operably linking a nucleic acid sequence encoding collagen to a promoter and other required or optional regulatory sequences capable of effecting expression in mammary glands. Likewise, required or optional post-translational enzymes may be produced simultaneously in the target cells employing suitable expression systems. Methods of using transgenic animals to recombinantly produce proteins are known in the art. In another embodiment, the CTGF receptor sequence is expressed in human tumor cells, such as HT-1080, which have been stably transfected with a CTGF receptor expression vector containing a CTGF receptor coding sequences and a neomycin resistance gene, or other stable selection marker known in the art.

The control elements or regulatory sequences—e.g., enhancers, promoters, 5' and 3' untranslated regions—of the above-described systems vary in strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage γ, plac, ptrp, ptac (ptrp-lac hybrid promoter), and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; and when generating cell lines that contain multiple copies of CTGF receptor DNA, SV40-, BPV- and EBV-based vectors may be used with an appropriate selectable marker.

Specific initiation signals may also be required for efficient translation of inserted CTGF receptor coding sequences. These signals include the ATG initiation codon and adjacent sequences. In cases where the entire CTGF receptor gene, including its own initiation codon and adjacent sequences, is inserted into the appropriate expression vector, no additional translational control signals may be needed. However, in cases where only a portion of the CTGF receptor coding sequence is inserted, exogenous translational control signals, including the ATG initiation codon, can be provided. Furthermore, the initiation codon must be in phase with the reading frame of the CTGF receptor coding sequence to ensure translation of the entire insert. These exogenous translational control signals and initiation codons can be of a variety of origins, both natural and synthetic. As well-known to one of skill in the art, the efficiency of expression may be enhanced by the inclusion of appropriate transcription enhancer elements, transcription terminators, etc.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, W138, HT-1080, etc.

For long-term, high-yield production of recombinant proteins, stable expression is preferred. For example, cell lines which stably express CTGF receptor may be engineered. Rather than using expression vectors which contain viral origins of replication, host cells can be transformed with CTGF receptor DNA controlled by appropriate expression control elements (e.g., promoter, enhancer, sequences, transcription terminators, polyadenylation sites, etc.) and a selectable marker. Following the introduction of foreign DNA, engineered cells may be allowed to grow for one to two days in enriched media, and then switched to selective media. The selectable marker in the recombinant plasmid confers resistance to the selection and allows cells to stably integrate the plasmid into their chromosomes and grow to form foci that in turn can be cloned and expanded into cell lines.

A number of selection systems may be used, including, but not limited to, the herpes simplex virus thymidine kinase, hypoxanthine-guanine phosphoribosyl-transferase, and adenine phosphoribosyl-transferase genes, which can be employed in $tk^-$, $hgprt^-$ or $aprt^-$ cells, respectively. (See, e.g., Wigler et al. (1977) *Cell* 11:223; Lowy et al. (1980) *Cell* 22:817.) Antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin genes. (See, e.g., Wigler et al. (1980) *Proc. Natl. Acad. Sci.* 77:3567; O'Hare et al. (1981) *Proc. Natl. Acad. Sci.* 78:1527; Mulligan and Berg (1981) *Proc. Natl. Acad. Sci.* 78:2072; Colberre-Garapin et al. (1981) *J. Mol. Biol.* 150:1; and Santerre et al. (1984) *Gene* 30:147.) Recently, additional selectable genes have been described, for example, trpB, which allows cells to utilize indole in place of tryptophan;

hisD, which allows cells to utilize histinol in place of histidine (Hartman & Mulligan (1988) *Proc. Natl. Acad. Sci. USA* 85:8047); and other selectable systems known in the art. (See, e.g., McConlogue et al. (1987) "Current Communications in Molecular Biology," Cold Spring Harbor Laboratory.)

Host cells which contain the coding sequence and which express the biologically active gene product may be identified by various methods known in the art, including, but not limited to, those described herein. In one approach, the presence of CTGF receptor coding sequence inserted in the expression vector can be detected by DNA-DNA or DNA-RNA hybridization using probes comprising nucleotide sequences homologous to the CTGF receptor coding sequence or fragments or derivatives thereof In another approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, in a preferred embodiment, the CTGF receptor coding sequence can be inserted within a neomycin-resistance marker gene sequence of a vector, and recombinants containing CTGF receptor coding sequence are identified by the absence of the marker gene function. Alternatively, a marker gene can be placed in tandem with CTGF receptor sequence under the control of the same promoter used to control the expression of CTGF receptor coding sequence or a different promoter. Expression of the marker in response to induction or selection indicates expression of CTGF receptor coding sequence.

In one approach, transcriptional activity for the CTGF receptor coding region can be assessed by hybridization assays. For example, RNA can be isolated and analyzed by, for example, northern blots, using a probe homologous to the CTGF receptor coding sequence or fragments or derivatives thereof. Alternatively, total nucleic acids of the host cell may be extracted and assayed for hybridization to such probes.

Various means of detecting CTGF receptors, well-known in the art, can be used in the practice of the present methods. In one approach, involving the detection of the biologically active CTGF receptor gene product, radioactive or other labels can be incorporated into CTGF by the various product methods known in the art without concomitant loss of biological activity. (Hebert, C. A. et al. (1991) *J. Biol. Chem.* 266:18989; and McColl, S. et al. (1993) *J. Immunol.* 150:4550–4555.) Receptor-bearing cells are incubated with labeled CTGF. The cells are then washed to remove unbound CTGF, and receptor-bound CTGF is identified and quantified.

Suitable labels include radionuclides, enzymes, substrates, cofactors, inhibitors, fluorescent agents, chemiluminescent agents, magnetic particles and the like. The use is widely described in the literature. (See, e.g., U.S. Pat. Nos. 3,817,837; 3,850,752; 3,939,350; 3,996,345; 4,277,437; 4,275,149; and 4,366,241.) Also, recombinant immunoglobulins may be produced as shown in U.S. Pat. No. 4,816,567, incorporated by reference herein in its entirety. Other approaches, such as affinity purification, rely on the usefulness of CTGF as a purification reagent for CTGF receptor in identifying receptor-bearing cells. For example, CTGF can be covalently coupled to a chromatography column. Receptor-bearing cells are extracted, and the extract is passed over the column. The CTGF receptor binds to the column by virtue of its biological affinity for CTGF, and can be quantified when unbound receptor is removed.

In an alternate method, mRNA is obtained from receptor-bearing cells and made into a cDNA expression library. The library is transfected into a population of cells, and those cells in the population that express the receptor can be selected using, for example, fluorescently labeled CTGF. The receptor can be identified by recovering and sequencing recombinant DNA from labeled cells. When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

cDNA libraries can be generated using CTGF receptor-bearing cell types such as those described below in Table 1, and the cDNAs encoding the CTGF receptor can then be determined by methods well-known in the art. The cDNAs thus identified can be cloned into expression vectors and transfected into suitable host cells by various methods available to those of skill in the art, such as those described above. In choosing host cells, it may be preferable to choose host cells that do not normally express CTGF receptor so that the expression of CTGF receptor by the transfectants can be monitored.

Figure 2:
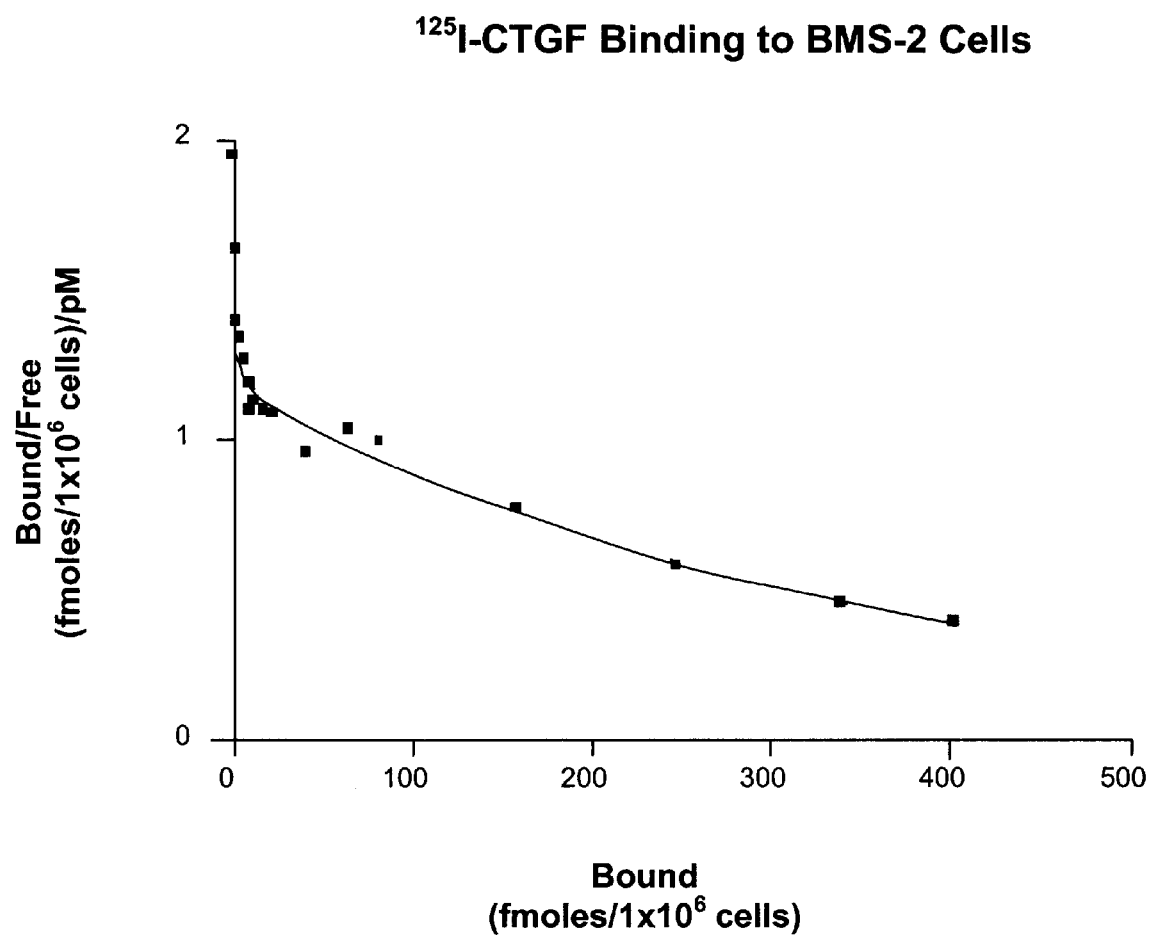
FIG. 2 sets forth a equilibrium binding analysis of rhCTGF to BMS2 cells.

With respect to methods for obtaining sequence data using pools of cDNA, such approaches more specifically involve making cDNA libraries from total mRNA or polyA+ selected mRNA from CTGF receptor-bearing cell types. CTGF receptor-bearing cell types have been identified, as seen from the equilibrium binding assay results shown in FIG. 2 and the information presented in Table 1.

TABLE 1

| SOURCE | CELL TYPE |
| --- | --- |
| Bone/Cartilage | BMS2 (murine bone marrow stromal cells) |
|  | MG63 (osteosarcoma) |
|  | Primary rat chondrocytes |
|  | Primary rat osteocytes |
|  | C5 and C12 (chondrocyte stem cells) |
| Circulatory system | Endothelial cells |
| Lung | Ovine aortic smooth muscle cells |
|  | Ovine lung myofibroblasts |
| Liver | Ito Cells |
|  | Myofibroblasts/lipocytes |
| Kidney | NRK (normal rat kidney fibroblasts) |
|  | 16KC2 (rat mesangial cells) |
| Nervous System | Astrocytes |
|  | Schwann cells |
| Fibroblasts | NIH3T3 (murine embryo) |
|  | 10T ½ (murine embryo) |
|  | Foreskin fibroblasts (human) |
|  | Scleroderma fibroblasts (human) |

Non-linear regression analysis of equilibrium binding data was performed using PRISM software (GraphPad, San Diego, Calif.). In some cells examined, two classes of binding sites for CTGF were identified. One site, with a $K_d$ of about 137 pM, present at less than about 50,000 sites per cell, is referred to as the high affinity binding site. Another site, referred to as the low affinity binding site, generally demonstrated a $K_d$ of about 1 nM and was typically present at greater than about 50,000 sites per cell (see FIG. 2).

Other cells examined showed only a single class of binding affinity, generally having binding sites that demonstrated a $K_d$ of about 1 nM. One of skill in the art would recognize that binding affinities and receptor numbers may vary from one cell source to another, or from one cell state to another. Cells that have shown negative or undetectable levels for CTGF receptor include MLEC (a transformed line of mink lung epithelial cells) and CHO-K1 cells.

Therapeutics

The over-expression of CTGF is highly associated with the onset and extent of various fibrotic and proliferative disorders. In addition, induction of CTGF expression and activity has been shown to accelerate wound healing, and bone, tissue, and cartilage repair. Therefore, CTGF and the CTGF receptor may be important therapeutic targets in CTGF-associated disorders.

The present invention provides for methods of treating diseases or disorders associated with altered expression and activity of CTGF, including conditions arising from the over-production or under-production of connective tissue and increased or decreased deposition of extracellular matrix. The present invention provides methods for the treatment of diseases, disorders, or conditions wherein the treatment involves modulation, such as inhibition or enhancement, of CTGF expression and activity, through manipulation and control of the interaction between CTGF and CTGF receptors or through activation or inactivation of the receptors independently of CTGF.

In one aspect, the present invention provides methods for treating CTGF-associated disorders arising from the over-production or over-expression of connective tissue and extracellular matrix. Such diseases, disorders, or conditions include excessive scarring resulting from acute or repetitive traumas; systemic or acute fibrosis of organs such as the kidney, lungs, liver, eyes, heart, and skin, including scleroderma, keloids, and hypertrophic scarring, general tissue scarring, and tumor-like growths in the skin; sustained scarring of blood vessels, leading to impaired blood-carrying ability, hypertension, hypertrophy, etc.; diseases caused by vascular endothelial cell proliferation or migration, such as cancer, including dermatofibromas, conditions related to abnormal endothelial cell expression, breast carcinoma desmosplasis, angiolipoma, and angioleiomyoma; atherosclerosis and systemic sclerosis, including atherosclerotic plaques, inflammatory bowel disease, and Chrohn's disease; angiogenesis, including angiogenesis-related disorders involving, growth of blood vessels associated with tumor formation, as well as other proliferative processes which play central roles in atherosclerosis, arthritis, cancer, and other disease states; neovascularization involved in glaucoma; inflammation due to disease or injury, including joint inflammation; tumor growth metastasis; interstitial disease; dermatological diseases; arthritis, including chronic rheumatoid arthritis; arteriosclerosis; diabetes, including diabetic nephropathy, retinopathy, hypertension, and other kidney disorders; and fibrosis resulting from chemotherapy, radiation treatment, dialysis, and allograft and transplant rejection.

In treating these disorders, a decrease in the concentration or expression of CTGF can be desired, such as where an appropriate course of treatment a reduction in the expression and activity of CTGF and extracellular matrix proteins, such as when treating a CTGF-associated proliferative disorder such as with fibrotic or sclerotic disease, cancer, angiogenesis, and atherosclerosis. A preferred method of treatment could include the administration of a composition that enhanced the ability of CTGF to bind to the CTGF receptor or the uptake of CTGF by the CTGF receptor, or otherwise increased the CTGF receptor activity of the CTGF receptor.

The methods of the present invention also include the use of the CTGF receptor and subunits and fragments thereof, in soluble form, as CTGF antagonists for use in effecting the biological activity of CTGF. For example, the CTGF receptor may be useful as therapeutic composition in the treatment of disease wherein the receptor composition binds to CTGF, and prevents CTGF from binding to the CTGF receptor, thereby preventing over-expression of CTGF, and over-production of extracellullar matrix scar on CTGF-associated disorders.

In another aspect, the present invention provides methods of inducing CTGF expression and activity in order to effect tissue, bone, or cartilage repair, or to otherwise increase the concentration or expression and activity of CTGF. Therefore, the present invention provides methods of treatment wherein modulation, including induction, of CTGF activity, desirably effects, for example, tissue, cartilage, and bone repair. A preferred method of treatment could include the administration of a composition that interfered with the binding of CTGF to the CTGF receptor, such as by competitively binding to the CTGF receptor or by otherwise decreasing the ability of the CTGF receptor to bind to or process CTGF, or by effecting the ability of the receptor to participate in downstream signaling.

In one embodiment of the present invention, methods for treatment of CTGF-associated disorders involve the administration of a therapeutically effective amount of an antibody which specifically reacts with the CTGF receptor or fragments or subunits thereof. In one method, the antibody blocks the binding of CTGF to its cellular receptors. In this aspect, the present invention provides that the antibody reactive with CTGF modulates the biological activity of CTGF through the manipulation and control of the interaction between CTGF and its receptor by inactivation of the receptor independently of CTGF.

In one embodiment, a method of the present invention involves the administration of a therapeutically effective amount of an antisense oligonucleotide having a sequence capable of binding specifically with any sequences of an mRNA molecule which encodes the CTGF receptor, so as to prevent translation of CTGF receptor mRNA.

Diagnostics

Another aspect of the present invention provides methods for diagnosing CTGF-associated disorders, including fibrotic and sclerotic disorders, angiogenesis, and cancer, and other proliferative disorders. In one embodiment of the present invention, a composition comprising the CTGF receptor or fragments or subunits thereof can be contacted with a biological sample under conditions suitable for binding of CTGF to the CTGF receptor, and the CTGF/CTGF receptor complex can be detected. A comparison of the amount of CTGF/CTGF receptor complex in the sample to that in a non-disease sample can provide an indication of whether CTGF expression and activity is altered, and thus indicate whether the subject has or is at risk for a CTGF-associated disorder. The diagnostics tools and methods of the present invention may also include imaging systems known in the art which utilize the CTGF receptor. Further, the CTGF receptor or fragments or subunits thereof can also be included in a kit for detection of disorders associated with altered expression and activity of CTGF. For example, diagnostic kits for assays utilizing radioimmunoassay (RIA), fluorescent immunoassay, or ELISA (enzyme-linked immunoabsorbent assay) techniques are specifically contemplated.

The present invention is further directed to a method of detecting or diagnosing the presence of a pathology characterized by an excessive accumulation of the extracellular matrix components, in particular, those associated with decreased or increased expression and activity of CTGF.

In a preferred method, the detection or diagnosis is accomplished by measuring CTGF receptor levels in a sample from a subject, preferably, a human subject. In one embodiment, the method includes determining the level of CTGF receptor in a first urine sample and comparing this level to the level of CTGF receptor present in a normal urine sample, i.e., a sample from a subject without a CTGF-associated disorder. An elevated level of CTGF in the first sample is indicative of the pathological condition in question.

More generally, detection of CTGF receptor levels, including levels of unbound and CTGF-bound receptor, may be obtained through immunoassay methods, for example, using ELISAs, RIAs, or any other assays which utilize an antibody to detect the presence of a protein marker. The ELISA and RIA methods are preferred and may be used, for example, with the monoclonal antibodies of the present invention to detect levels of CTGF receptor. In a preferred method of the invention, urine samples are obtained first from patients suspected or known to have a CTGF-associated disorder. Levels of CTGF receptor in this first sample are measured, for example, through immunoassay, and are compared with the CTGF receptor levels in a second sample, the second sample being obtained from a patient known to have a CTGF-associated disorder or from a patient known not to have any CTGF-associated disorder, to determine the presence or progression of such a disorder. The same methods may be used to monitor the progression of a CTGF-associated disorder.

More generally, antibodies specific for a target polypeptide, such as antibodies specific for the CTGF receptor or fragments or subunits thereof, are useful in the present invention for diagnosis of CTGF-associated disorders. The present diagnostic assays include methods utilizing the antibody and a label to detect the CTGF receptor in a sample from a patient suspected of having a CTGF-associated disorder. The sample could comprise, for example, body fluids, cells, tissues, or extracts of such tissues, including, for example, cells micro-dissected from biopsy material. Protocols employed to screen for and identify antibodies having the desired specificity can also be used for the detection of the CTGF receptor or fragments or subunits thereof in the sample.

Preferably, in the diagnostic methods of the present invention, normal or standard values for CTGF receptor expression, or for normal levels of CTGF/CTGF receptor binding are established in order to provide a basis for the diagnosis of the existence of a CTGF-associated disorder a predisposition to a CTGF-associated disorder. In one of the methods of the present invention, this is accomplished by combining body fluids or cell extracts taken from normal subjects with antibody to the CTGF receptor under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified CTGF receptor or fragments or subunits thereof. Standard values obtained from normal samples may be compared, for example, in a specific embodiment, with values obtained from samples from subjects suspected of having a CTGF-associated disorder, or having a predisposition to a CTGF-associated disorder. Deviation between standard and subject values establishes the presence of or predisposition to the disease state. The diagnostic methods of the present invention may also be directed to the detection of a predisposition or susceptibility to a renal disorder. This can be accomplished, for example, by detecting a marker indicative of a predisposition or susceptibility to develop a particular disorder, for example, diabetes. The marker can comprise, for example, a genetic polymorphism.

Monoclonal antibodies can be detected by methods discussed, for example, infra. Monoclonal antibodies against the CTGF receptor can be conjugated to an appropriate enzyme such as horseradish peroxidase, protein ferritin, enzyme alkaline phosphatase, β-D-galactosidase, etc. These enzyme-linked antibody preparations can be mixed with, for example, urine samples that contain unknown amounts of CTGF receptor, bound or unbound, in an indirect ELISA. Direct or sandwich ELISAs could also be performed using the same antibodies.

RIA techniques may also be used to measure levels of the CTGF receptor in, for example, urine. For example, CTGF receptor or fragments or subunits thereof may be radioactively labeled and mixed with monoclonal antibodies specific for the CTGF receptor and a serum sample containing an unknown amount of unlabeled CTGF receptor. The labeled and unlabeled CTGF receptor compete for binding with the monoclonal antibody. By measuring the amount of radioactivity of the reaction mixture, the amount of CTGF receptor present in the sample can be quantitatively determined. See, e.g., U.S. Pat. Nos. 4,438,209 and 4,591,573. Non-competitive RIAs can also be performed.

Polynucleotide sequences encoding the CTGF receptor or fragments or subunits thereof can be used for the diagnosis of conditions or diseases associated with increased levels of CTGF receptor expression and activity. For example, polynucleotide sequences encoding the CTGF receptor may be used in hybridization or PCR assays of fluids or tissues from biopsies to detect CTGF receptor expression and activity. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The present invention provides kits for detecting CTGF receptor in samples, in particular, in fluid samples. In a preferred embodiment, the diagnostic kits of the present invention contain reagents for measuring levels of CTGF receptor in urine samples. In a particular embodiment, this kit comprises a monoclonal antibody specific for CTGF receptor or fragments or subunits thereof bound to a support and a second monoclonal antibody specific for a different CTGF receptor epitope and enzyme-labeled. The kit further comprises reagents for detecting the enzyme-labeled monoclonal antibody. The reagent kit employs immunological methods in measuring CTGF receptor in the urine sample, thus allowing for the detection and monitoring of kidney disorders and diseases. In particular embodiments, the kit allows for the detection and monitoring of fibrotic and sclerotic disorders resulting from, for example, diabetes and hypertension. In another embodiment, the kit comprises a radio-labeled or fluorescein labeled antibody in place of the enzyme-labeled antibody.

In one embodiment, the diagnostic kit of the present invention comprises elements useful in the detection of CTGF receptor in tissue samples, using immunohistochemical techniques. The kit could be used in conjunction with, for example, a software program which allows for quantitative measurement of the levels of CTGF receptor in the tissue sample by image analysis or other comparative techniques. Another embodiment provides a diagnostic kit for detecting and measuring levels of CTGF receptor mRNA in tissue samples. In one embodiment, the kit comprises reagents used to reverse transcribe CTGF receptor mRNA to DNA. The kit can further comprise reagents necessary to amplify CTGF receptor-specific DNA, including primers complementary to polynucleotides encoding CTGF receptor or fragments or subunits thereof. The kit can also include a competitive mimic or mutant cDNA for use in quantifying the level of CTGF receptor mRNA present in the sample.

In a preferred embodiment, the diagnostic kit of the present invention is packaged and labeled, for example, in box or container which includes the necessary elements of the kit, and includes directions and instructions on the use of the diagnostic kit.

Methods for Screening

The present invention additionally contemplates methods for screening for compounds that modulate the CTGF binding and internalization activities and degradation activities of CTGF receptors. The methods of the claimed invention also include the use of the CTGF receptor or fragments or subunits thereof to screen for or otherwise identify useful ligands, including agonists or antagonists, which can specifically recognize the CTGF receptors of the present invention. Compounds that bind to or are bound by CTGF receptors may activate (agonist), inhibit (antagonist), or otherwise enhance or inhibit such CTGF receptor activities. The compounds can include, for example, antibodies and fragments thereof, small molecules, polypeptides (synthetic, natural, or enzymatically- or recombinantly-produced), and aptamers.

The screening methods of the present invention can directly test for the binding of a compound to CTGF receptor. Alternatively, screening assays can test for binding of a candidate compound in the presence of a labeled competitor. Binding can be detected by a number of methods available in the art, including, for example, fluorophores, enzyme conjugates, radioisotopes, or any detectable label.

In one aspect, assays of the present invention include contacting the CTGF receptor or fragments or subunits thereof with the candidate compound, detecting a level of CTGF receptor activity or binding, for example, by detecting the presence of CTGF/CTGF receptor complexes and comparing that level of activity or binding to a standard level obtained by methods known in the art. These methods could involve CTGF receptors or compounds affixed to solid supports, cell-free preparations, or natural or synthetic product mixtures. Assays such as ELISA, can be designed in which antibodies, monoclonal or polyclonal, bind directly or indirectly to CTGF receptor or compete with CTGF receptor for binding to a ligand or ligands.

The screening methods of the present invention can be used to identify compounds that can be used in methods for treating the previously described CTGF-associated diseases, disorders, and conditions. Compounds identified using the present methods can be administered to produce the desired effect, such as activating or inhibiting CTGF receptor activity, such as the binding and/or internalization of CTGF by the CTGF receptor in a subject. Additionally, the present invention provides methods for the identification of compounds which may increase or decrease CTGF receptor activity in specific cells or tissues as desired under certain conditions.

As a consequence of the above described screening methods, as well as other known screening methods which may be applied in the context of the present invention, CTGF receptor-ligand complexes will be formed. These complexes may include complexes wherein the ligand is CTGF, a CTGF receptor antagonist, a CTGF receptor agonist, or any another compound which is capable of modulating the activities of the CTGF receptor. These complexes may be useful as therapeutic entities in their own right or as used in further characterization of the CTGF receptor, or in methods for detection and quantification of CTGF receptors in a subject or in a sample, such methods being within the level of skill in the art.

These complexes may also be used to select for other ligands which modulate CTGF receptor activity, such as agonist or antagonist ligands. An agonist is an agent that causes the receptor to be activated upon binding with the agent and an antagonist is an agent that suppresses agonist binding or otherwise inhibits the activation of the receptor. Partial agonists or antagonists of the CTGF receptor may be useful for therapeutic or diagnostic purposes.

In order to identify small molecules and other agents useful in the present methods for treating or preventing a CTGF-associated disorder by modulating the activity and expression of the CTGF receptor, the CTGF receptor or fragments or subunits thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between the CTGF receptor and the agent being tested can be measured by methods available in the art.

Other techniques for drug screening which provide for a high throughput screening of compounds having suitable binding affinity to CTGF, or to another target polypeptide useful in modulating, regulating, or inhibiting the expression and/or activity of CTGF, are known in the art. For example, microarrays carrying test compounds can be prepared, used, and analyzed using methods available in the art. (See, e.g., Shalon, D. et al. (1995) PCT Application No. WO95/35505; Baldeschweiler et al. (1995) PCT Application No. WO95/251116; Brennan, T. M. et al. (1995) U.S. Pat. No. 5,474,796; Heller, M. J. et al, (1997) U.S. Pat. No. 5,605,662.)

Identifying small molecules that modulate CTGF receptor activity can also be conducted by various other screening techniques, which can also serve to identify antibodies and other compounds that interact with the CTGF receptor and can be used as drugs and therapeutics in the present methods. (See, e.g., Enna, S. J. et al., eds. (1998) *Current Protocols in Pharmacology,* John Wiley and Sons.) Assays will typically provide for detectable signals associated with the binding of the compound to a protein or cellular target. Binding can be detected by, for example, fluorophpres, enzyme conjugates, and other detectable labels well-known in the art. (Id.) The results may be qualitative or quantitative.

For screening the agents for specific binding, various immunoassays may be employed for detecting, for example, human or primate antibodies bound to the cells. Thus, one may use labeled anti-hlg, e.g., anti-hlgM, hlgG or combinations thereof to detect specifically bound human antibody of the galactosyl epitope. Various labels can be used such as radioisotopes, enzymes, fluorescers, chemiluminescers, particles, etc. There are numerous commercially available kits providing labeled anti-hlg, which may be employed in accordance with the manufacturer's protocol.

For screening the agents for cytotoxic effects, a wide variety of protocols may be employed to ensure that one has the desired activity. One will normally use cells, which may be naturally occurring or modified, cell lines, or the like. The cells may be prokaryotic or eukaryotic. For example, if one is interested in a pathogen, where it does not matter to which epitope the compound conjugate binds, one can combine the pathogenic cells with each of the compounds in the presence of an antibody dependent cytotoxic system to determine the cytotoxic effect. One may perform this assay either prior to or subsequent to determining the effect of the various candidate compounds on cells of the host to whom the compound would be administered. In this way, one would obtain a differential analysis between the affinity for the pathogenic target and the affinity for host cells which might be encountered, based on the mode of administration.

In some situations, one would be interested in a particular cellular status, such as an activated state, as may be present with T cells in autoimmune diseases, transplantation, and the like. In this situation one would first screen the compounds to determine those which bind to the quiescent cell, and as to those compounds which are not binding to the quiescent cells, and screen the remaining candidate compounds for cytotoxicity to the activated cells. One may then screen for other cells present in the host which might be encountered by the compounds to determine their cytotoxic effect. Alternatively, one might employ cancer cells and normal cells to determine whether any of the compounds have higher affinity for the cancer cells, as compared to the normal cells. Again, one could screen the library of compounds for binding to normal cells and determine the effect. Those compounds which are not cytotoxic to normal cells could then be screened for their cytotoxic effect to cancer cells. Even where some cytotoxicity exists for normal cells, in the case of cancer cells, where there is a sufficient differentiation in cytotoxic activity, one might be willing to tolerate the lower cytotoxicity for normal cells, where the compound is otherwise shown to be effective with cancer cells.

Instead of using cells which are obtained naturally, one may use cells which have been modified by recombinant techniques. Thus, one may employ cells which can be grown in culture, which can be modified by upregulating or downregulating a particular gene. In this way, one would have cells that differ as to a single protein on the surface. One could then differentially assay the library as to the effect of members of the library on cells for which the particular protein is present or absent. In this way, one could determine whether the compound has specific affinity for a particular surface membrane protein as distinct from any of the proteins present on the surface membrane.

One may differentiate between cells by using antibodies binding to a particular surface membrane protein, where the antibodies do not initiate the complement dependent cytotoxic effect, for example, using different species, isotypes, or combinations thereof. By adding the antibodies, blocking antisera or monoclonal antibodies, to one portion of the cells, those cells will not have the target protein available for binding to the library member. In this way one creates comparative cells which differ in their response based on the unavailability in one group of a single protein. While antibodies will usually be the most convenient reagent to use, other specific binding entities may be employed which provide the same function.

For use in the assay to determine binding, one may use an antibody-dependent cytotoxic system. One could use synthetic mixtures of the ingredients, where only those components necessary for the cytotoxic effect are present. This may be desirable where components of blood or plasma may adversely affect the results of the assay.

Also, while a cellular lawn is an extremely convenient way to screen large numbers of candidates, other techniques can also be used in accordance with the present invention. These techniques include the use of multiwell plates, and the various devices used for the preparation of the combinatorial library, such as pins, tea bags, etc. One may grow the cells separately in relation to the nature of the various devices, where the device may then be contacted with the cells or have the cells grown on the device. The device may be immersed in an appropriate culture, seeded with the cells, or otherwise provided for contact between the cells and the candidate compound. After adding the cytotoxic agent, one may then analyze for lysis in a variety of methods well-known in the art.

In addition, one may wish to know whether the compound has agonist or antagonist activity. The subject assay techniques provide for a rapid way for determining those compounds present in the library which bind to the target protein. Once one has substantially narrowed the number of candidate compounds, one can use more sophisticated assays for detecting the activity of the compound itself. In this way, one can perform a rapid screen to determine binding affinity and specificity, followed by a more intensive screen to determine activity. Various techniques exist for determining activity, where the cells may be modified, so that a marker gene will be activated which will provide for a detectable signal. Conveniently, the signal may be associated with production of a dye, the production of a surface membrane protein which can be detected with labeled antibodies, or the secretion of a protein which can be detected in the supernatant by any of a variety of techniques. For example, the gene that is expressed may be luciferase modified to have a leader sequence so as to be secreted, whereby the supernatant can then be screened for light generation formation by using an appropriate substrate.

Various protocols may be employed for screening the library. To some degree, this will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the compounds are individually on a surface in a grid, so that at each site of the grid one knows what the composition is, one can provide a cellular lawn which is similarly organized as a grid and may be placed in registry with the compounds bound to the solid surface. Once the lawn and solid substrate are in registry, one may release the compounds from the surface in accordance with the manner in which the compounds are attached. After sufficient time for the compounds to bind to the proteins on the cellular surface, one may wash the cellular lawn to remove non-specifically bound compounds. One or more washings may be involved, where the washings may provide for varying degrees of stringency, depending upon the desired degree of affinity. After the washings have been completed, mammalian blood or plasma may then be added and incubated for sufficient time for cytotoxicity. The plasma or blood may then be removed and plaques observed, where the nature of the compound can be determined by virtue of the position in the grid. The plasma or blood can be free of any components that would naturally kill the cells of the lawn.

Since the preparative process may be repeated, one could prepare a plurality of solid substrates, where the same compounds are prepared at the comparable sites, so that the screening could be repeated with the same or different cells to determine the activity of the individual compounds. In some instances, the identity of the compound can be determined by a nucleic acid tag, using the polymerase chain reaction for amplification of the tag. (See, e.g., PCT Application No. WO93/20242.) In this instance, the compounds that are active may be determined by taking the lysate and introducing the lysate into a polymerase chain reaction medium comprising primers specific for the nucleic acid tag. Upon expansion, one can sequence the nucleic acid tag or determine its sequence by other means, which will direct the selection of the procedure is used to prepare the compound.

Alternatively, one may have tagged particles where the tags are releasable from the particle and provide a binary code that describes the synthetic procedure for the compounds bound to the particle. (See, e.g., Ohlmeyer, et al. (1993) *PNAS* 90:10922.) These tags can conveniently be a homologous series of alkylene compounds, which can be detected by gas chromatography-electron capture. Depending upon the nature of the linking group, one may provide for partial release from the particles, so that the particles may be used two or three times before identifying the particular compound.

While for the most part libraries have been discussed, any large group of compounds can be screened analogously, so long as the CTGF receptor epitope can be joined to each of the compounds. Thus, compounds from different sources, both natural and synthetic, including macrolides, oligopeptides, ribonucleic acids, dendrimers, etc., may also be screened in an analogous manner.

Formation of a plaque in the assay demonstrates that binding of the member of the library to the cell, usually a surface protein, does not interfere with the CTGF receptor epitope binding to an antibody, that the immune complex is sufficiently stable to initiate the complement cascade, and that the member has a high affinity for the target.

The subject methodology can be used in any situation where one has a cellular target to be killed, particularly those cellular targets having low or no CTGF receptor epitope. Thus, the cellular target maybe a prokaryote, which is pathogenic. Various organisms include, for example, microbacterium, Yersinia, Pseudomonas, *Bordetella pertussis, Treponema pallidum, Neisseria gonorrhoea,* Streptococcus, Hemophilus influenza, etc. Other pathogens include eukaryotes, particularly fungi, such as Candida, Histoplasma, etc., and protozoa, e.g., Giardia. In addition, viruses which provide for surface membrane proteins in infected cells, can also be the target of the subject compounds, where the cells that are screened have been vitally infected.

Host cells may also serve as targets, where the cells are either abnormal or act in an adverse way to the host or treatments of the host. For example, cancerous tissues that can be distinguished from normal tissue can serve as a target for the subject compounds. T or B cells associated with autoimmune diseases or associated with GVHD or transplant rejection may also serve as targets. Aberrant cells, regardless of their nature, so long as they can be distinguished from normal cells, may also serve as targets. Thus, psoriatic lesions, lymphoma cells, bacterial, fungal, parasitic, virus infected cells, may be targets of the subject products. Also, where one wishes to ablate a portion of cells, without removal of all of the cells, such as cells expressing a differentiation marker such as T cell subsets, activated platelets, endothelial cells, hormone or cytokine receptor expressing cells, the subject compounds may find application.

Antibodies

CTGF receptor antibodies may be generated using methods well known in the art. Such antibodies may include, but are not limited to, polyclonal, monoclonal, chimeric, single chain antibodies, as well as Fab fragments, including $F(ab')_2$ and $F_v$ fragments. Fragments can be produced, for example, by a Fab expression library. Neutralizing antibodies, i.e., those which inhibit dimer formation or inhibibit CTGF receptor activities, are especially preferred for therapeutic use.

A target polypeptide, such as the CTGF receptor or an agent that modulates the activity and or expression of the CTGF receptor, can be evaluated to determine regions of high immunogenicity. Methods of analysis and epitope selection are well-known in the art. (See, e.g.,Ausubel et al., eds. (1988), *Current Protocols in Molecular Biology.*) Analysis and selection can also be accomplished, for example, by various software packages, such as LASER-GENE NAVIGATOR software. (DNASTAR; Madison, Wis.) The peptides or fragments used to induce antibodies should be antigenic, but need not necessarily be biologically active. Preferably, an antigenic fragment or peptide is at least 5 amino acids in length, more preferably, at least 10 amino acids in length, and most preferably, at least 15 amino acids in length. It is preferable that the antibody-inducing fragment or peptide is identical to at least a portion of the amino acid sequence of the target polypeptide, e.g., the CTGF receptor or fragments or subunits thereof. A peptide or fragment that mimics at least a portion of the sequence of the naturally occurring target polypeptide can also be fused with another protein, e.g., keyhole limpet hemocyanin (KLH), and antibodies can be produced against the chimeric molecule.

Methods for the production of antibodies are well-known in the art. For example, various hosts, including goats, rabbits, rats, mice, humans, and others, may be immunized by injection with the target polypeptide or any immunogenic fragment or peptide thereof. Depending on the host species, various adjuvants may be used to increase immunological response. Such adjuvants include, but are not limited to, Freund's adjuvant, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and Corynebacterium parvum are especially preferable.

Monoclonal and polycolonal antibodies may be prepared using any technique which provides for the production of antibody molecules by continuous cell lines in culture. Techniques for in vivo and in vitro production are well-known in the art. (See, e.g., Pound, J. D. (1998) *Immunochemical Protocols,* Humana Press, Totowa N.J.; Harlow, E. and D. Lane (1988) *Antibodies, A Laboratory Manual,* Cold Spring Harbor Laboratory, New York.) The production of chimeric antibodies is also well-known, as is the production of single-chain antibodies. (See, e.g., Morrison, S. L. et al. (1984) *Proc. Natl. Acad. Sci.* 81:6851–6855; Neuberger, M. S. et al. (1984) *Nature* 312:604–608; Takeda, S. et al. (1985) *Nature* 314:452–454.) Antibodies with related specificity, but of distinct idiotypic composition, may be generated, for example, by chain shuffling from random combinatorial immunoglobin libraries. (See, e.g., Burton D. R., (1991) *Proc. Natl. Acad. Sci.* 88:11120–11123.)

Antibodies may also be produced by inducing in vivo production in the lymphocyte population or by screening immunoglobulin libraries or panels of highly specific binding reagents. (See, e.g., Orlandi, R. et al. (1989) *Proc. Natl.*

Acad. Sci. 86:3833–3837; Winter, G. and C. Milstein (1991) *Nature* 349:293–299.) Antibody fragments which contain specific binding sites for the target polypeptide may also be generated. Such antibody fragments include, but are not limited to, F(ab')$_2$ fragments, which can be produced by pepsin digestion of the antibody molecule, and Fab fragments, which can be generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) *Science* 254:1275–1281.)

Antibodies can be tested for anti-target polypeptide activity using a variety of methods well-known in the art. Various techniques may be used for screening to identify antibodies having the desired specificity, including various immunoassays, such as enzyme-linked immunosorbent assays (ELISAs), including direct and ligand-capture ELISAs, radioimmunoassays (RIAs), immunoblotting, and fluorescent activated cell sorting (FACS). Numerous protocols for competitive binding or immunoradiometric assays, using either polyclonal or monoclonal antibodies with established specificities, are well known in the art. (See, e.g., Harlow and Lane, supra.) Such immunoassays typically involve the measurement of complex formation between the target polypeptide and a specific antibody. A two-site, monoclonal-based immunoassay utilizing monoclonal antibodies reactive to two non-interfering topes on the target polypeptide is preferred, but other assays, such as a competitive binding assay, may also be employed. (See, e.g., Maddox, D. E., et al (1983) *J Exp Med* 158:1211.)

Antibodies as decribed above could also be used to identify the CTGF receptor or fragments or subunits thereof in a sample, e.g., from biopsied tissue, etc. The amount of CTGF receptor present could be determined, for example, by quantitative image analysis. Preferably, the antibody will distinguish between unbound CTGF receptor and CTGF receptor bound to CTGF. CTGF receptor mRNA levels could also be determined, such as by reverse transcriptase polymerase chain reaction (PCR) using portions of the biopsied tissue. In particular, in this method, mRNA from a tissue sample, in total, or that specific for CTGF receptor or fragments or subunits thereof, could be transcribed to DNA and then amplified through PCR using specific primer sequences. Quantitation of CTGF receptor mRNA could be determined, for example, by a competition reaction using equal volumes of the patient sample run against a series of decreasing known concentrations, e.g., of a mimic or mutant cDNA fragment.

The present invention contemplates the use of antibodies specifically reactive with a CTGF receptor or fragments or subunits thereof that neutralize the biological activity of CTGF. The antibody administered in the method can be the intact antibody or antigen binding fragments thereof, such as Fab, F(ab')$_2$ and F$_v$ fragments, which are capable of binding the epitopic determinant. The antibodies used in the method can be polyclonal or, more preferably, monoclonal antibodies. Monoclonal antibodies with different epitopic specificities are made from antigen-containing fragments of the protein by methods well known in the art. (See Ausubel et al., supra.)

In the present invention, therapeutic applications include those using "human" or "humanized" antibodies directed to the CTGF receptor or fragments or subunits thereof. Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a CTGF receptor is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

Antisense

The present invention provides for a therapeutic approach which effects CTGF expression and activity by interfering with the expression of the CTGF receptor. Specifically, a therapeutic approach which directly interrupts the translation of CTGF receptor mRNA into protein could be used to bind to CTGF receptor mRNA or to otherwise interfere with CTGF receptor expression.

Antisense technology relies on the modulation of expression of a target protein through the specific binding of an antisense sequence to a target sequence encoding the target protein or directing its expression. (See, e.g., Agrawal, S., ed. (1996) *Antisense Therapeutics*, Humana Press Inc., Totawa N.J.; Alama, A. et al. (1997) *Pharmacol. Res.* 36(3):171–178; Crooke, S. T. (1997) *Adv. Pharmacol.* 40:1–49; and Lavrosky, Y. et al. (1997) *Biochem. Mol. Med.* 62(1):11–22.) Antisense sequences are nucleic acid sequences capable of specifically hybridizing to at least a portion of a target sequence. Antisense sequences can bind to cellular mRNA or genomic DNA, blocking translation or transcription and thus interfering with expression of a targeted protein product. Antisense sequences can be any nucleic acid material, including DNA, RNA, or any nucleic acid mimics or analogs. (See, e.g., Rossi, J. J. et al. (1991) *Antisense Res. Dev.* 1(3):285–288; Pardridge, W. M. et al. (1995) *Proc. Nat. Acad. Sci.* 92(12):5592–5596; Nielsen, P. E. and G. Haaima (1997) *Chem. Soc. Rev.* 96:73–78; and Lee, R. et al. (1998) *Biochemistry* 37(3):900–1010.) Delivery of antisense sequences can be accomplished in a variety of ways, such as through intracellular delivery using an expression vector. Site-specific delivery of exogenous genes is also contemplated, such as techniques in which cells are first transfected in culture and stable transfectants are subsequently delivered to the target site.

Antisense oligonucleotides of about 15 to 25 nucleic acid bases are typically preferred as such are easily synthesized and are capable of producing the desired inhibitory effect. Molecular analogs of antisense oligonucleotide may also be used for this purpose and can have added advantages such as stability, distribution, or limited toxicity advantageous in a pharmaceutical product. In addition, chemically reactive groups, such as iron-linked ethylenediarnine-tetraacetic acid (EDTA-Fe), can be attached to antisense oligonucleotides, causing cleavage of the RNA at the site of hybridization. These and other uses of antisense methods to inhibit the in vitro translation of genes are well known in the art. (See, e.g., Marcus-Sakura (1988) *Anal. Biochem* 172:289.)

Delivery of antisense therapies and the like can be achieved intracellularly through using a recombinant expression vector such as a chimeric virus or a colloidal dispersion system which, upon transcription, produces a sequence complementary to at least a portion of the cellular sequence encoding the target protein. (See, e.g., Slater, J. E. et al. (1998) *J. Allergy Cli. Immunol.* 102(3):469–475.) Delivery of antisense sequences can also be achieved through various viral vectors, including retrovirus and adeno-associated virus vectors. (See, e.g., Miller, A. D. (1990) *Blood* 76:271; and Uckert, W. and W. Walther (1994) *Pharacol. Ther.* 63(3):323–347.) Vectors which can be utilized for antisense gene therapy as taught herein include, but are not limited to, adenoviruses, herpes viruses, vaccinia, or, preferably, RNA viruses such as retroviruses.

Retroviral vectors are preferably derivatives of murine or avian retrovirus. Retroviral vectors can be made target-specific by inserting, for example, a polynucleotide encoding a protein or proteins such that the desired ligand is expressed on the surface of the viral vector. Such ligand may be a glycolipid carbohydrate or protein in nature. Preferred targeting may also be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Recombinant retroviruses are typically replication defective, and can require assistance in order to produce infectious vector particles. This assistance can be provided by, for example, using helper cell lines that contain plasmids encoding all-of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal may be used. These cell lines produce empty virions, since no genome is packaged. If a retroviral vector is introduced into such cells in which the packaging signal is intact, but the structural genes are replaced by other genes of interest, the vector can be packaged and vector virion produced.

Other gene delivery mechanisms that can be used for delivery of antisense sequences to target cells include colloidal dispersion and liposome-derived systems, artificial viral envelopes, and other systems available to one of skill in the art. (See, e.g., Rossi, J. J. (1995) *Br. Med. Bull.* 51(1):217–225; Morris, M. C. et al. (1997) *Nucl. Acids Res.* 25(14):2730–2736; and Boado, R. J. et al. (1998) *J. Pharm. Sci.* 87(11):1308–1315.) For example, delivery systems can make use of macromolecule complexes, nanocapsules, microspheres, beads, and lipid-based systems including oil-in-water emulsions, micelles, mixed micelles, and liposomes.

In one embodiment, the present invention provides a colloidal delivery system that uses liposomes. Liposomes are artificial membrane vesicles useful as delivery vehicles in vitro and in vivo. It has been shown that large unilamellar vesicles (LUV), ranging in size from about 0.2 to about 4.0 $\mu$m can encapsulate a substantial percentage of an aqueous buffer containing large macromolecules. RNA, DNA, and intact virions, for example, can be encapsulated within the aqueous interior and delivered to cells in a biologically active form. (See, e.g., Fraley, et al. (1981) *Trends Biochem. Sci.*, 6:77.)

Liposomes have been used for delivery of polynucleotides in, for example, mammalian, plant, yeast, and bacterial cells. In order for a liposome to be an efficient gene transfer vehicle, the following characteristics should be present: (1) highly efficient encapsulation of the genes of interest, without comprising the biological activity of these genes; (2) preferential and substantial binding to target cells in comparison to non-target cells; (3) highly efficient delivery of vesicle contents to target cell cytoplasm; and (4) accurate and effective expression of genetic information. (See, e.g., Mannino et al. (1988) *Biotechniques* 6:682.) The composition of the liposome is usually a combination of phospholipids, particularly high-phase-transition-temperature phospholipids, usually in combination with steroids, especially cholesterol. Other phospholipids or other lipids may also be used.

Physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, in which the saturated lipid moiety contains from 14 to 18 carbon atoms, particularly from 16 to 18 carbon atoms. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific liposomes. Mechanistic targeting can be distinguished based upon whether it is passive or active. Passive targeting utilizes the natural tendency of liposomes to distribute to cells of the reticulo-endothelial system (RES) in organs containing sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cells types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bind to the surface of the targeted delivery system to find and interact with the desired cells. A ligand may be any compound of interest which will bind to another compound, such as a receptor.

Pharmaceutical Formulations and Routes of Administration

The present invention contemplates methods of treatment in which CTGF receptor molecules, or fragments or subunits thereof, or compounds that modulate the activity of CTGF receptor, are administered, for example, in vivo, to bind excess circulating CTGF or bind CTGF receptor, preventing CTGF from binding to endogenous CTGF receptor. These agents can be delivered directly or in pharmaceutical compositions along with suitable carriers or excipients, as well known in the art. Present methods of treatment can comprise administration of an effective amount of CTGF receptor or fragments or subunits thereof or agents that effect CTGF receptor activity, or compositions thereof, to a subject having a CTGF-associated disorder. In a preferred embodiment, the subject is a mammalian subject, and in a most preferred embodiment, the subject is a human subject. In one embodiment, the subject and the CTGF receptor administered are of homologous origin. Preferably, the subject and the CTGF receptor administered are human in origin.

One method of treatment involves modulating the proliferation, differentiation, or functional activation of CTGF-responsive cells and tissues in a subject. This can be achieved by administering to the subject an effective amount of CTGF receptor or fragments or subunits thereof, or compounds that modulate the activity of CTGF receptor, for a time and under conditions sufficient to reduce the activity or expression of CTGF, such as by reducing the amount of unbound CTGF. An effective amount of such agents can readily be determined by routine experimentation, as can the most effective and convenient route of administration and the most appropriate formulation. Various formulations and drug delivery systems are available in the art. (See, e.g., Gennaro, A. R., ed. (1990) Remington's Pharmaceutical Sciences, 18$^{th}$ ed., Mack Publishing Co., Easton Pa.)

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use. Proper formulation is dependent upon the route of administration chosen.

For injection, for example, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of active CTGF receptor, or fragments or subunits thereof, or compounds that effect the activity of CTGF receptor, in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For any composition used in the present methods of treatment, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of CTGF activity is desired, for example, the concentration of the test agent that achieves a half-maximal inhibition of CTGF activity can be determined. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmacological procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}$ $ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety which are sufficient to maintain or inhibit CTGF activity as desired, i.e. minimal effective concentration (MEC). The MEC will vary for each compound but can be estimated from, for example, in vitro data, such as the concentration necessary to achieve 50–90% activity of CTGF to induce bone growth using the assays described herein. Dosages necessary to achieve the MEC will depend on individual characteristics and route of administration. Agents or compositions thereof should be administered using a regimen which maintains plasma levels above the MEC for about 10–90% of the duration of treatment, preferably about 30–90% of the duration of treatment, and most preferably between 50–90%. In cases of local administratiori or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of disorders or diseases in which cartilage or bone induction, wound healing, neuroprotection or the like is desired.

The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

Example 1

Production, Purification, and Iodination of Recombinant Human CTGF (rhCTGF)

Unless otherwise indicated, the CTGF used in the following examples of the present invention was produced, purified, and iodinated as described below.

A full-length human CTGF cDNA was obtained from Dr. Gary Grotendorst (University of Miami Medical School) (Bradham, et al., 1991, J. Cell Biol., 114:1285–1294). We generated a CTGF cDNA comprising only the open reading frame by the polymerase chain reaction using DB60R32 as template and the following primers (5'-gctccgcccgcagtgggatccATGaccgccgcc-3' (SEQ ID NO: 16) and 5'-ggatccggatccTCAtgccatgtctccgta-3') (SEQ ID NO:

17), which added BamHI restriction enzyme sites (bold type) to either end of the amplified product. The resulting amplified DNA fragment was digested with BamHI, agarose gel purified, and subcloned directly into the BamHI site of the baculovirus (donor) expression plasmid pFastBac1 (Life Technologies, Inc.). The pFastBac1/CTGF cDNA was transposed into bacmid DNA and recombinant baculovirus was generated by following the manufacturer's protocol outlined in the BAC-TO-BAC Baculovirus Expression System manual. After expansion of recombinant baculovirus titers in sf9 insect cells, using standard procedures known in the art (Murphy and Piwnica-Worms, 1984, In Current Protocols in Molecular Biology, Vol. 2, Ausubel et al., eds., John Wiley & Sons, Inc.), expression and production of rhCTGF was performed as follows.

Hi 5 cells were grown at 27° C. in 900-cm$^2$ roller bottles in sf900-II media, supplemented with gentamicin (20 g/ml) and 5% fetal bovine serum until >90% confluence. Before baculovirus infection, the cells were rinsed with sf900-II media (serum free), fresh serum-free sf900-II media added (100 mls per roller bottle), and the recombinant baculovirus added at a multiplicity of infection of 5 to 10. The infection and expression were allowed to proceed for 40 to 44 hours.

The rhCTGF was purified from the conditioned media using cation exchange perfusion chromatography on a Bio-CAD Sprint (PerSeptive Biosystems, Framingham, Mass.). CTGF-containing conditioned media from the Hi 5 cells (1 liter) was passed over a 1.7 ml POROS HS-20 sulfopropyl cation exchange column with a flow rate of 10 mls/min. The column was washed (30 column volumes) with 20 mM phosphate buffer, pH 6.5, containing 150 mM sodium chloride, followed by a step gradient of this buffer containing 350 mM sodium chloride (10 column volumes). The bound rhCTGF was eluted from the column using a gradient of 350–1200 mM sodium chloride in 20 mM phosphate, pH 6.5 (20 column volumes). The rhCTGF eluted from the column between 650–850 mM sodium chloride. Fractions containing rhCTGF were pooled, diluted to 150 mM sodium choloride with 20 mM phosphate, pH 6.5 and passed over a 1.7 ml POROS CM-20 carboxymethyl cation exchange column (5 mls/min flow rate). The column was washed and the rhCTGF was eluted exactly as described above for the HS-20 cation exchange column. Fractions were analyzed for the presence and purity of rhCTGF by Coomassie staining following electrophoresis on 12% SDS-PAGE gels, as shown in FIG. 1A.

Iodination of rhCTGF was done by either of two methods known in the art. Iodination of rhCTGF (5 g) was performed using commercially available Iodobeads, and following the manufacturer's instructions (Pierce Chemical Co.). The reaction included 750 Ci of $^{125}$I-Na (carrier-free), 0.1M phosphate, pH 6.5, 0.1% CHAPS, and 50 g/ml heparin. FIG. 1B shows an autoradiograph of $^{125}$I-rhCTGF electrophoresed under non-reducing conditions on 12% SDS-PAGE. For chloramine-T mediated iodination, the procedure described by Frolick et al. (1985, J. Biol. Chem., 259:10995–11000) was modified as follows. Five micrograms of rhCTGF was incubated for 2 minutes in a reaction vial containing 5 l of 50 g/ml chloramine-T and 750 Ci of $^{125}$I-Na (carrier-free), 41 of 0.5% CHAPS, 10 g heparin, in 0.1 phosphate buffer, pH 6.5. A second 5 l aliquot of chloramine-T was added and the reaction continued for 90 seconds. A third 5 l aliquot of chloramine-T was added and the reaction continued for an additional 60 seconds.

The reaction was then quenched by the addition of 20 l of 50 mM N-acetyltyrosine. For either iodination procedure, $^{125}$I-rhCTGF was separated from unincorporated $^{125}$I by passing the reaction over an EconoPac 10DG column (BioRad Laboratories) equilibrated with 50 mM sodium phosphate buffer, pH 6.5, 0.5 M NaCl, 0.02% Triton X-100, and blocked with 0.5% BSA in equilibrium buffer. Specific activity of the iodinated rhCTGF generated by the Iodobead procedure was typically 63 Ci/g, corresponding to 0.87 moles of $^{125}$I per mole of rhCTGF. The specific activity of $^{125}$I-rhCTGF generated by chloramine-T was typically 100 Ci/g, corresponding to 1.37 moles of $^{125}$I per mole of rhCTGF. The binding parameters measured and calculated for CTGF using either method of iodination were identical.

Example 2

Equilibrium Binding Assays

Equilibrium binding assays were performed on BMS2 cells (murine bone marrow stromal cells, a gift from Dr. Jeff Gimble, Oklahoma Medical Center) plated in 24-well tissue culture dishes which had just reached confluence. The cells were incubated with varying concentrations of radioiodinated rhCTGF in phosphate buffered saline, pH 7.2, containing 0.2% bovine serum albumin (PBS/BSA) for four hours at 4° C. Free ligand concentration was determined by—counting the media from each of the wells. The cells were washed four times with ice-cold PBS/BSA, lysed with 1% Triton-X-100 in 1N sodium hydroxide, and the cell associated radioactivity, as measured by -counting, determined. (See FIG. 2). Non-specific binding was determined by including a 500-fold molar excess of unlabelled rhCTGF in adjacent wells.

Example 3

Cross-Linking Studies

Cross-linking studies were performed to biochemically characterize the CTGF receptor. Specifically, labeled CTGF was chemically cross-linked to cell surface molecules to which it bound. MG63 cells, a human osteocarinoma cell line, were plated in 6 well dishes at 2 to 4×10$^4$ cells/cm$^2$ approximately 16 hours before affinity labeling. The cells were rinsed twice with binding buffer (PBS with 0.2% BSA, 0.02% azide) and overlayed with 0.5 ml/well of binding buffer containing 100–200 pM iodinated CTGF (unless otherwise indicated).

To demonstrate specific binding, 300–500 fold excess of unlabeled CTGF was added to duplicate wells. After a binding period of 3 to 4 hours at 4° C., the binding buffer was replaced with fresh binding buffer containing 0.5 mM amine reactive cross-linking agent (bis succinimidyl suberate (BS$^3$) (Pierce Chemical Co.) or cysteine reactive crosslinking reagent (S-SMCC) (Pierce Chemical Co.), which were used interchangeably. The cells were incubated for 15 minutes at room temperature. The reaction was terminated by removing the medium and washing the cells with quench buffer (250 mM sucrose, 10 mM Tris, pH 7.4, 10 mM EDTA). The cells were lysed with 100 μl of lysis buffer (1% Triton X-100, 10 mM EDTA, 50 mM Tris, pH 7.5, 500 μM AEBSF, 1 μg/ml aprotinin, 1 μM E-64, 1 μM leupeptin) (protease inhibitor cocktail, CalBiochem), and scraped off the culture plate, and centrifuged at 12,000×g to remove the insoluble material. The soluble fractions were boiled in Laemmli gel buffer for 5 minutes with or without reduction with 50 mM dithiothreitol (DTT), and then applied to a 4–8% linear gradient SDS-PAGE. Following electrophoresis, the gels were dried down and exposed to XOMAT or BIOMAX film for autoradiography.

Figure 3:
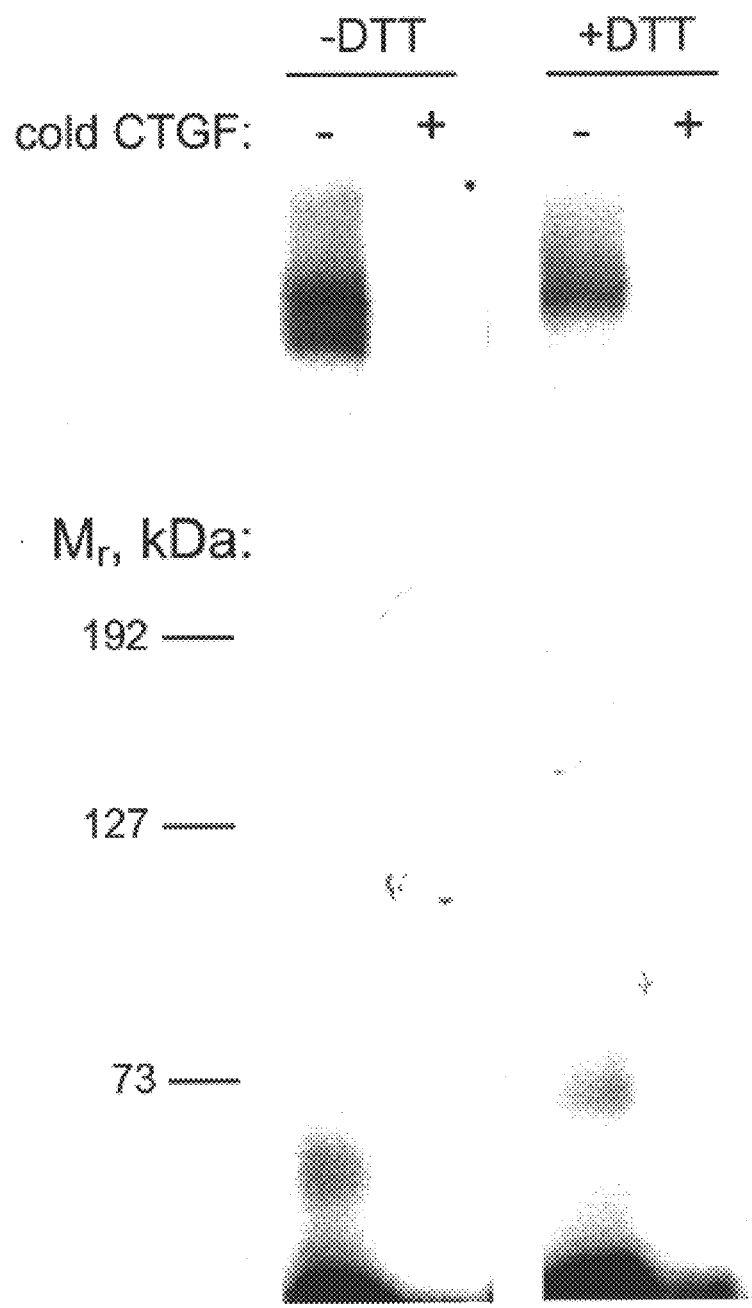
FIG. 3 sets forth data relating to the size of CTGF receptor.

As shown in FIG. 3, CTGF bound to and was cross-linked to a protein that, when unreduced, migrated to greater than about 400 kDa. Reduction with DTT did not reduce the protein size; rather, the protein migrated more slowly, indicating that the protein was monomeric and unfolded from the reductant. Incubation with the reducing agent appeared to reduce labeling of the complex, suggesting that disulfide exchange may account for some of the $^{125}$I-CTGF covalent cross-linking to the protein.

Many other cross-linking reagents were used and demonstrated the same result. In addition, titration with lower concentrations of a cross-linking agent did not produce faster migrating species (lower $M_r$), indicating that this $M_r$ species is not a multimer of subunits.

Example 4
Sizing of CTGF Receptor by Gel Filtration

Figure 4:
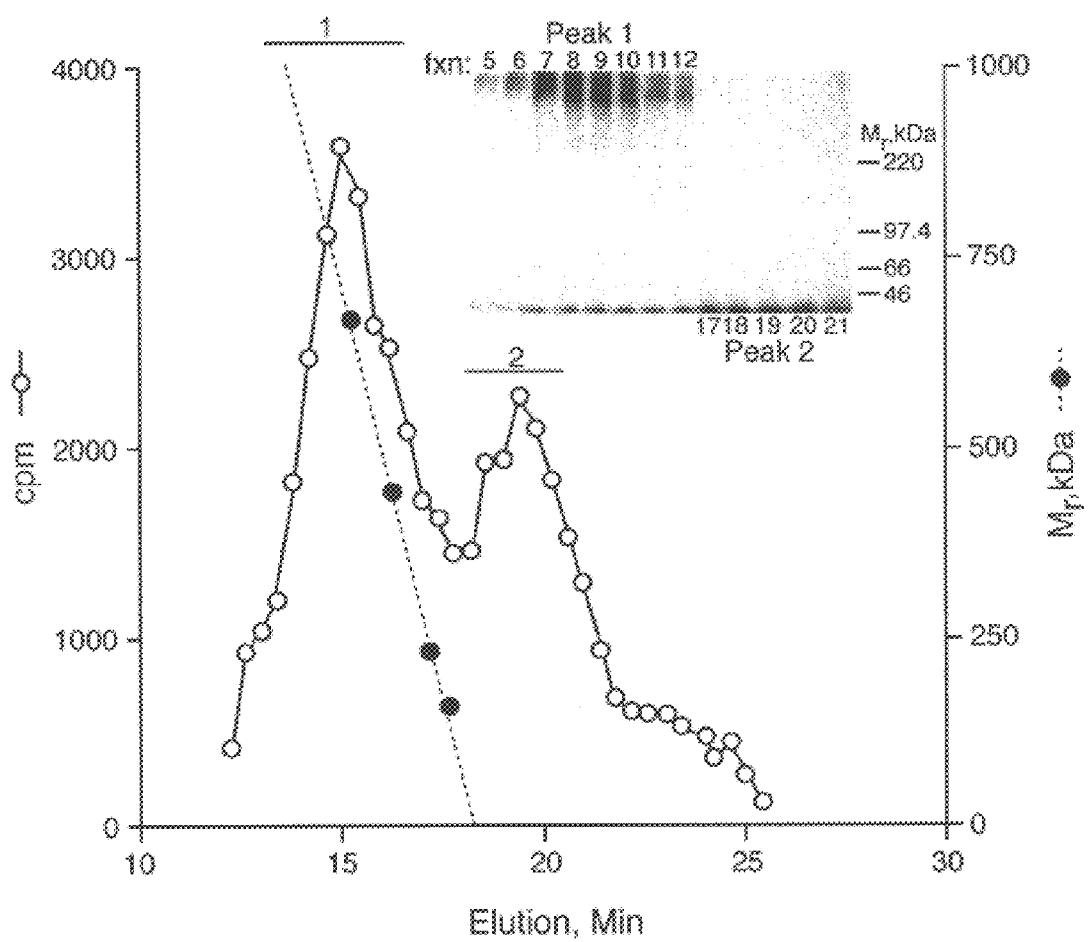
FIG. 4 provides the elution profile of CTGF receptor complex on Biogel TSK-40 and sets forth that the molecular weight of the CTGF receptor is approximately 620 kDa.

MG63 cells were affinity labeled with 200 pM $^{125}$I-CTGF and the complexes were cross-linked with 0.5 mM BS$^3$. The complexes were collected by lysing the cells with 1% Triton X-100, 50 mM Tris (pH 7.5) and the protease inhibitors as described earlier. The lysate was applied to a Biogel TSK-40 column, 300×7.5 mm (BioRad Laboratories) equilibrated with 0.1% Triton X-100 and 50 mM Tris (pH 7.5) at a flow rate of 0.2 ml/minute. 0.2 ml fractions were collected and counted in a counter. The column had been calibrated with Mass Calibration Standards (Boehringer Mannheim). As set forth in FIG. 4, the native cross-linked CTGF/CTGF receptor complex eluted coincident with the largest molecular mass marker standard, at 660 kDa. After subtracting the mass of one molecule of CTGF, the CTGF receptor protein was estimated to have a molecular mass of about 620 kDa.

Example 5
Measurement of Sugar Composition of CTGF Receptor and Related Subunits In order to determine and measure the sugar composition of the receptor, experiments were performed to determine whether the receptor was comprised of either N-linked carbohydrates or glycosaminoglycan (GAG) chains that contributed to its $M_r$. Cells (MG63 and BMS-2) were affinity labeled with iodinated CTGF and cross-linked with S-SMCC. The complexes were collected by solubilization with 1% Triton lysis buffer. As a positive control for glycoslyated proteins, iodinated TGF-β2 was cross-linked to NRK cells with DSS (disuccinimidyl suberate) and the receptor proteins were collected as for CTGF (Cheifetz et al., 1988, *J. Biol. Chem.*, 263:16984–16991).

Figure 5:
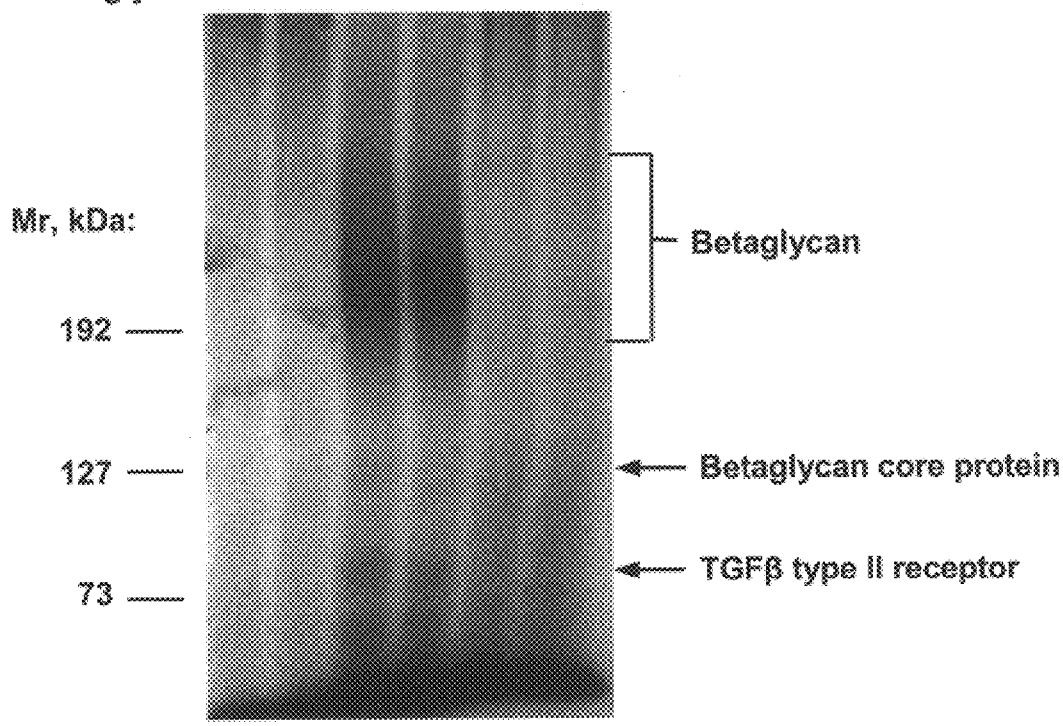
FIG. 5 sets forth data with respect to N-glycanase digestion of the CTGF/CTGF receptor complexes.
Figure 6:
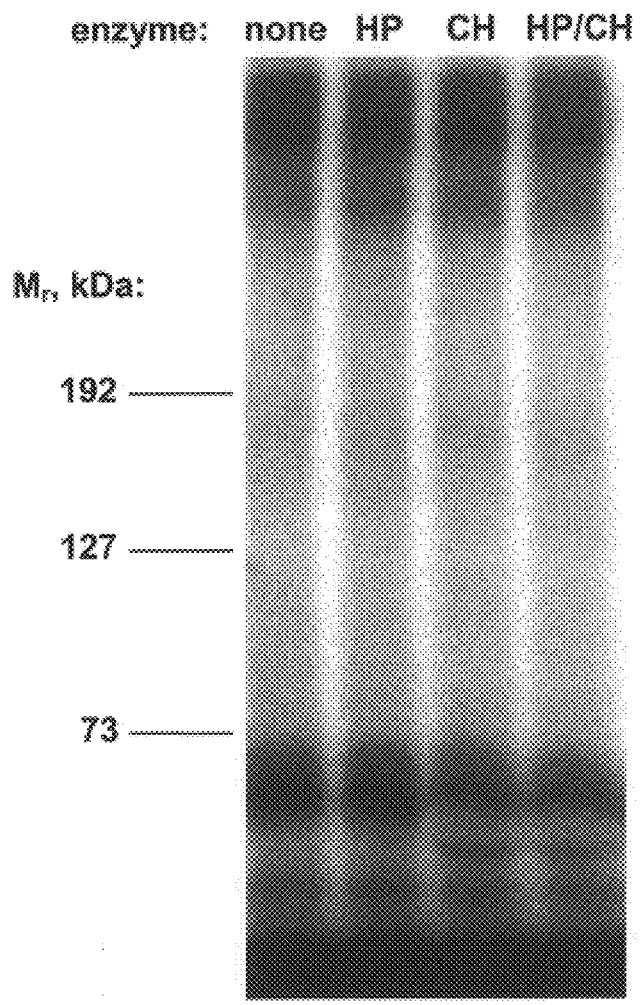
FIG. 6 sets forth results from heparitinase and chondrotinase digestion of the CTGF/CTGF receptor complexes.

The complexes (CTGF/CTGF receptor and TGF-β/TGF-receptor) were digested with N-glycanase to remove N-linked carbohydrate and separated by SDS-PAGE, as shown at FIG. 5. The TGF-β type II receptor and betaglycan core protein showed obvious shifts when treated with the N-glycanase. The CTGF/CTGF receptor complexes did not shift in migration. A similar experiment was performed with CTGF/CTGF receptor complexes from MG63 cells, digested with enzymes that remove GAG chains (FIG. 6). It appears that the complex is not sensitive to either heparitinase or chondroitinase. These experiments suggested that little, if any, of the CTGF receptor mass was made up of N-linked carbohydrate or glycosaminoglycan chains.

Example 6
Cell Survey of CTGF Receptor Complexes

Cross-linking studies were performed on a number of cell lines, as described above, to demonstrate whether CTGF bound to receptors in these cells, similar to that shown in the above examples. The cross-linking results with these cell lines are shown at FIGS. 7A, 7B, and 7C.

Figure 7A:
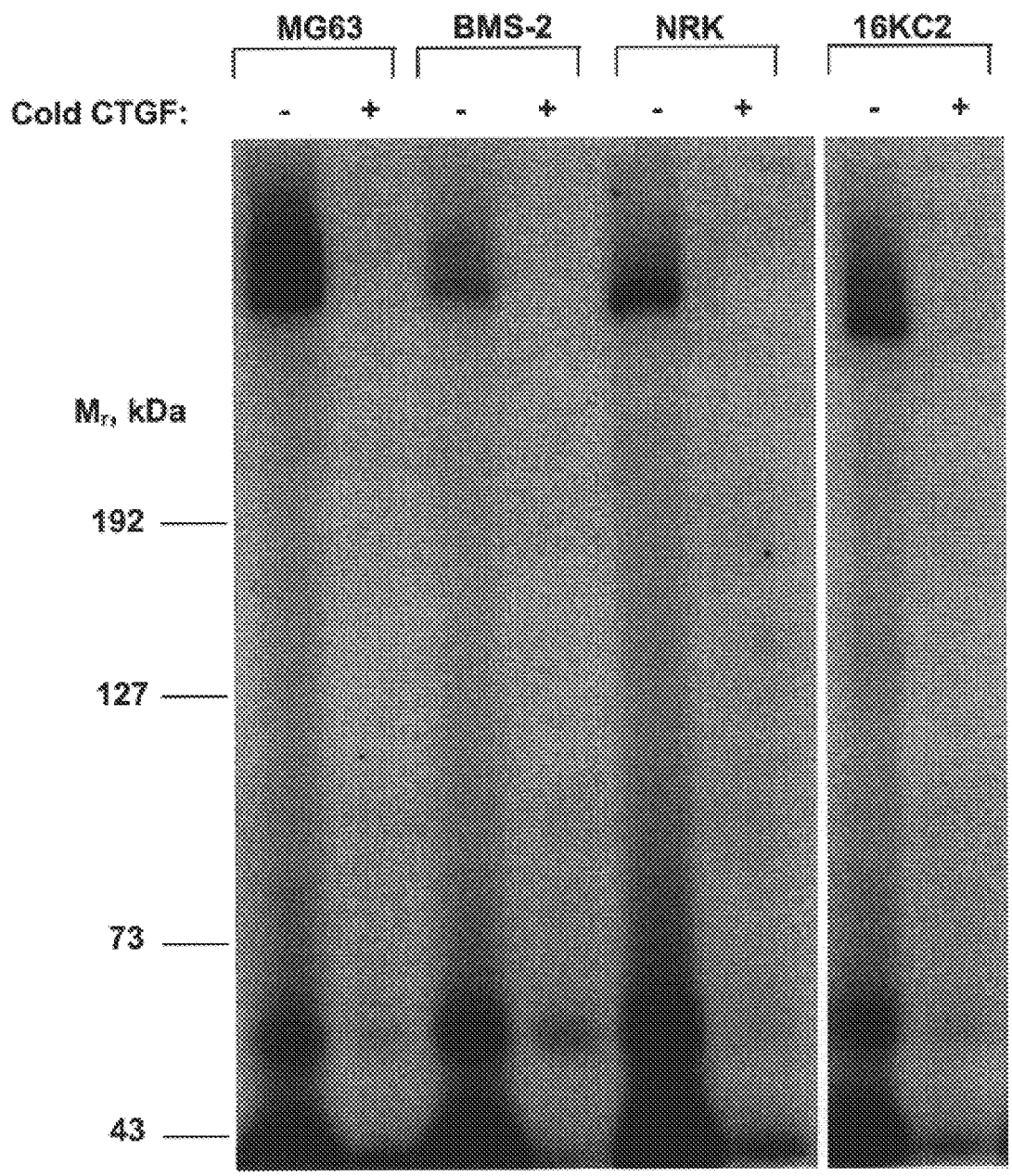
FIGS. 7A, 7B, and 7C set forth the results of cell surveys, utilizing cell lines which are comprised of CTGF receptors, to determine whether CTGF binds to similar receptors in the surveyed cells, and to determine cells lines which are not comprised of CTGF receptors.
Figure 7B:
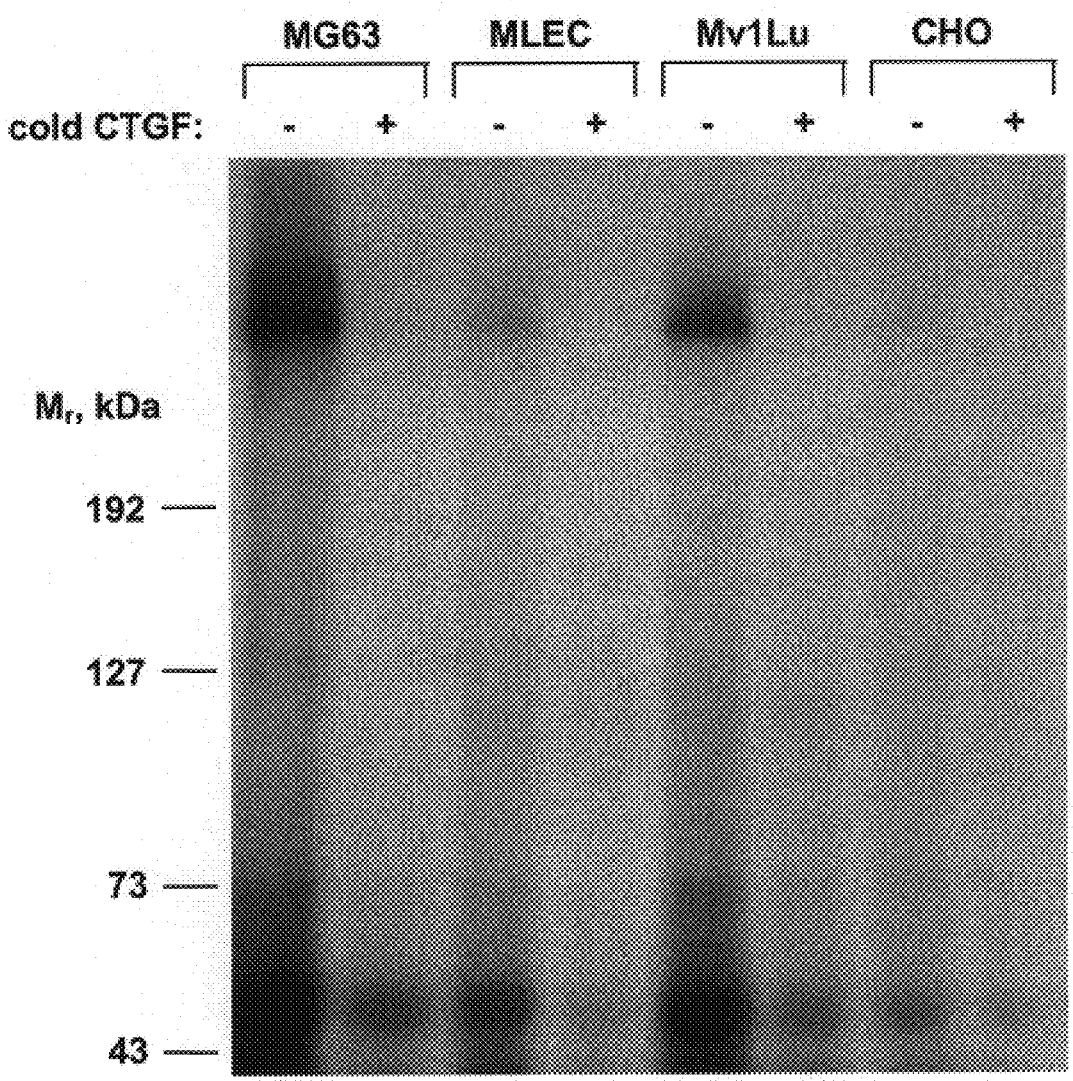
Figure 7C:
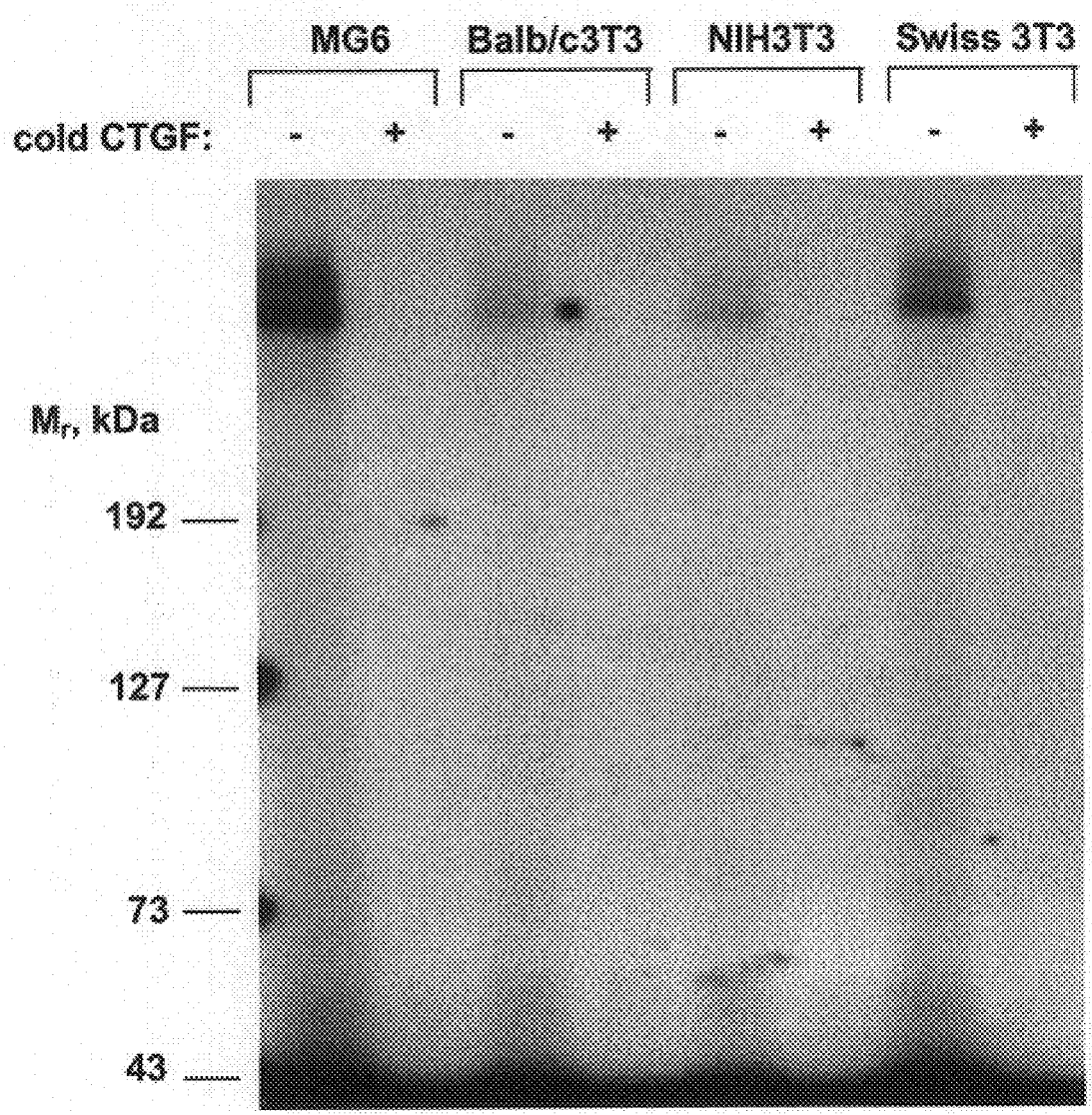

As set forth at FIG. 7A, CTGF cross-linked complexes on MG63, BMS-2, NRK and 16KC2 cells. As 16KC2 cells have fewer receptors than the other cell lines examined, the gel exposure time for these cells was increased to visualize the bands. FIG. 7B sets forth CTGF cross-linked complexes on MG63, MLEC, Mv1Lu, and CHO cells. Finally, as set forth in FIG. 7C, CTGF cross-linked complexes on MG63, Balb/c3T3, NIH3T3, and Swiss 3T3 cells.

For all cells that bound CTGF, it was observed that the cross-linked CTGF/CTGF receptor complexes migrated as a doublet with Mr>400 kDa. Cells that bound little or no CTGF (CHO and MLEC) did not appear to cross-link CTGF in this assay. The 16KC2 cell line had been shown to have only one class of receptors and showed binding to this protein.

Example 7
Affinity Binding Assays with Respect to Cross-linked Complexes

Figure 8:
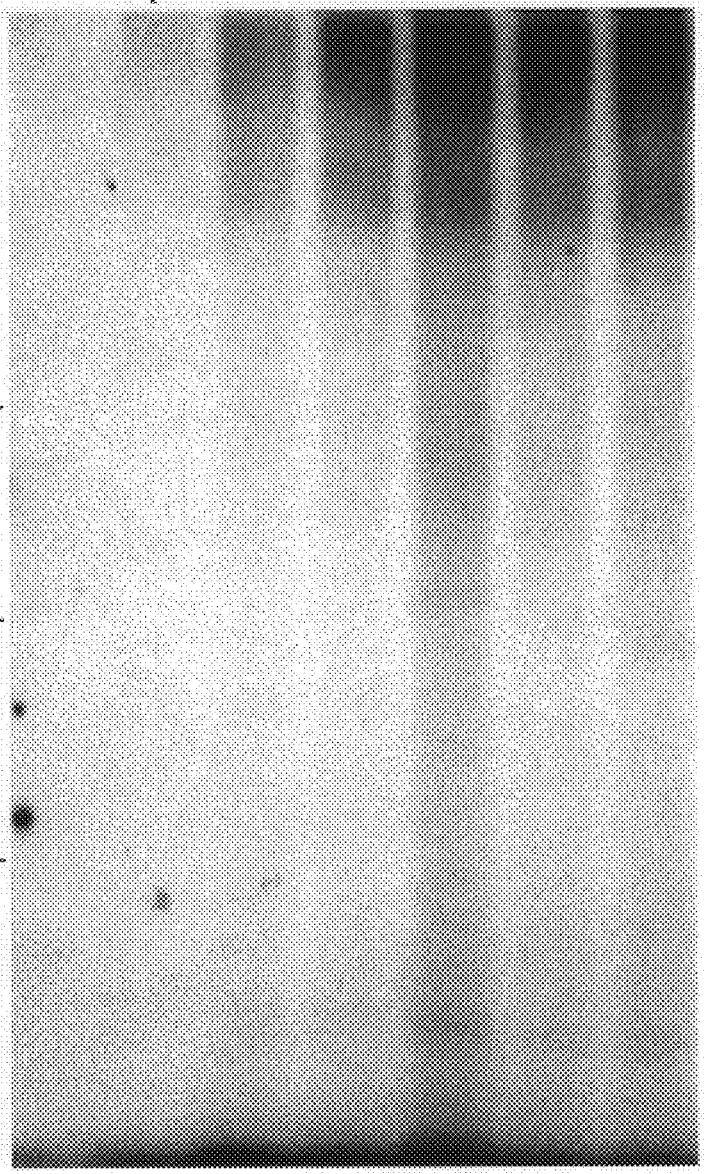
FIG. 8 sets forth the results of a titration experiment conducted to determine CTGF competitive binding.

Equilibrium binding assays demonstrated two classes of binding affinities for CTGF binding to cells. A competition experiment was performed to address the affinity of CTGF for the cross-linked complex by a competition binding experiment using cold (unlabeled) CTGF. The cells were labeled with 200 pM iodinated CTGF in the presence of 0–6.5 nM unlabeled CTGF. The samples were cross-linked with S-SMCC, reduced and are shown in FIG. 8. Densitometry of the observed bands of FIG. 8 indicated an IC$_{50}$ of approximately 1 nM. This measurement is consistent with the low affinity constant obtained in equilibrium binding experiments described above.

Example 8
Specificity of CTGF Binding with Respect to Cross-linked Complexes

Figure 9:
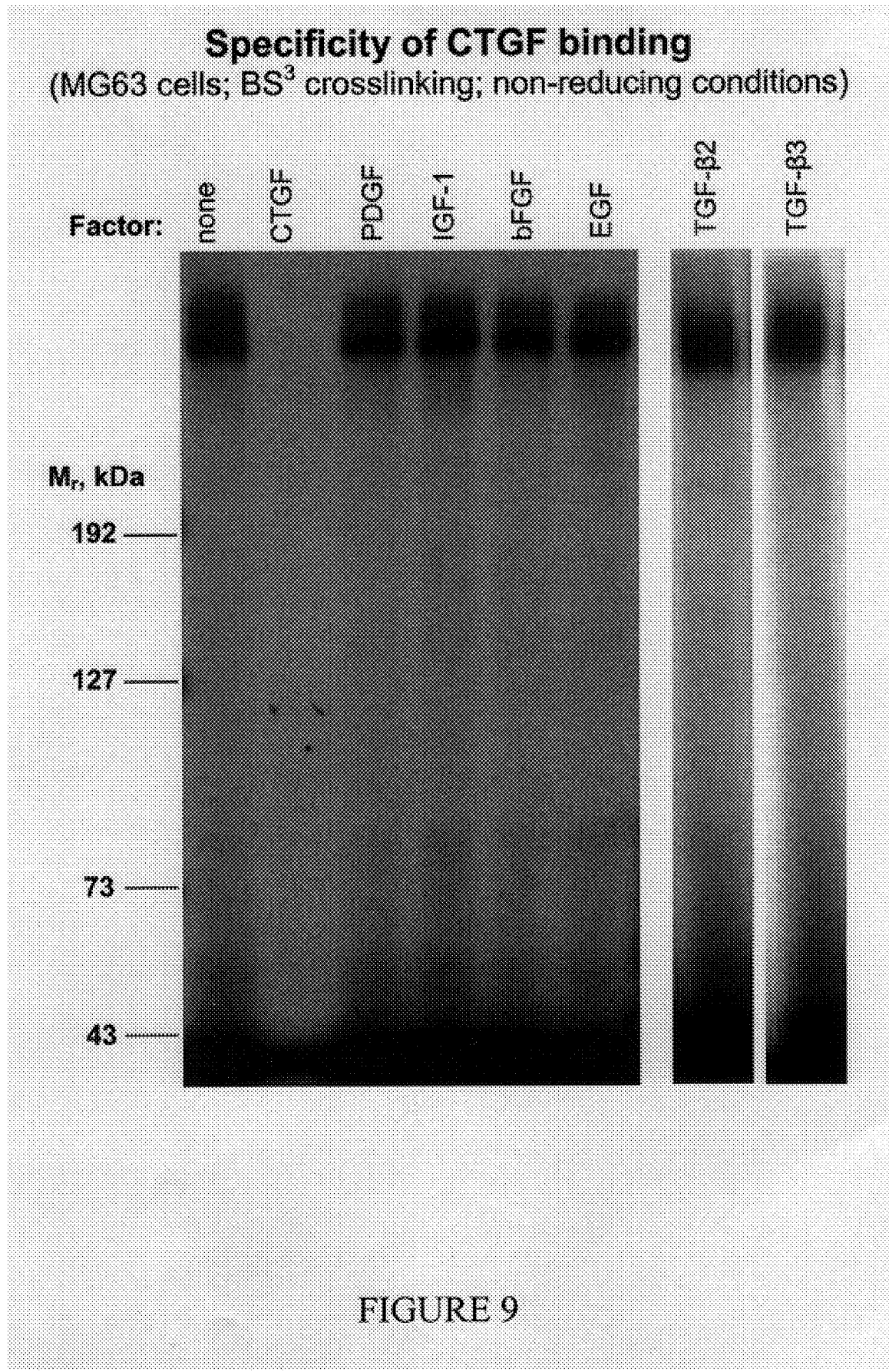
FIG. 9 sets forth equilibrium binding analysis data related to the specificity with which CTGF binds to the CTGF receptor, as compared to other growth factors.

The specificity of CTGF binding to the CTGF receptor was analyzed by performing an affinity binding experiment in the presence of a number of known growth factors. MG63 cells were labeled with 200 pM $^{125}$I-CTGF in the presence of the indicated growth factor at 1 μg/ml. The cells were cross-linked with S-SMCC and the cell lysates were reduced prior to SDS-PAGE. As set forth in FIG. 9, the only growth factor that effectively competed for CTGF binding to the cell surface was CTGF itself.

Example 9
Purification of CTGF Receptor

Figure 10A:
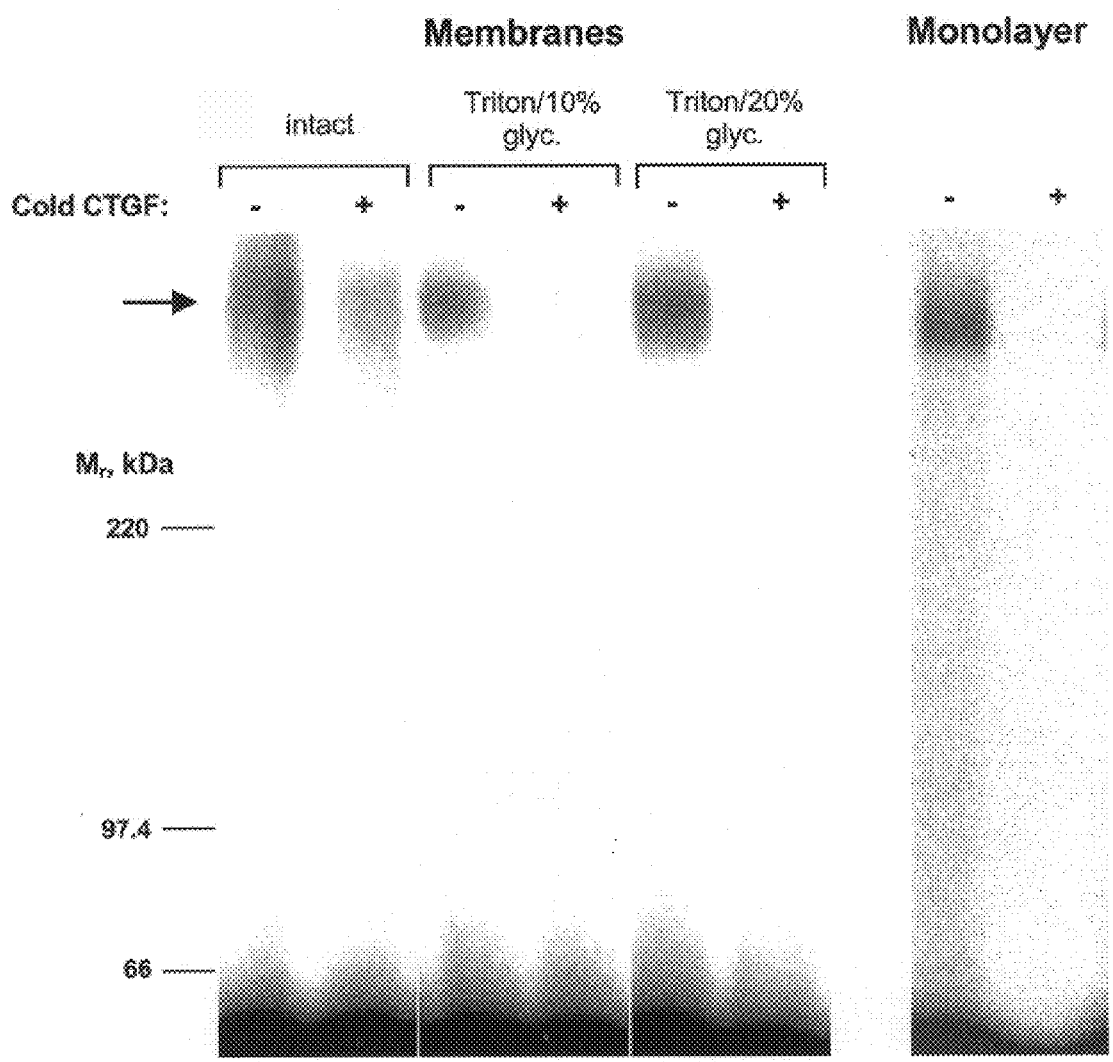
FIGS. 10A, 10B, and 10C set forth data relating to the affinity purification of the CTGF receptor.

In order to perform affinity purification of the receptor, it was necessary to determine conditions that would allow solubilization of the membrane proteins as described below as well as allow binding of the CTGF. Crude membranes were prepared from BMS-2 cells by a modification of the procedure reported by Atkinson (Atkinson, 1973, in Methods in Cell Biology, Prescott, ed, Vol. VII, pp.157–188, Academic Press, New York) . A panel of receptor-grade detergents (Boehringer Mannheim) was used to solubilize the proteins. The proteins were incubated with 0.2 nM $^{125}$I-CTGF in the presence or absence of a 200-fold excess unlabeled CTGF. The samples were cross-linked with BS$^3$, then separated by 5% SDS-PAGE. Under these conditions, complexes of CTGF cross-linked to the high $M_r$ protein could not be detected. The assay was repeated with 1% Triton X-100 (receptor grade, Boehringer Mannheim) to which glycerol was added to stabilize the membrane proteins. The results are shown in FIG. 10A. The left panel demonstrates CTGF binding to intact membrane fragments; the addition of 10% and 20% glycerol to solubilized membranes gave similar binding results, with 20% glycerol being slightly more favorable. These conditions were adapted for an affinity purification protocol. Molecular size markers in kDa are indicated at the left of the figure.

Crude membrane preparations were prepared from monolayer cultures of BMS-2 cells by a modification of the procedure reported by Atkinson. Cells were cultured in roller bottles and detached with 5 mM EDTA in Dulbecco's PBS lacking calcium and magnesium (Gibco BRL). The cells were washed, then suspended in hypotonic phosphate buffer, 7.5 mM NaPO$_4$, pH 7.2, and incubated for 10 minutes on ice. The membranes were disrupted by sonication, and the nuclei were stabilized in 10 mM NaPO$_4$, pH 7.2, 10 mM NaCl, 3 MM MgCl$_2$. The nuclei and whole cells were removed by centrifugation at 800×g, and the supernatant was collected. The supernatant was centrifuged over a cushion of 45% sucrose in Dulbecco's PBS, pH 7.2 for one hour at a rate of 24,000×g. The membrane fraction located at the sucrose/PBS interface was carefully collected, diluted, and concentrated by centrifugation at a rate of 100,000×g for 15 minutes. The membrane pellet was resuspended in Dulbecco's PBS and protein content was estimated with BCA reagent (Pierce Chemical Co.) against an albumin standard.

Figure 10B:
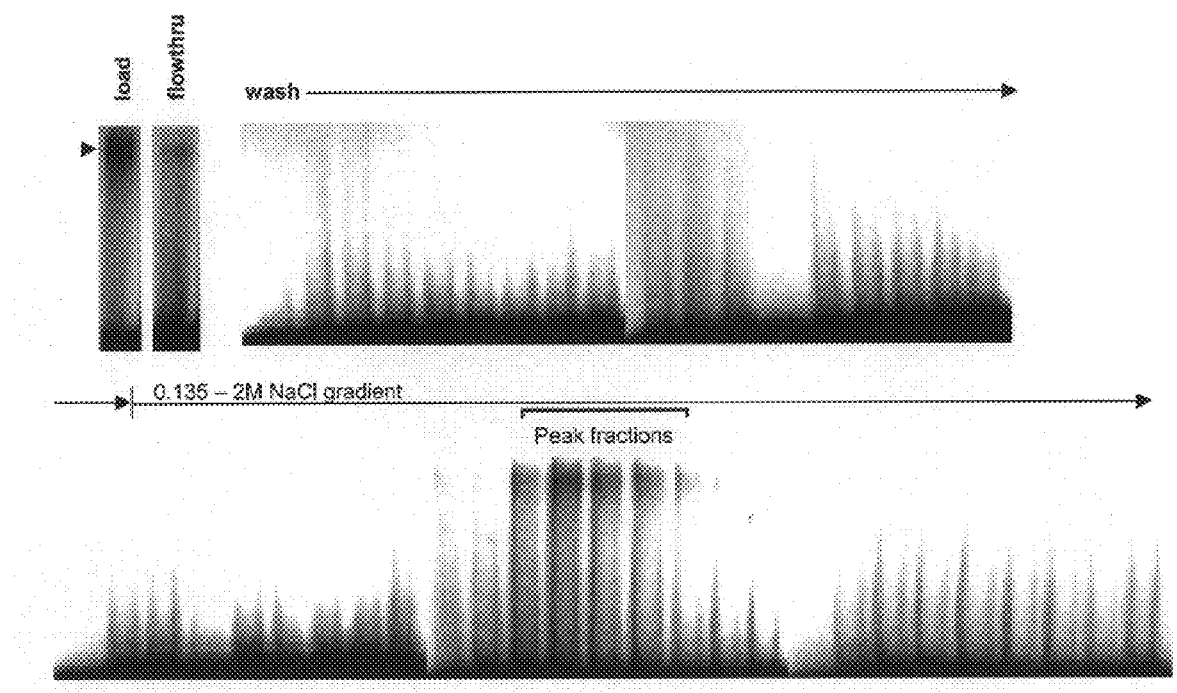
Figure 10C:
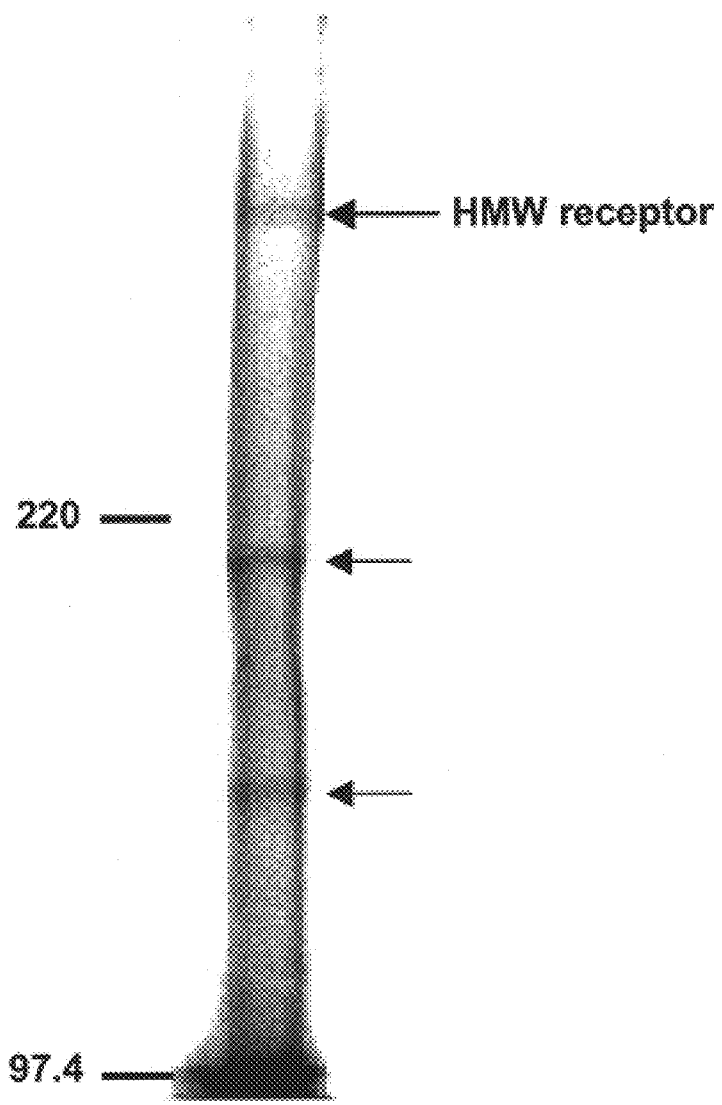

The membranes were solubilized in 1% Triton, 20% glycerol, in PBS (Buffer A) containing a cocktail of protease inhibitors (Calbiochem or Boehringer) and applied to rhCTGF coupled to Reactigel GF-2000 (Pierce Chemical Co.). The flow-through was collected and the column was washed with 20 column volumes of Buffer A. The bound sample was eluted with a gradient of 0.135–2M NaCl in 1% Triton, 20% glycerol, PBS. An aliquot of each fractions was analyzed by binding with CTGF, cross-linking with BS$^3$, and separation by 5% SDS-PAGE. The results are shown in FIG. 10B. The load and flow-through fractions refer to aliquots reserved from the loaded sample and flow-through for binding analysis. Peak fractions are indicated with a bracket. The peak fractions determined by binding analysis were pooled and separated on 5% SDS-PAGE. The gel was stained with Coomassie (FIG. 10C) and the protein migrating at the expected mass region of the gel was excised for analysis by mass spectroscopy.

Example 10
Sequence Analysis Revealed that LRP is the Receptor for CTGF

The CTGF receptor was isolated and purified by affinity chromatography as described above. The gel band of interest was excised with a clean razor blade, destained, and subjected to trypsinization. The recovered peptide fragments were analyzed by liquid chromatography and two rounds of mass spectroscopy. Microelectrospray columns of 360 m o.d.×100 m i.d. fused silica capillary were packed with 10 to 12 cm of PerSeptive Biosystems (Framingham, Mass.) POROS 10R2, a reversed phase packing material. The flow rate from the HPLC pump (typically 150 l/min) was split pre-column to achieve a flow rate of 500 nl/min. The mobile phase for the gradient elution consisted of (A) 0.5% acetic acid and (B) acetonitrile/water 80:20 (v/v) containing 0.5% acetic acid. The gradient was linear from 0 to 60% B in 30 minutes.

Mass spectra were recorded on an LCQ ion trap mass spectrometer (Finnigan MAT, San Jose, Calif.) equipped with a microelectrospray ionization source. Tandem mass spectra were acquired during the entire gradient automatically. Protein sequence databases were searched with the tandem mass spectra using the computer program SEQUEST (Eng et al., 1994, J Am Soc Mass Spectrom, 5:976–989). SEQUEST correlates tandem mass spectra of peptides with amino acid sequences from protein and nucleotide databases. The FBSC Non-Redundant Protein Database (NRP) database was obtained as an ASCII file in the FASTA format from Frederick Biomedical Supercomputing Center (ncbi.nlm.nih.gov in/pub/nrdb) by anonymous ftp. Each sequence produced by SEQUEST was verified by manually inspecting the fit of the amino acid sequence to the corresponding tandem mass spectrum.

The first round of mass spectroscopy yielded the following peptides:
AALSGANVLTLIEKDIR (SEQ ID NO: 1)
NAVVQGLEQPHGLVVHPLR (SEQ ID NO: 2)
SERPPIFEIR (SEQ ID NO: 3)
TVLWPNGLSLDIPAGR (SEQ ID NO: 4)
TTLLAGDIEHPR (SEQ ID NO: 5)
YVVISQGLDKPR (SEQ ID NO: 6)

The second round of mass spectroscopy yielded the following peptides:
DGILFWTDWDASLPR (SEQ ID NO: 7)
GWDTLYWTSYTTSTITR (SEQ ID NO: 8)
IFFSDIHFGNIQQINDDGSGR (SEQ ID NO: 9)
ILWIDAR (SEQ ID NO: 10)
ITWPNGLTVDYVTER (SEQ ID NO: 11)
NAVVQGLEQPHGLVVHPLR (SEQ ID NO: 12)
SERPPIFEIR (SEQ ID NO: 13)
TTLLAGDIEHPR (SEQ ID NO: 14)
TVLWPNGLSLDIPAGR (SEQ ID NO: 15)

These sequences were found to be present in the low density lipoprotein receptor-related protein (LRP), also known as the α2-macroglobulin receptor (α2MR).

Example 11
Cross-linking Analysis with Cells Deficient in LRP

Three cell lines useful for a complete genetic system for the study of LRP function were generated by Willnow and Herz (1994, J. Cell Sci. 103:719–726) and obtained from the American Type Culture Collection (ATCC). The wild type line, MEF1, are fibroblasts originating from murine embryos and are homozygous positive for LRP expression. Fibroblasts that carry one or two copies of the defective LRP allele from hybrid embryos (see Herz et al.(1992) Cell. 71:411–21) were cultured in Pseudomonas exotoxin A (PEA) and the resistant clones, PEA 10 and PEA 13, which are heterozygous and homozygous, respectively, for LRP deficiency. Resistance to Pseudomonas exotoxin A by PEA 10 and PEA 13 cell lines, as well as sensitivity by MEF1 cells, was confirmed by growth in 30 ng/ml Pseudomonas exotoxin A after receipt from ATCC.

The three cell lines were cultured and plated for affinity binding with radiolabeled CTGF, cross-linking and gel analysis. Specifically, cross-linking of $^{125}$I-rhCTGF to monolayers of MEF1, PEA 10 and PEA 13 cells were carried out as follows: Cells plated in 6-well dishes were incubated at 4° C. with 0.2 nM $^{125}$I-rhCTGF in the presence (+) or absence (−) of a 200 fold excess of unlabeled rhCTGF in a binding buffer of PBS, 0.2% BSA, 0.02% sodium azide. After a 3 hour period of labeling, cells were cross-linked with 0.5 mM BS$^3$ for 15 minutes at room temperature. The cross-linking agent was removed and the cells were washed 3 times with 250 mM sucrose, 10 mM Tris pH 7.5, 10 mM EDTA. The cell surface proteins were extracted with 1% Triton in 10 mM Tris pH 7.5 with protease inhibitors, then applied to 5% SDS-PAGE. A positive control of MG63 human osteosarcoma cells were labeled and run on the gel for reference. The gel was dried, exposed to film, and processed for autoradiography. The MEF and PEA lanes were exposed for 17 hours; the MG63 lanes were exposed for 1 hour.

Figure 11:
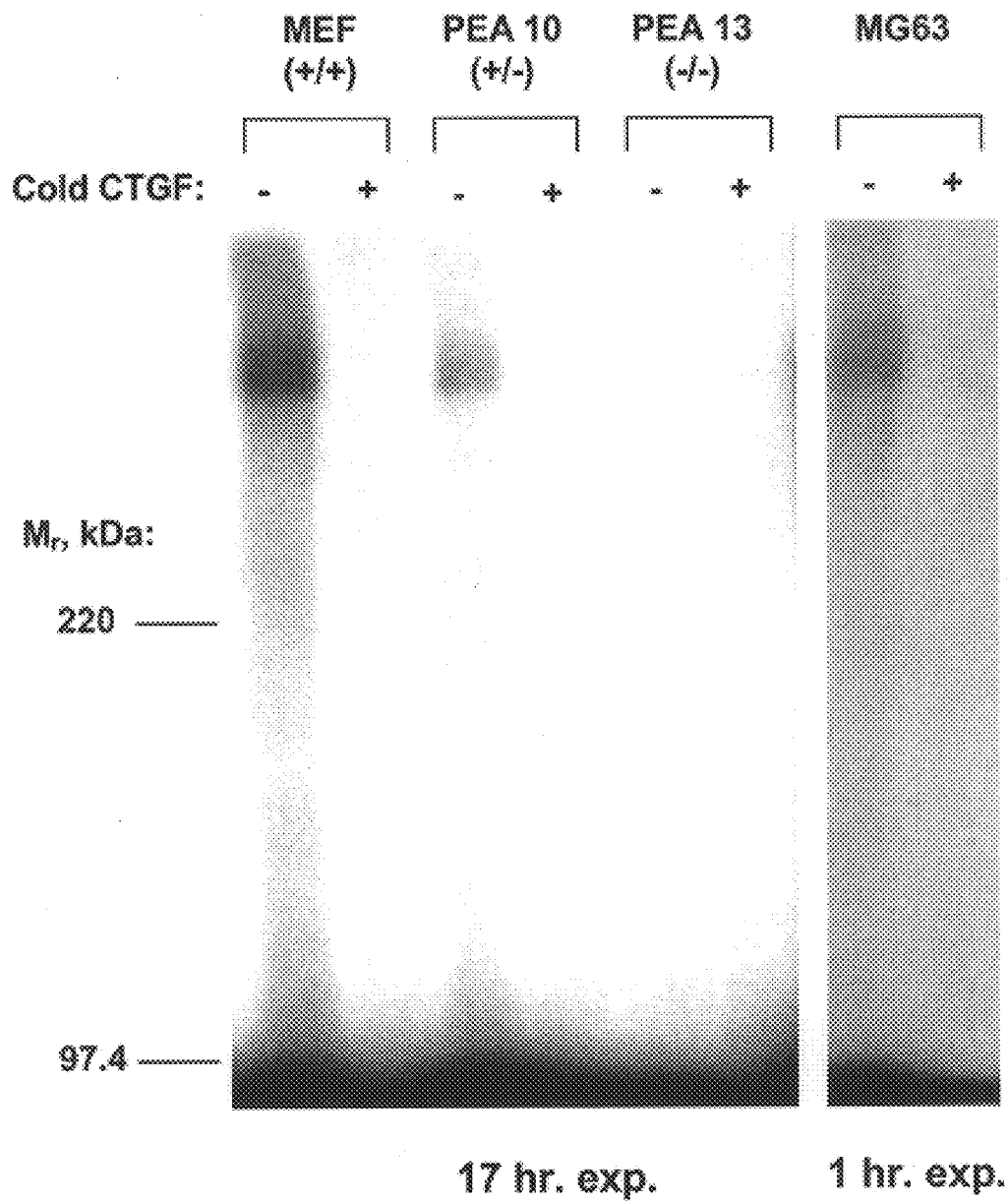
FIG. 11 sets forth data resulting from the cross-linking of $^{125}$I-CTGF to monolayers of MEF1, PEA 10, and PEA 13 cells.

The results are shown in FIG. 11. Even with overexposure of the autoradiograph, no signal co-migrating with the complex was observed in the lanes containing PEA 13 cells, showing that LRP deficiency is equivalent to deficiency of the CTGF receptor. Non-linear regression analysis of equilibrium binding experimental data performed on these cells showed that there were about 5-fold more CTGF binding sites on MEF1 cells than on PEA 10 cells, and no binding was detected on PEA 13 cells. Binding affinities with a calculated $K_d$ of 1 to 5 nM were determined.

Example 12
Immunoprecipitation of CTGF/CTGF Receptor Complex with LRP Monoclonal Antibodies Cross-linking analysis of CTGF with the family of LRP genetically manipulated cells indicated that CTGF bound to a protein that was present in the wild type cells and was less available or absent in the mutant cells. To test more specfically whether CTGF bound to LRP, monoclonal antibodies against both the alpha-chain (515 kDa subunit) and the beta-chain (85 kDa, membrane spanning subunit) of LRP were used (American Diagnostica, Inc.).

Immunoprecipitation of $^{125}$I-CTGF receptor complexes with LRP antibodies were conducted as follows: MG63 human osteosarcoma cells were affinity labeled and cross-linked with 0.2 nM $^{125}$I-CTGF. The complexes were extracted with 1% Triton in 10 mM Tris pH 7.5 and incubated for 20 minutes at 4° C. with 1 µg of purified IgG prepared against the alpha-chain or the beta-chain of LRP (American Diagnostica, Inc.). A separate sample was incubated with 1 µg nonimmune murine IgG, and a fourth sample was saved as untreated ("pre-precipitation") material. The samples were then incubated overnight with Protein G-Sepharose beads (Pharmacia). Following incubation, the precipitation samples were washed four times with 1% Triton, 10 mM Tris pH 7.5, 10 mM EDTA and the G-Sepharose bound samples were released with SDS-PAGE buffer and boiling. The samples were applied to 5% SDS-PAGE and the gel was dried and exposed to film for autoradiography.

Figure 12:
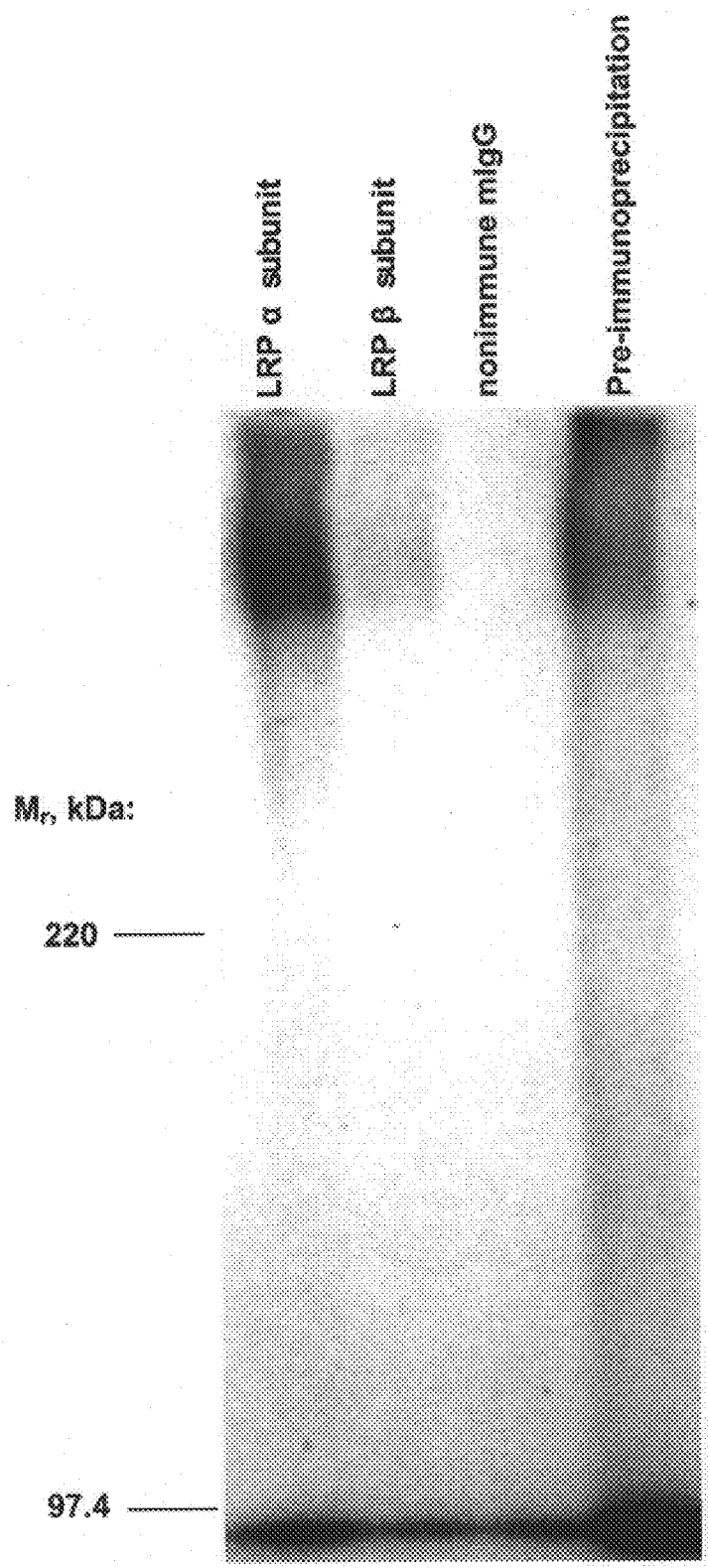
FIG. 12 sets forth data resulting from the immunoprecipitation of $^{125}$I-CTGF/CTGF receptor complexes with LRP/α2MR antibodies.

As shown in FIG. 12, the alpha-chain antibody effectively precipitated the CTGF-high relative molecular mass ($M_r$) complex. The beta-chain antibody reacted weakly with the complex, as only a trace amount of immuno-precipitable binding was observed in the high $M_r$ region of the gel. Nonimmune IgG was unreactive, as there was no apparent precipitation with the complex. These results strongly suggested that CTGF interacted with a protein that shares immuno-crossreactivity with LRP.

Example 13
LRP Ligands Competitively Inhibit CTGF Binding the CTGF Receptor

Figure 13:
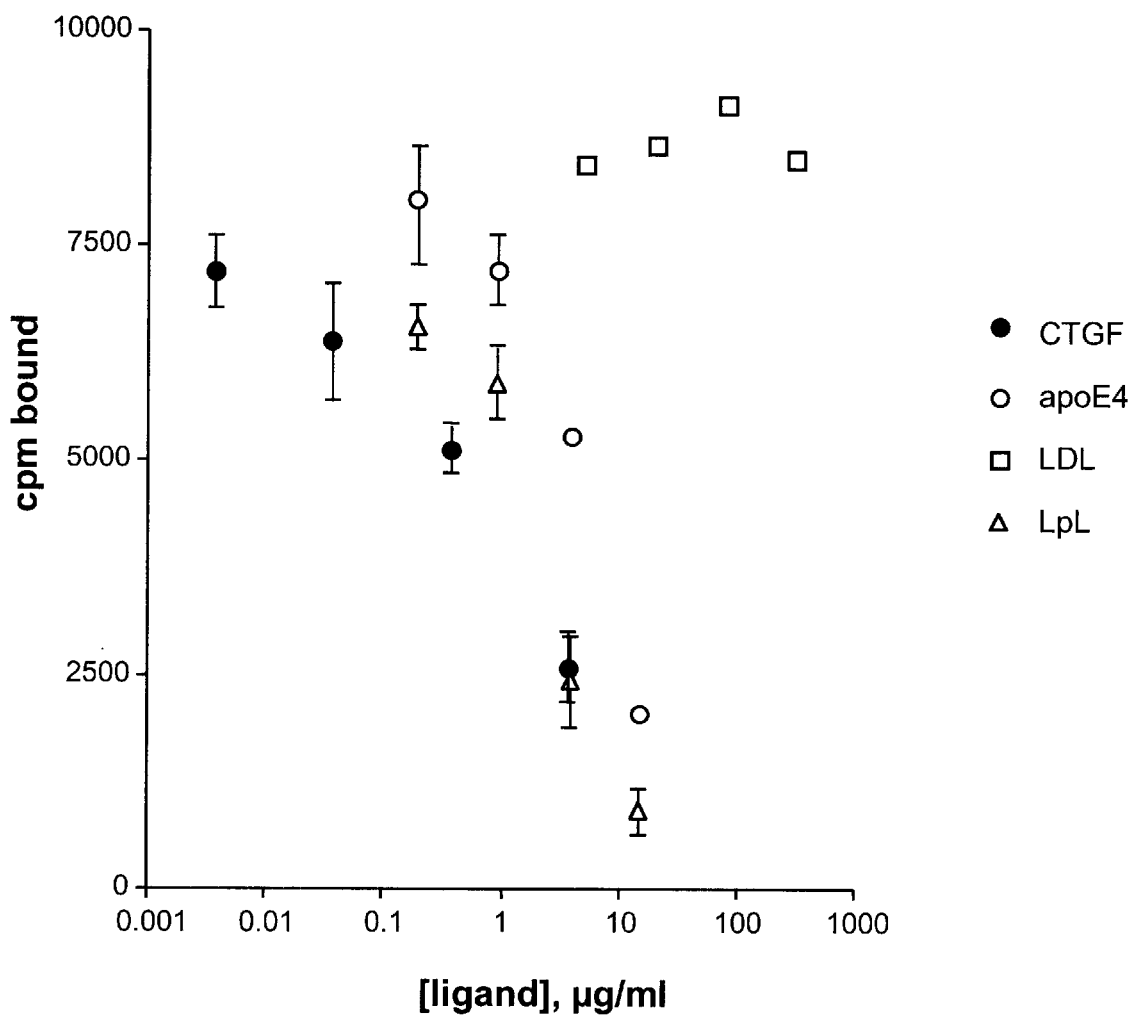
FIG. 13 sets forth data relating to binding analysis of $^{125}$I-CTGF competition with LRP/α2MR ligands.

As depicted in FIG. 13, binding analysis showed $^{125}$I-CTGF competition with LRP ligands. BMS-2 cells were incubated with 0.1 nM $^{125}$I-CTGF in the presence of unlabeled CTGF, recombinant human apoE, low density lipoprotein purified from human plasma (LDL), or lipoprotein lipase purified from bovine milk (LpL). Both apoE and LpL competed with $^{125}$I-CTGF, suggesting that they were alterative ligands for the high $M_r$ CTGF binding protein.

Figure 14:
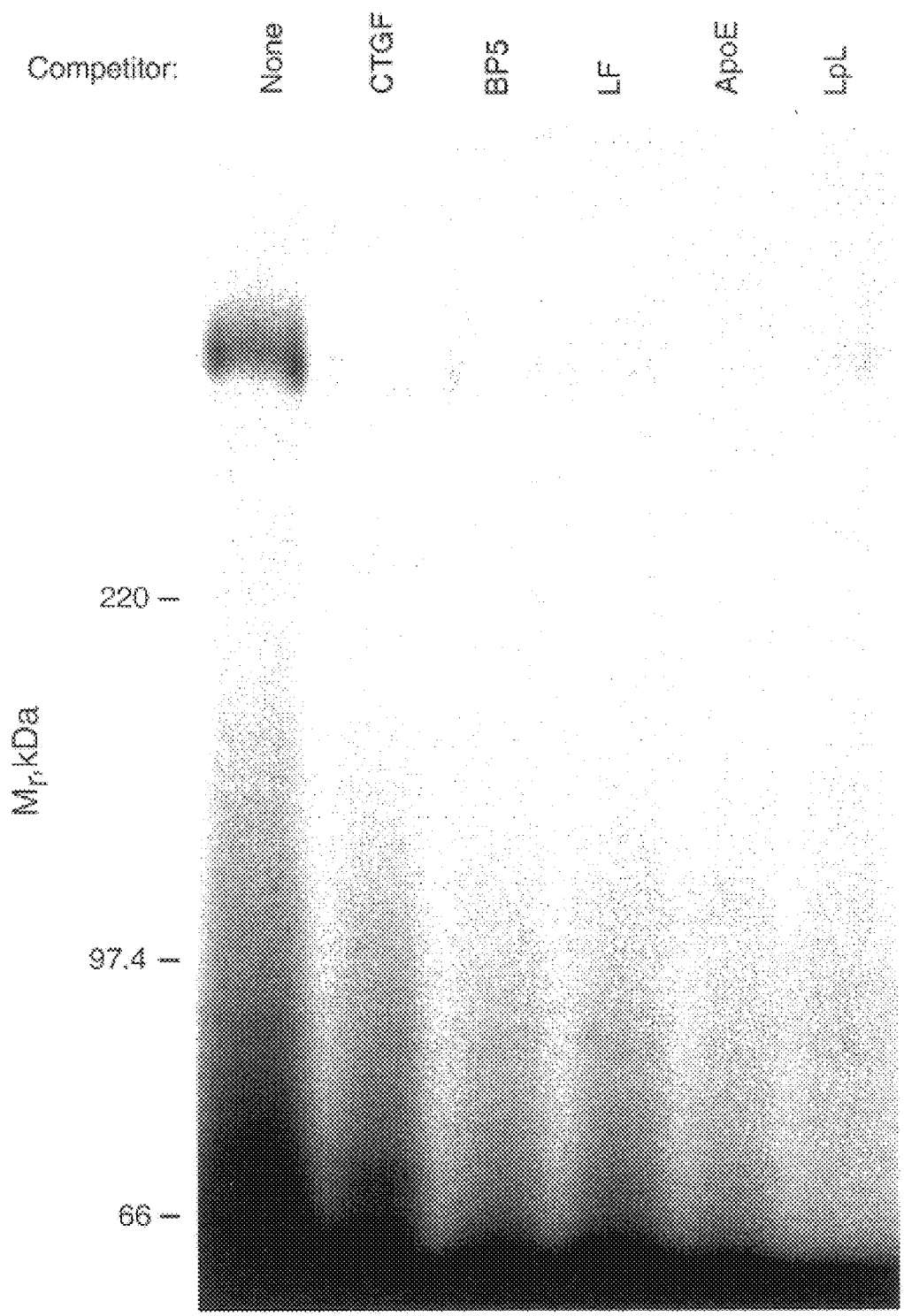
FIG. 14 sets forth data relating to competitive binding and cross-linking of various ligands, including CTGF, with LRP.
Figure 15:
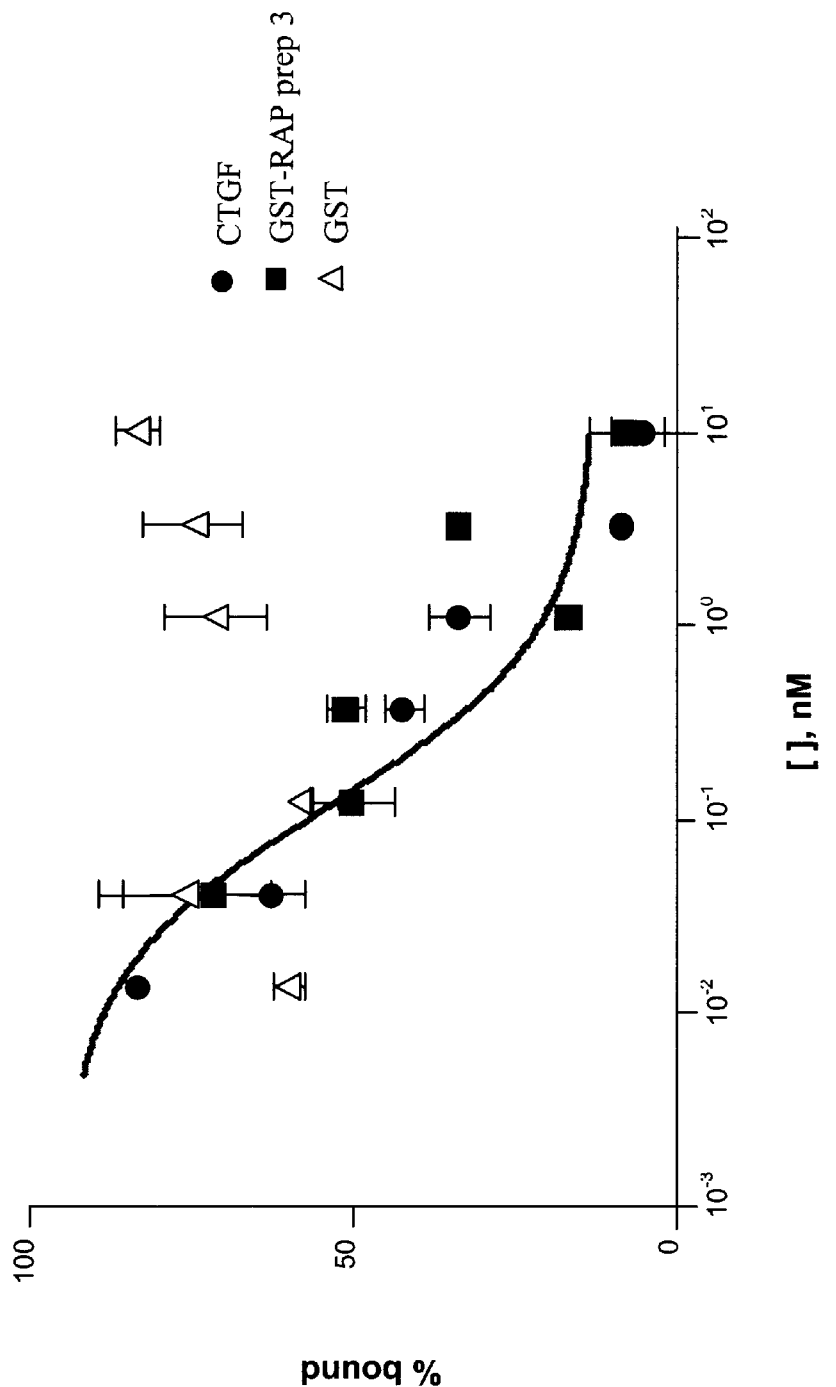
FIG. 15 sets forth data relating to binding competition studies of CTGF and Receptor Associated Protein (RAP).

To examine whether ligands known to bind to LRP inhibit CTGF binding, BMS-2 cells were labeled with 50 pM $^{125}$I-CTGF in the presence or absence of unlabeled ligand (CTGF: 21.5 nM; BP5$^{201-218}$: 50 µg/ml or 85 nM (Campbell and Andress, 1997, Am. J. Physiol., 273:E1005–13); lactoferrin (LF): 25 µg/ml or 250 nM; apo E: 20 µg/ml or 574 nM; lipoprotein lipase (LpL): 20 µg/ml or 400 nM). The cells were cross-linked and the receptor complexes were solubilized, processed on SDS-PAGE and visualized by autoradiography. As shown in FIG. 14, the ligands were very effective in competing the binding to the LRP receptor; however, CTGF was most effective, as a trace amount of binding was observed for all alternative ligands. Additionally, the saturation of the LRP receptor with these ligands did not demonstrate binding of CTGF to any other sized proteins.

In a further study, receptor associated protein (RAP), a known inhibitor of ligand binding to LRP, was prepared. Plasmid DNA containing the human RAP cDNA sequence was obtained (ATCC as the I.M.A.G.E. Consortium Clone ID 511113, Lennon et al., 1996, Genomics, 33:151–152). The RAP sequence was sub-cloned into the pGEX4T-1 vector (Pharmacia) for the synthesis of a RAP-GST (glutathione S-transferase) fusion protein in E. coli. The fusion protein was purified over glutathione-Sepharose as described (Warshawsky et al., 1993, J. Biol. Chem., 268:22046–22054), and tested as a competitor of CTGF binding. In a binding experiment on BMS-2 cells (FIG. 16), it was observed that RAP-GST was able to compete for CTGF binding to LRP. The GST protein by itself had no competitive activity. These results demonstrate that RAP would be a useful antagonist for CTGF binding to the CTGF receptor.

Taken together with the mass spectrometry data, cross-linking analysis with LRP deficient cells, and competition of CTGF binding with many LRP/α2MR ligands, these results confirmed that LRP is a binding receptor for CTGF.

Example 14
Antibodies to LRP Competitively Inhibit CTGF Binding to the CTGF Receptor A number of antibodies to LRP were evaluated for their ability to inhibit binding of $^{125}$I-CTGF to MG63 cells. Information about the antibodies is summarized in Table 2 as follows.

TABLE 2

| ANTIBODY NAME | SOURCE | TYPE | EPITOPE |
|---|---|---|---|
| Cat. No. 3402 | American Diagnostica | mAb, IgG$_1$ | Alpha chain of LRP; recognizes human LRP only |
| Cat. No. 3501 | American Diagnostica | mAb, IgG$_1$ | Beta chain of LRP; aa 4291–4344, the EGF repeat close to the membrane spanning segment; recognizes human and rat LRP |
| Cat. No. 11H4 | ATCC | mAb, IgG$_1$ | 13 COOH-terminal amino acids; recognizes rodent and human LRP |
| p129 | QCB | Rabbit polyclonal | aa 3925–3939 (human alpha chain) |
| p130 | QCB | Rabbit polyclonal | aa 4528–4544 (human beta chain, intracellular domain) |

Figure 16:
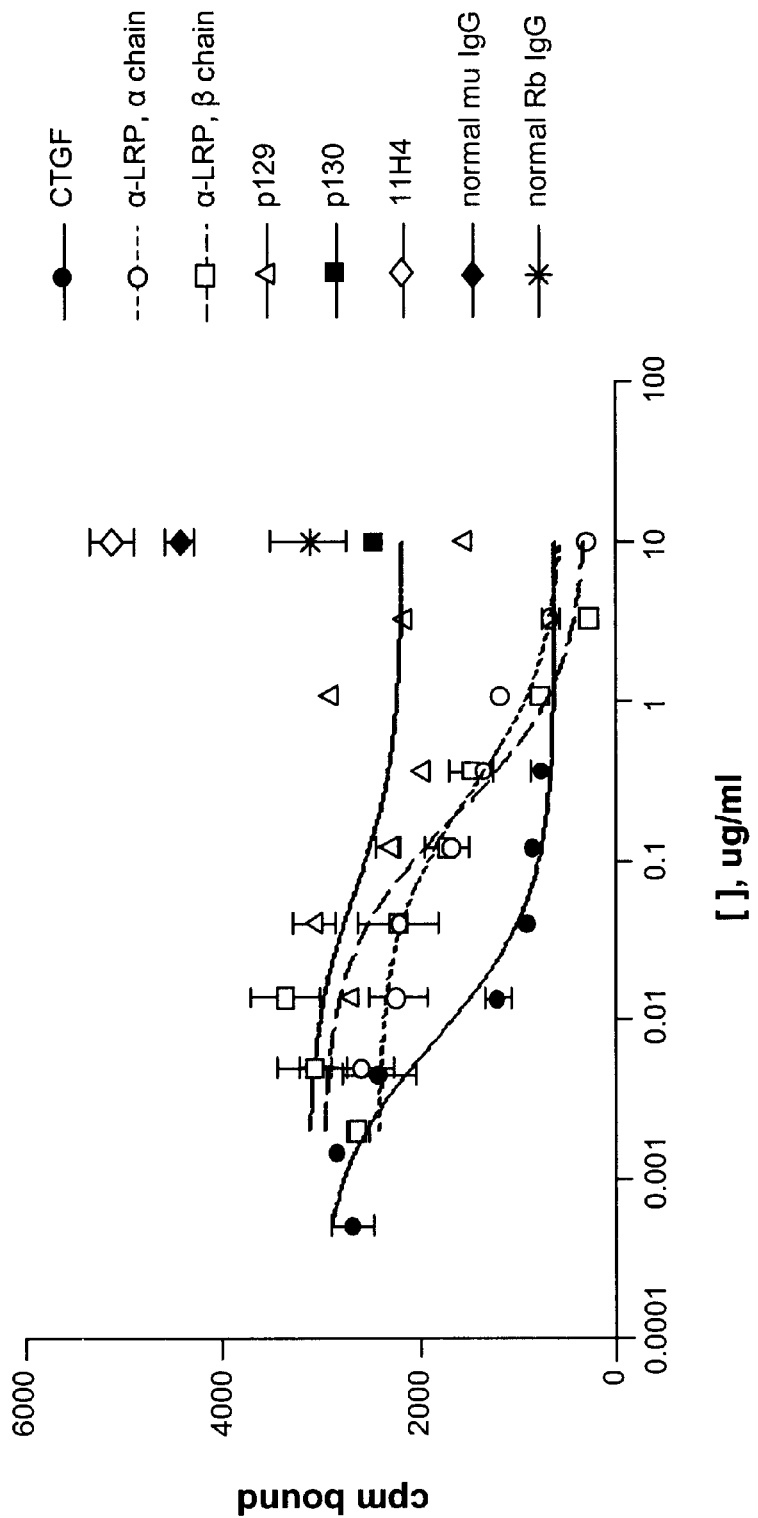
FIG. 16 sets forth data relating to competitive inhibition of $^{125}$I-CTGF binding with LRP specific antibodies.

The MG63 cell line of human osteosarcoma cells was used for binding studies due to the human specific immunoreactivity of some of the antibodies. Cells were incubated with 0.2 nM $^{125}$I-CTGF in the presence of the indicated concentrations of antibody or cold CTGF for 4 hours. The cells were washed to remove the unbound ligands, lysed with Triton X-100 and the bound material was counted. The results are shown in FIG. 16.

The antibodies purchased from American Diagnostica (3402 and 3501) neutralized the binding of CTGF to MG63 cells. Both alpha and beta antibodies inhibited the binding with similar parameters. The p129 polyclonal antibody displayed slight inhibition of binding, but since this antibody was made against a peptide sequence, one would not expect that it would have high reactivity toward the native protein. The p130 antibody was not expected to have neutralizing activity, as it would recognize an intracellular domain. The description of 11H4 (from ATCC) suggested that it too, recognizes an intracellular domain.

Example 15
LRP Functions to Internalize and Degrade CTGF

Experiments were performed in which the internalization and degradation kinetics of CTGF were followed in the presence or absence of a known LRP ligand, lactoferrin. Kinetics were followed in the presence or absence of 3 μg/ml heparin or lactoferrin. $^{125}$I-CTGF was bound to MG63 cells at 4° C. and free CTGF was removed by washing the cells. Fresh medium was placed on the cells, and the cells were transferred to 37° C. At each time point, the medium was removed and TCA precipitated. Degraded $^{125}$I-CTGF was quantified by measuring the cpm in the non-precipitable fraction (see FIG. 17). In parallel experiments, $^{125}$I-CTGF was bound to MG63 cells at 4° C. and free CTGF was removed by washing the cells. Fresh medium was placed on the cells, and they were transferred to 37° C. At each time point, the cell layer was removed by extensive trypsinization at 4° C. The cells were centrifuged and the cpm associated with the pellet, the internalized fraction, was determined (see FIG. 18).

Figure 17:
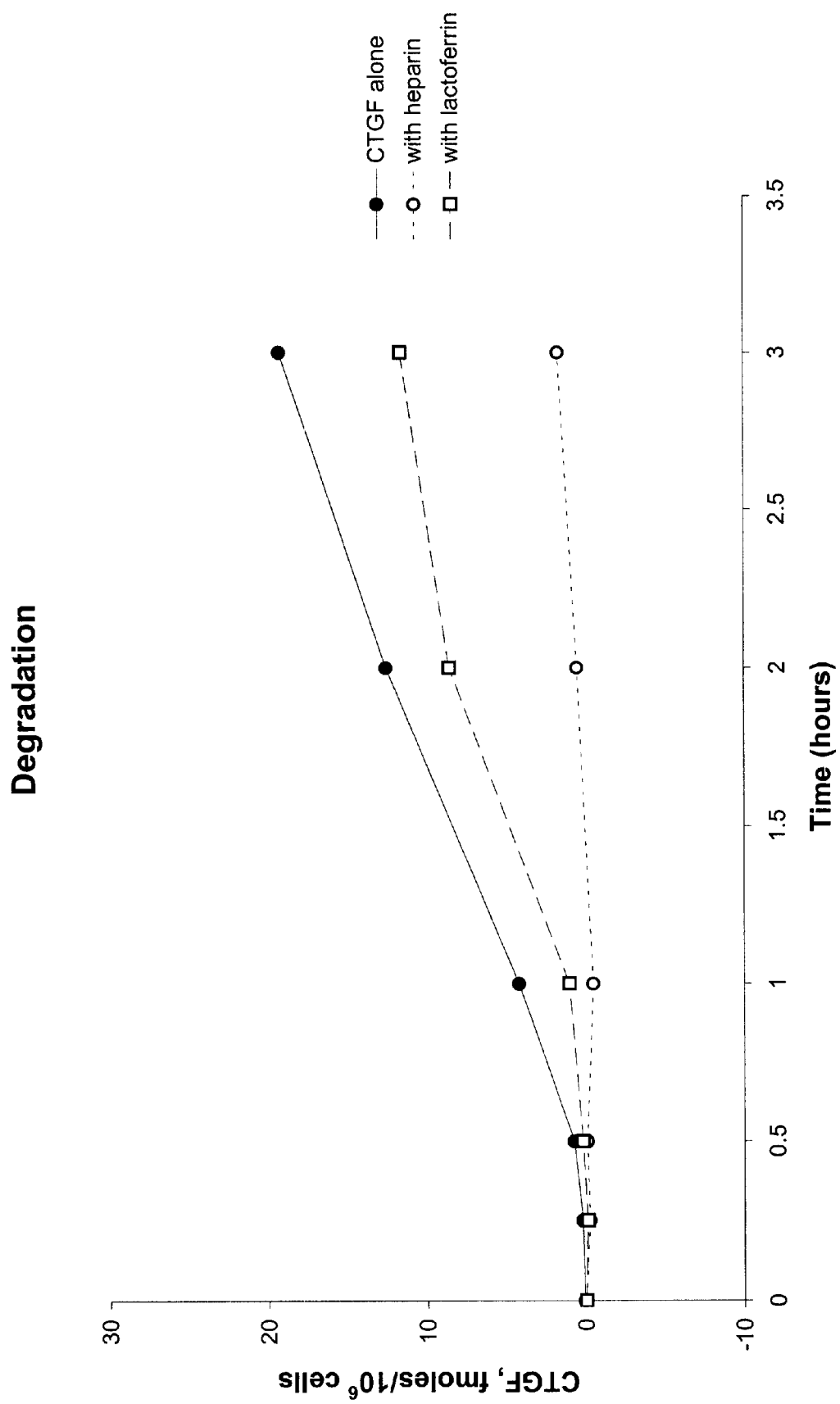
FIG. 17 and FIG. 18 set forth data relating to internalization and degradation of CTGF by LRP.
Figure 18:
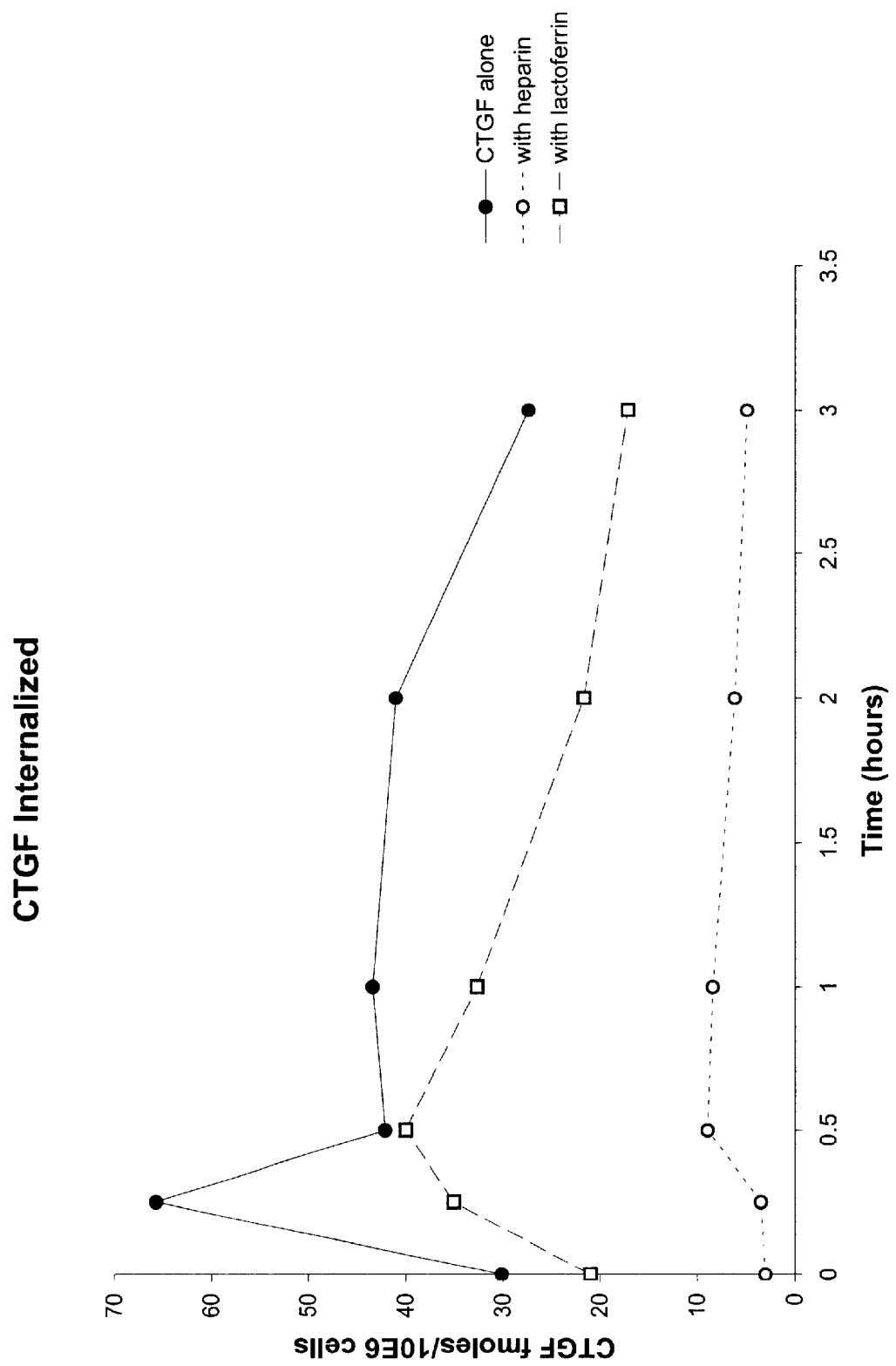
Figure 19A:
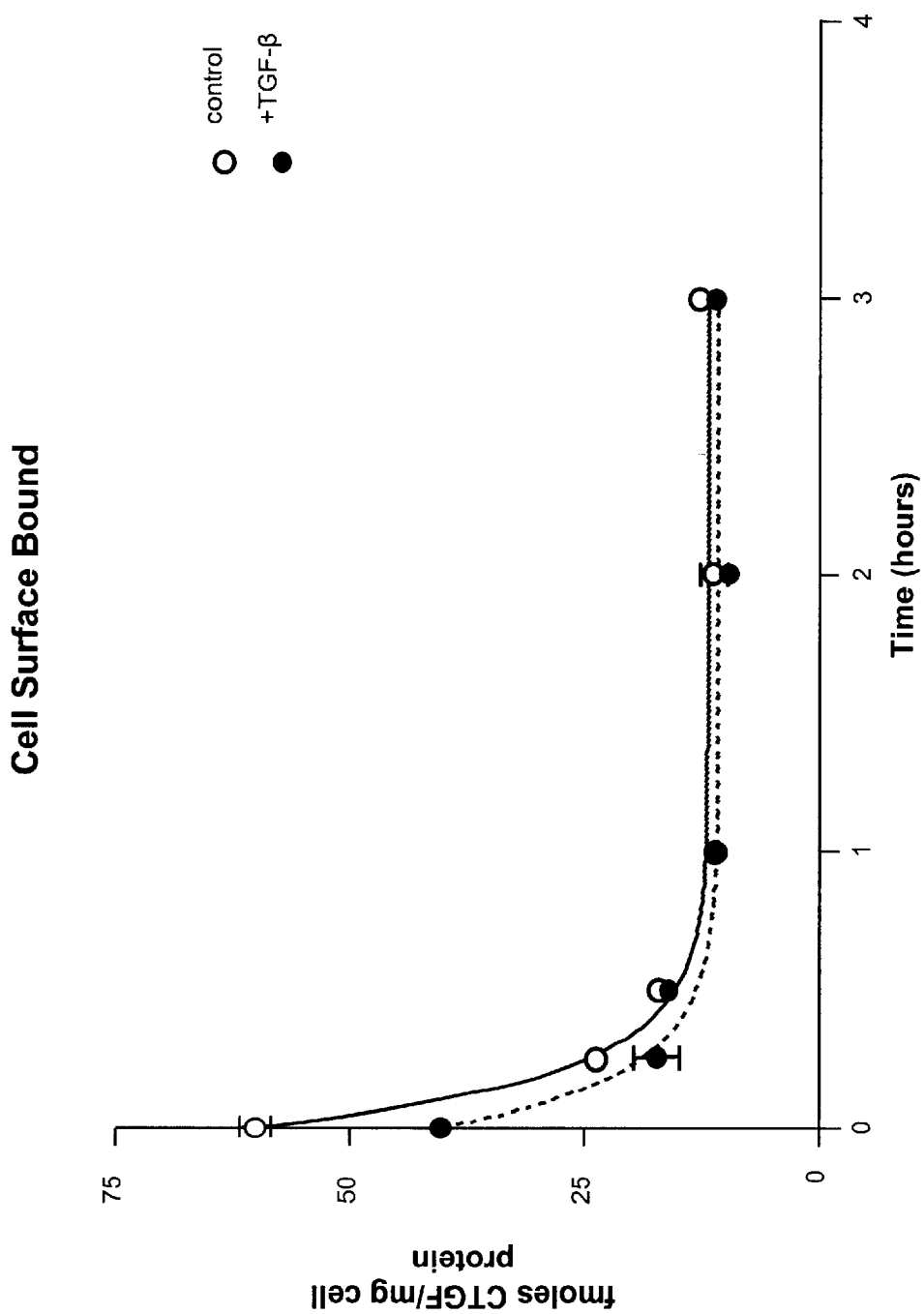
FIGS. 19A, 19B, 19C, and 19D set forth data relating to internalization kinetics of CTGF after TGF-β treatment for 48 hours.
Figure 19B:
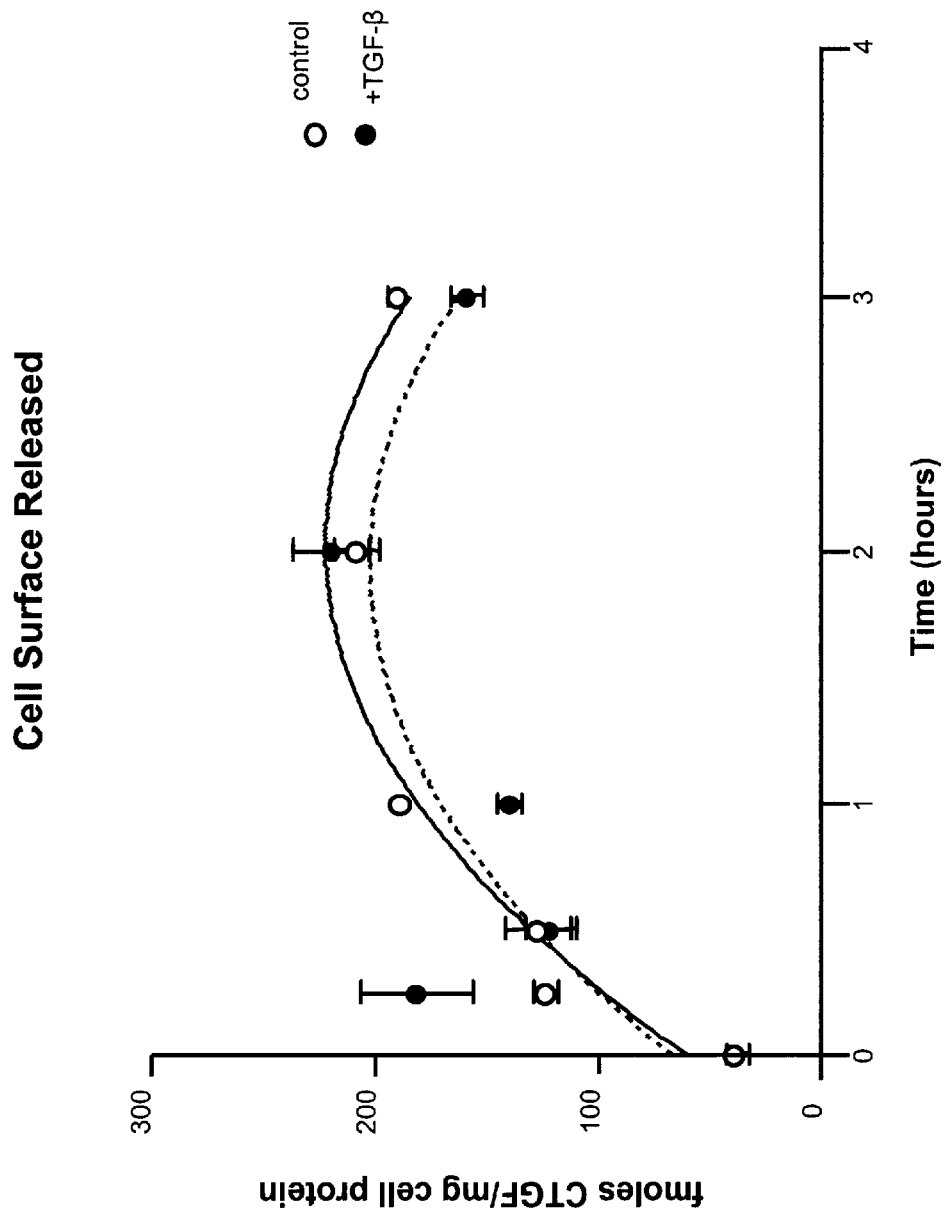
Figure 19C:
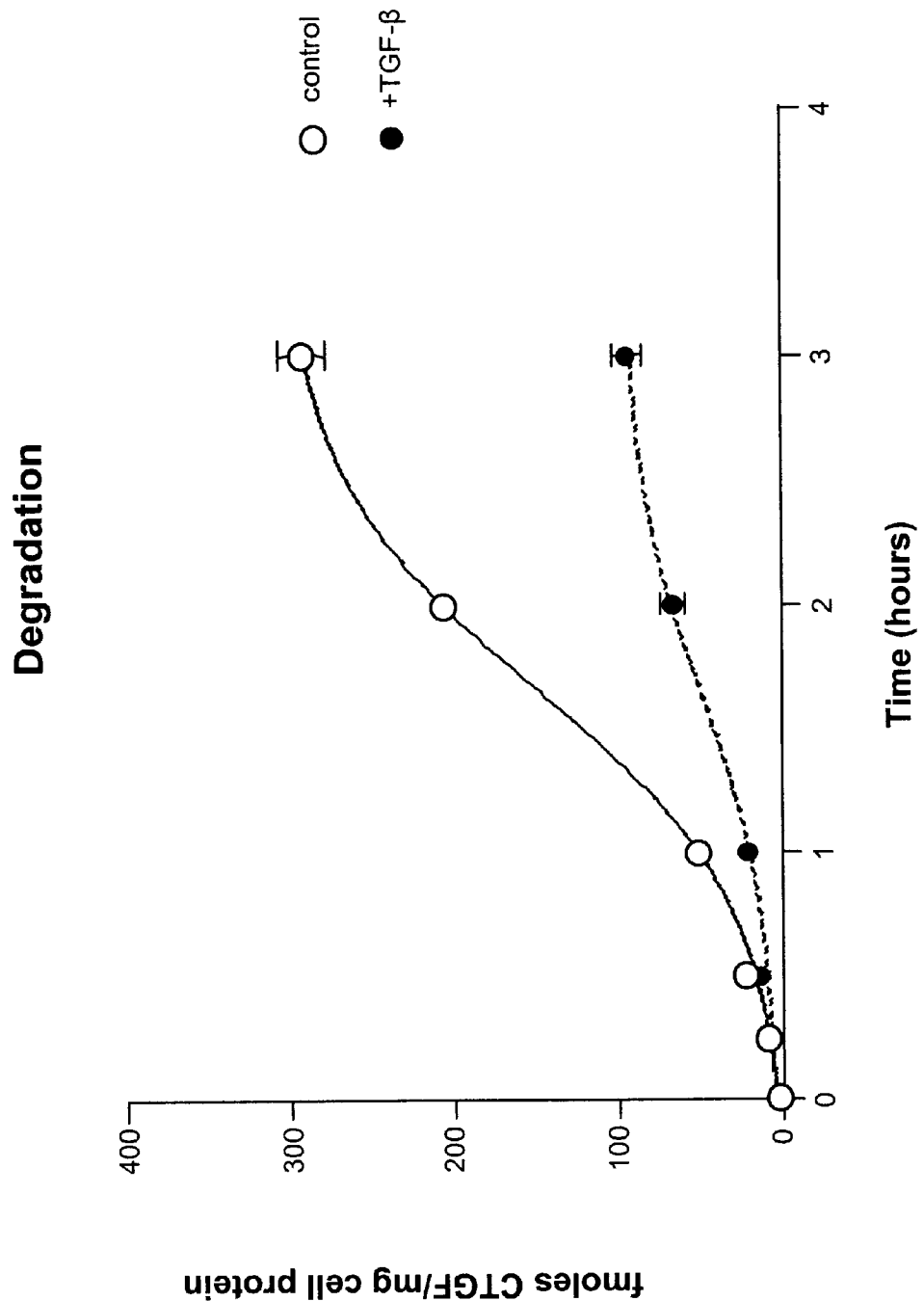
Figure 19D:
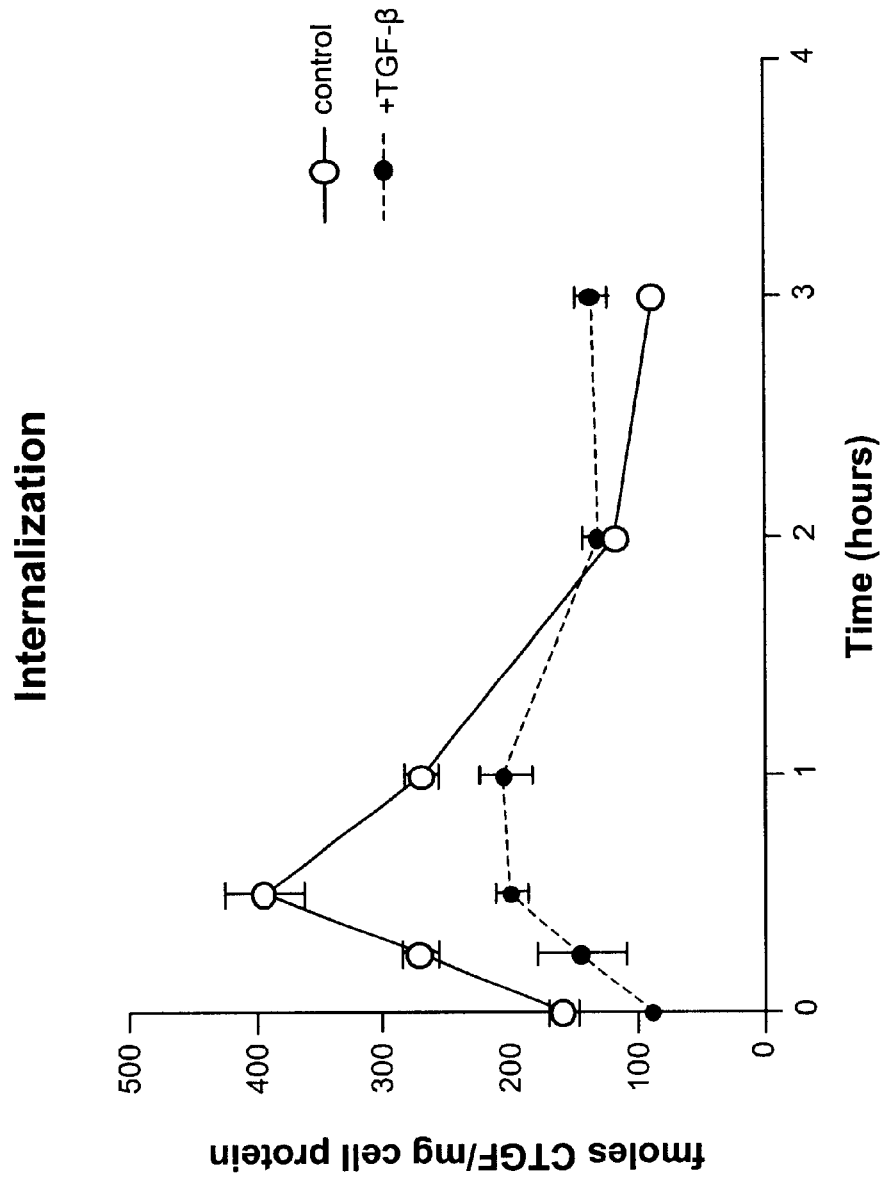

As shown by FIGS. 17 and 18, internalization was rapid, within 30 minutes, as has been described for other LRP ligands. (See, e.g., Kounnas, M. Z. et al. (1996) *J. Biol. Chem.* 271:6523–6529.; Casslén, B. et al. (1998) *Mol. Hum. Reprod.* 4:585–593; Mikhailenko, I. et al. (1 995) *J. Biol. Chem.* 270:9543–549; and Mikhailenko, I. et al. (1997) *J. Biol. Chem.* 272:6784–6791.) Heparin decreases both degradation and internalization of CTGF. Both lactoferrin and heparin reduced the rate of both degradation and internalization, consistent with previous reports that they are ligands for LRP. This competition and the kinetics of internalization demonstrated that CTGF is internalized by an LRP dependant mechanism.

Example 16
TGF-β Decreases the Rate of Internalization/Degradation of CTGF Through LRP To examine whether LRP function was altered by TGF-β treatment, the following experiments were conducted. MG63 cells were plated at 2.5×10$^4$ cells/cm$^2$ in MEM with 10% FBS. The following day, the cells were rinsed with MEM containing 0.5% MEM and incubated in this low serum medium with or without 20 ng/ml of TGF-β2. At 24 or 48 hours the cells were rinsed twice with binding medium, then incubated at 4° C. for 3 hours with 0.2 nM $^{125}$I-rhCTGF. After incubation, the cells were rinsed 4 times with binding buffer at 4° C., then fresh binding buffer pre-warmed to 37° C. was added and the cells continued incubation at 37° C. At time points of 0, 15, 30, 60, 120 and 180 min, the media were collected and processed by precipitation with 10% TCA. The cell layer was processed by trypsination of the cells. Pellets and supernatants were separated and counted for each point.

The results of a 48 hour exposure to TGF-β are set forth in FIGS. 19A, 19B, 19C, and 19D. Corresponding results were observed with 24 hour exposure to TGF-β. The data indicate a rapid internalization for control cells (no TGF-β), while the TGF-β treated cells demonstrated a more modest internalization of CTGF. Likewise, degradation of $^{125}$I-CTGF was at least 3 fold higher in control cells, suggesting a dependence on internalization for eventual degradation. These data indicated that clearance of CTGF from the cell surface was modulated by TGF-β. These studies, therefore, revealed a new target of the TGF-β-treated-cell phenotype; in other words, a new target for the development of a therapeutic for the inhibition of fibrosis and other connective tissue diseases and disorders.

The above experimental results described a time course for internalization and degradation after equilibrium binding of CTGF had been established. Another experiment was performed in which the internalization and degradation of CTGF was followed during the time course of binding to the cells. Various additives were included in the binding medium to examine the effect(s) and specificity of CTGF binding and internalization through LRP. These additives are set forth in Table 3 as follows:

TABLE 3

| ADDITIVE | PURPOSE |
|---|---|
| Cold CTGF | Differentiates specific CTGF binding |
| Chloroquin | Raises pH of endosome, inhibiting release/degradation |
| Chymostatin | Inhibitor of extracellular chymotryptic proteases |
| RAP (added as GST-RAP fusion protein) | Specific ligand for LRP |

Figure 20A:
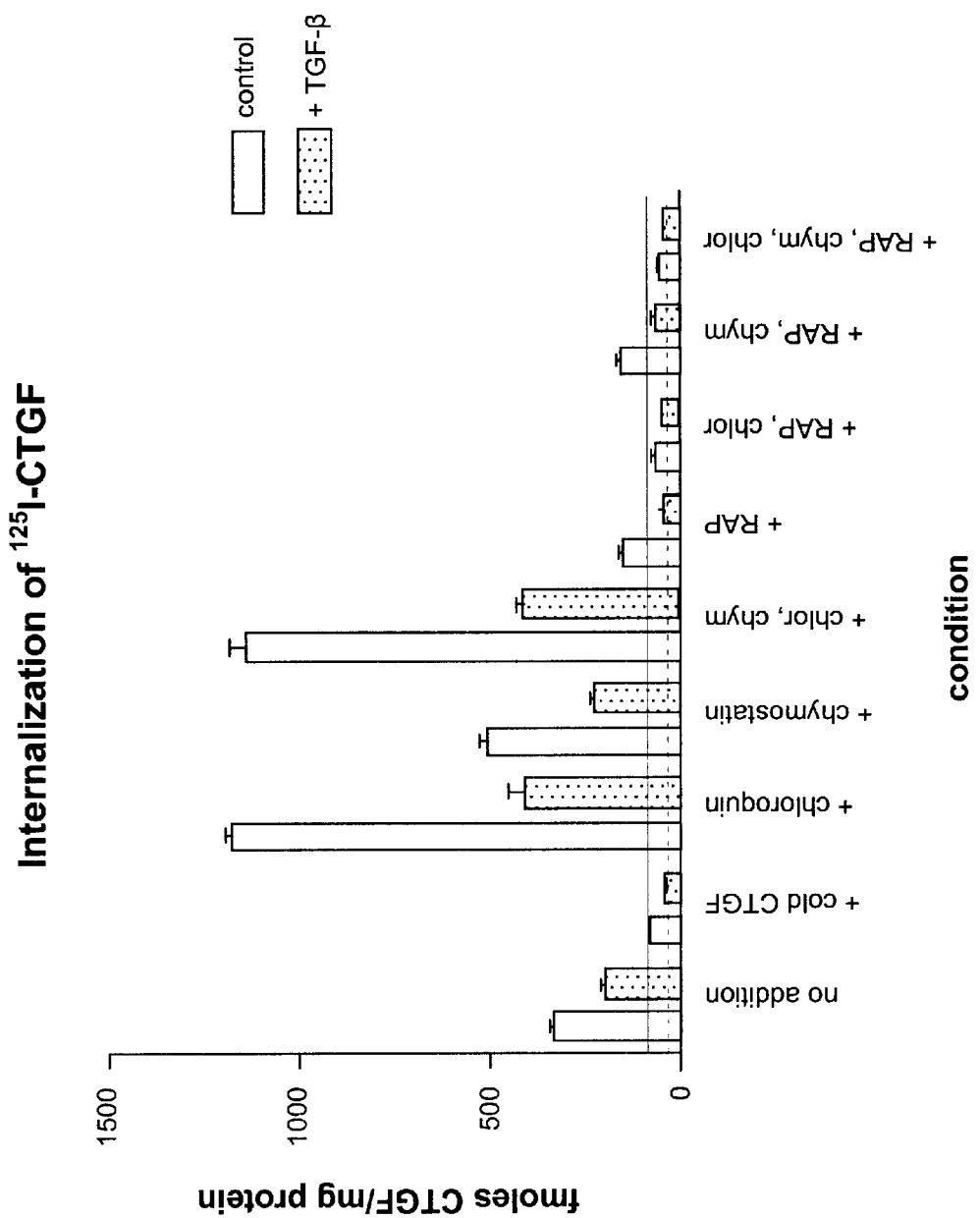
FIGS. 20A and 20B set forth data relating to internalization and degradation of CTGF by MG63 cells treated with TGF-β for 48 hours.
Figure 20B:
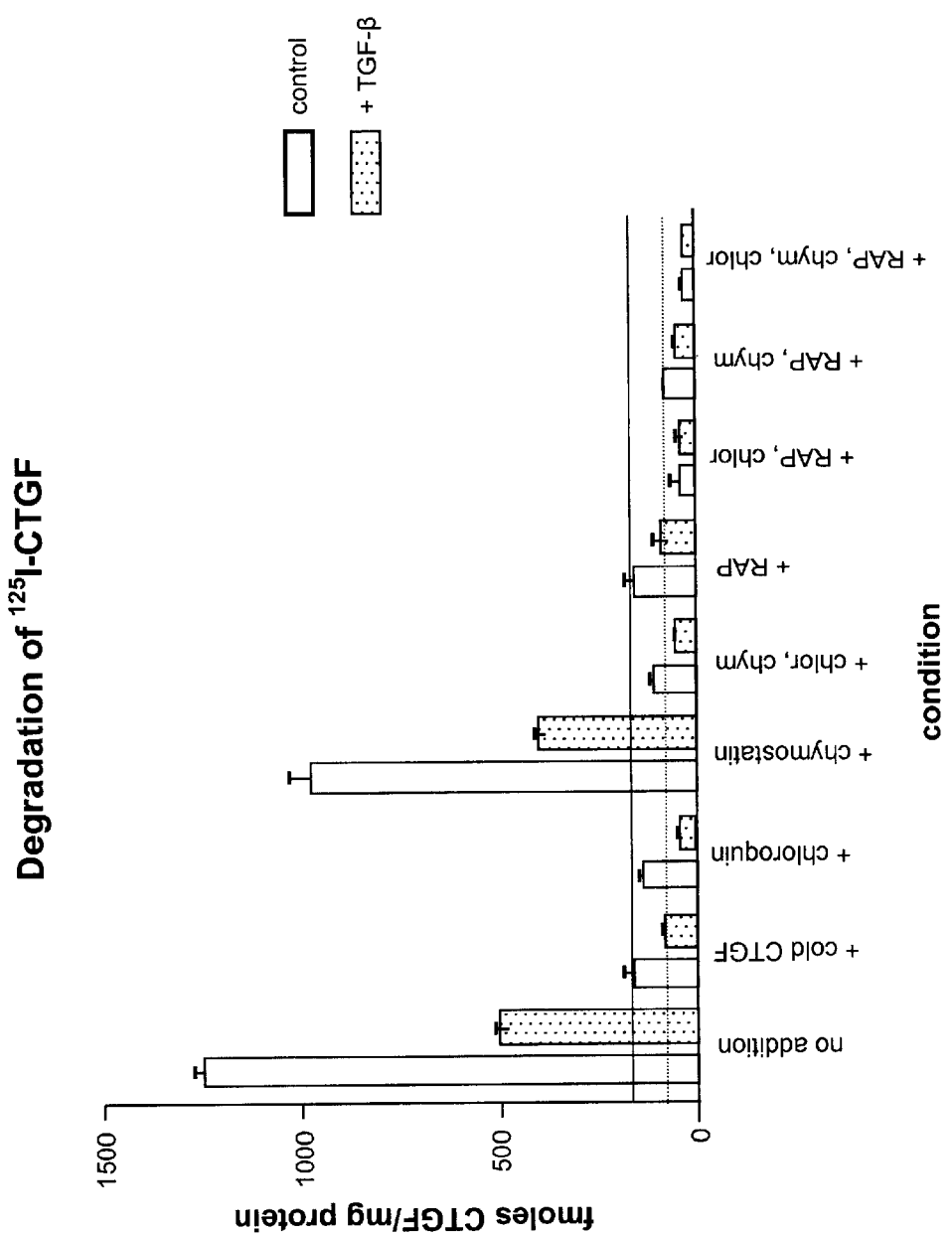

MG63 cells were plated and treated with TGF-β for 24 or 48 hours as in the previous experiment. Cells were rinsed twice with binding buffer and incubated with 0.2 nM $^{125}$I-rhCTGF with the appropriate additives, for two hours at 37° C. The results at 48 hours post-TGF-β exposure are shown in FIGS. 20A and 20B. In both graphs, the solid line was drawn to show the amount of $^{125}$I-rhCTGF determined when cold CTGF was added to quench radiolabel binding for control cultures; the hatched line was drawn to show the level of $^{125}$I-rhCTGF measured when the cold rhCTGF was added in TGF-β treated cultures. The specific amount of $^{125}$I-CTGF having undergone internalization and/or degradation was determined for each condition, as expressed as fmoles internalized and/or degraded minus fmoles internalized/degraded in the presence of excess cold CTGF.

During the two hour incubation period, approximately 260 fmoles CTGF/mg cell protein were specifically internalized (results calculated by subtraction of value at addition of cold from value at no addition) by control cells, while about 150 fmoles were internalized by TGF-β treated cells. In all samples with additives, except for chymostatin only treated cells, addition of RAP or chloroquin in all combinations reduced $^{125}$I-CTGF degradation to levels observed when cold CTGF was added (both control and TGF-β treated). About 1000 fmoles/mg cell protein were degraded by control cells, compared to 400 fmoles degraded in the TGF-β treated cells. The data indicated that in chloroquin treated samples, about 1000 fmoles and 400 fmoles remained as internalized rhCTGF in control and TGF-β treated cultures, respectively. Chloroquin raises the pH of the endosome, inhibiting dissociation of the ligands from their receptors; the end result being a reduction of ligand degradation. The effect of chloroquin on the integrity of the rhCTGF molecule was unclear.

In the presence of chloroquin, CTGF degradation products were not secreted into the medium. Chymostatin had no appreciable affect on degradation or internalization, suggesting that this protease inhibitor was not effective at increasing the stability of extracellular CTGF. The inclusion of quenching levels of RAP in the binding medium reduced the measured values of degraded/internalized $^{125}$I-CTGF to background levels in both cultures, demonstrating a role for LRP in the internalization and degradation assays. TGF-β was shown to reduce the total amount of CTGF internalized and subsequently degraded. Similar results were obtained in the 24 hour-treated cultures.

Example 17

TGF-β Impairment of Internalization Activity of CTGF Receptor

Figure 21:
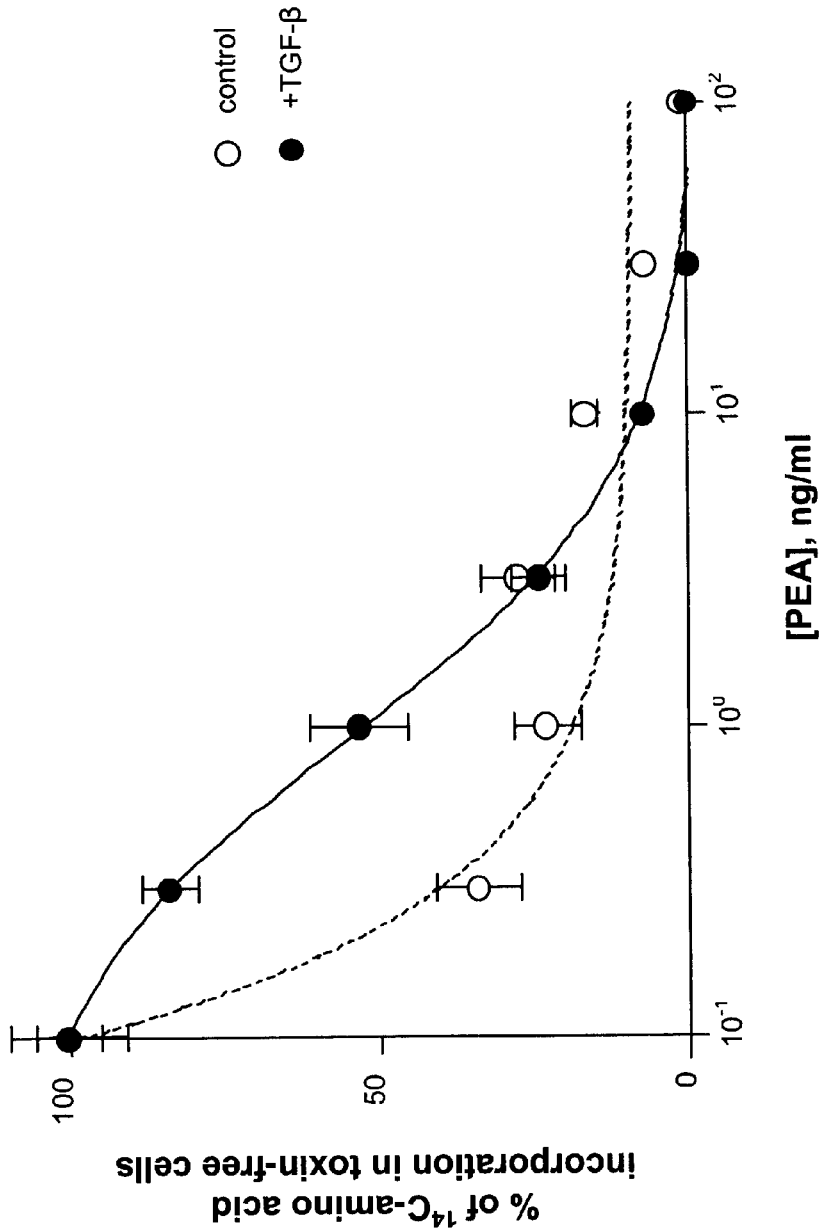
FIG. 21 sets forth data relating to protein synthesis in MG63 cells treated with Pseudomonas exotoxin A (PEA).

Pseudomonas exotoxin A (PEA) is a ligand for LRP, and following internalization is degraded in lysosomes. One of the degradation products contains PEA domain III, which promotes ADP-ribosylation of elongation factor-2, inhibiting protein synthesis. Protein synthesis in the presence of various concentrations of PEA was used to measure the internalization activity of LRP. To test whether TGF-β altered LRP activity for PEA internalization, MG63 cells were treated with 20 ng/ml TGF-β for 48 hours, then treated with various concentrations of PEA. After 2 hours, protein synthesis was monitored with an overnight pulse of $^{14}$C-amino acids. The cell layers were extracted with 10% trichloroacetic acid and counted. The results are shown in FIG. 21. The cells treated with TGF- appeared to be about 3-fold less sensitive to PEA than the control cells. These results agreed with previous observations that internalization and degradation of CTGF by CTGF receptor (LRP) were approximately 3-fold lower in TGF- treated cells.

Example 18

Expression of CTGF and CTGF Receptor (LRP) were Coincident

A human CTGF cDNA fragment and a human LRP cDNA fragment were radiolabeled by random priming with Rediprime II kit, by following the manufacturer's instructions (Amersham) and -[$^{32}$P]-dCTP (Amersham). A multi-tissue polyA+ RNA dot blot (multi-tissue expression array, MTE, Clontech Laboratories) and a multi-tissue adult human polyA+ Northern blot (multi-tissue Northern, MTN, Clontech Labotatories) were hybridized separately with the radiolabeled probes, using standard procedures known in the art. LRP mRNA was detected in all tissues and cells examined except the leukemia and lymphoma cell lines. CTGF mRNA was detected in all tissues and cells examine except in peripheral blood leukocytes, the leukemia, and the lymphoma cells lines. CTGF was highly expressed in heart, spleen, kidney, liver, placenta, lung and skeletal muscle. LRP (CTGF receptor) was expressed most strongly in heart, liver, and placenta, but was also expressed in brain, skeletal muscle, kidney, small intestine, lung, and peripheral blood leukocytes. Thus, LRP (CTGF receptor) and CTGF were expressed coincidently in all tissues examined, except for peripheral blood leukocytes.

Example 19

LRP as a Mediator of CTGF Biology

To determine whether LRP was involved in the mediation of a CTGF signaling event, experiments were conducted to study the effect of anti-LRP antibodies on CTGF production and accumulation. MG63 cells were plated at 2.5×10$^4$ cells/cm$^2$ in 24 well plates in MEM with 10% FBS. The following day, the medium was changed to MEM with 0.5% FBS. Additionally, half of the wells were supplemented with 20 ng/ml TGF-β2. Some of the cells also received either anti-LRP antibodies (American Diagnostic) (3 ug/ml 3402 and 1 ug/ml 3501) or RAP (10 nM). At 15, 23, and 47 hours after exposure to these additives, medium and cell layers were harvested.

Figure 22:
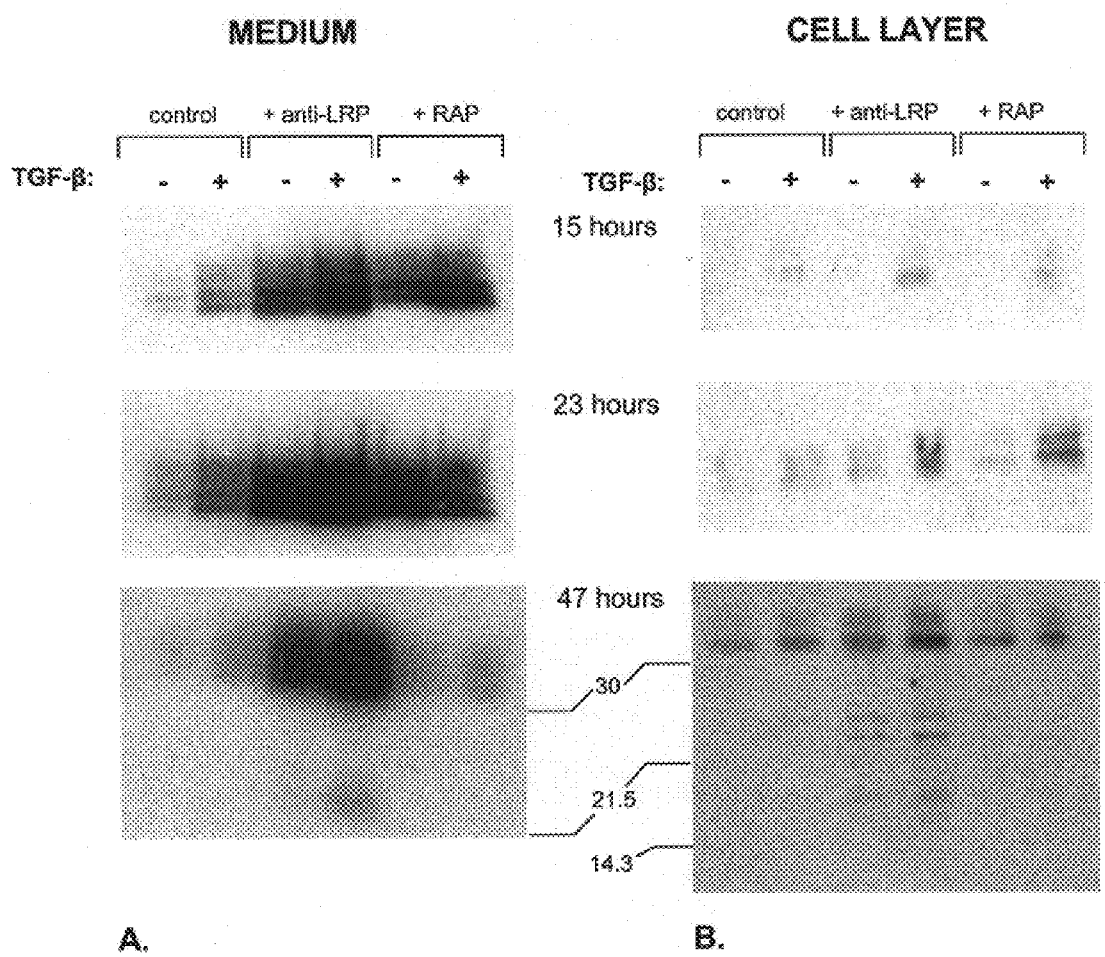
FIGS. 22A and 22B set forth data relating to effects of antibodies on TGF-β-induced CTGF production and accumulation.
Figure 23A:
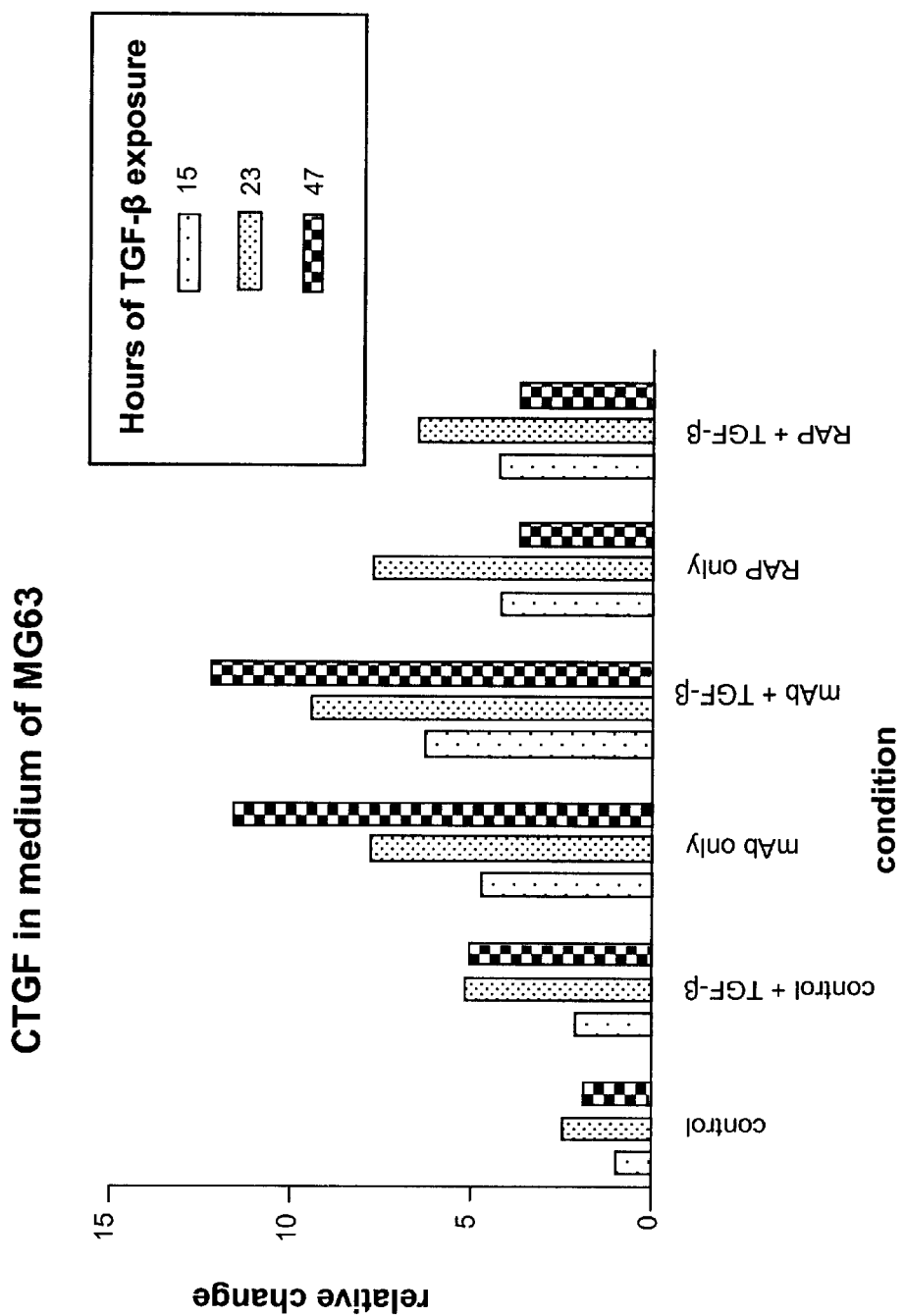
FIGS. 23A and 23B set forth data relating to the denisitometric analysis of the images in FIGS. 22A and 22B.
Figure 23B:
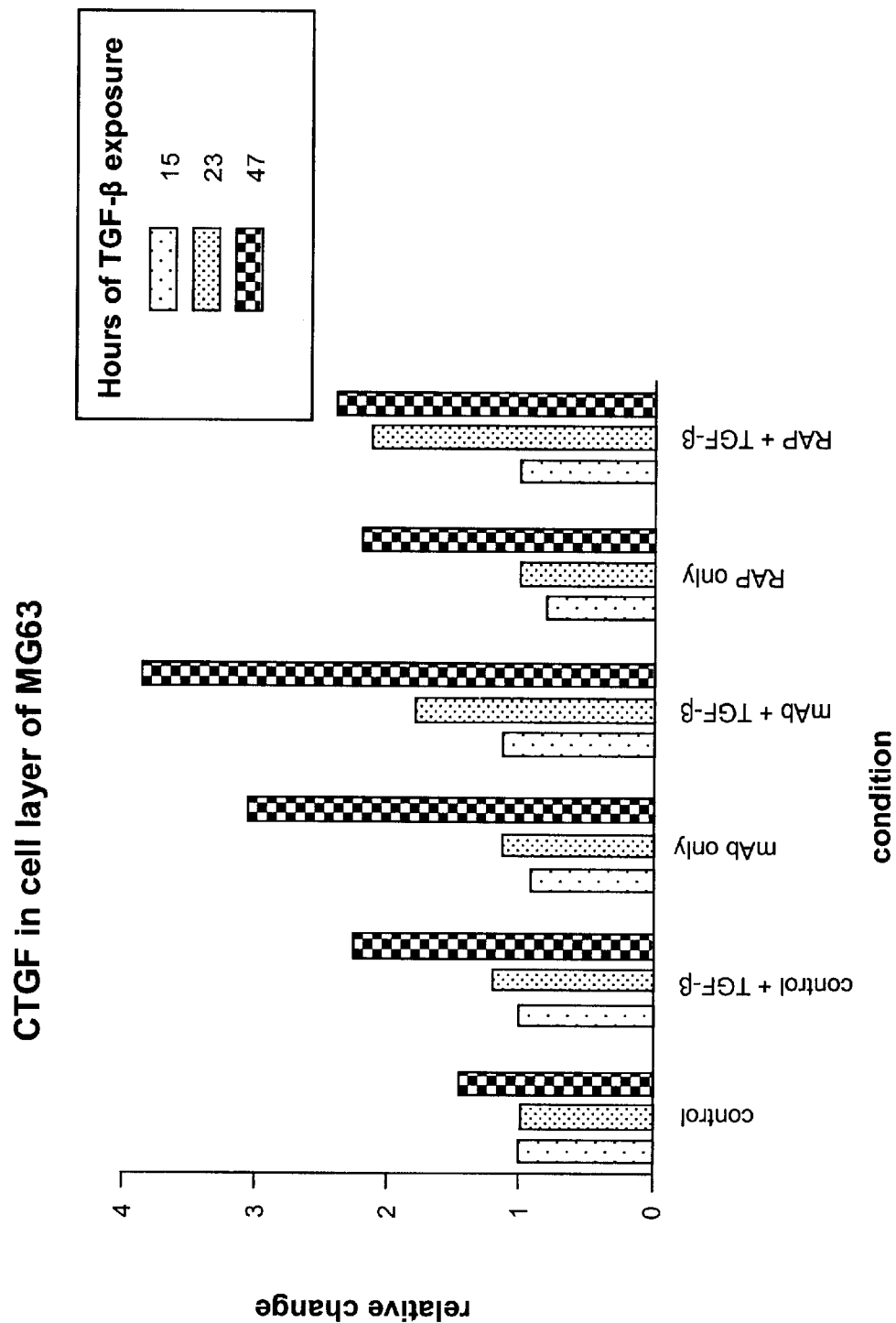

The harvested media was then incubated with heparin-SEPHAROSE for 4 hours. The beads were washed twice with RIPA buffer and the bound fraction was eluted with SDS-PAGE sample buffer. The cell layer was washed twice with PBS, then extracted for 15 min at 4° C. with RIPA buffer. The cell layer was collected by scraping, and centrifuged to remove the insoluble material. The soluble fraction was used for SDS-PAGE analysis. Both medium and cell layer samples were run non-reduced on 12% SDS-PAGE, then blotted to nitrocellulose. The nitrocellulose membranes were incubated with a rabbit polyclonal antibody made against rhCTGF (using procedures well known in the art), the data of which is shown in FIGS. 22A and 22B. Film images were scanned and analyzed by AlphaEase software and shown in FIGS. 23A and 23B. The densitometric analysis of FIGS. 22A and 22B is set forth in FIGS. 23A and 23B.

At all time points it was observed that anti-LRP antibody addition substantially increased the amount of CTGF in the medium, with at least a 6-fold increase in CTGF levels over that observed in each control culture at the respective time point. Only a slight difference was detected between TGF-β treated or untreated conditions in all of the antibody cultures, suggesting that the LRP-mediated turnover of CTGF was as important for accumulation in the medium as was the increase in CTGF protein synthesis. RAP treated cultures showed an increase in CTGF medium concentration at 15 and 23 hours, but by 47 hours the CTGF levels had returned to basal levels. Thus, antibody treatment modified LRP so that internalization was not occurring, or regeneration of the CTGF binding site did not occur during the period of treatment. The results observed in the cell layer were similar. Antibody treatment increased the basal level of CTGF over two fold in control cells at 47 hours. The TGF-β treated sample increased similarly when anti-LRP was present. RAP treated samples showed slightly increased levels of CTGF.

The foregoing experiment demonstrated that antibodies that block (neutralize) binding of CTGF to CTGF receptor (LRP) increased the accumulation and concentration of CTGF in medium and cell layer by at least six-fold.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims. All references cited herein are incorporated by reference herein in their entirety.

What is claimed is:

1. A method for identifying an agent that modulates the activity of a CTGF receptor wherein the CTGF receptor is the α2-macroglobulin receptor, the method comprising:
   (a) combining a candidate agent with CTGF polypeptide and the CTGF receptor;
   (b) detecting the level of CTGF receptor activity in the sample; and
   (c) comparing the level of CTGF receptor activity in the sample to a standard level of CTGF receptor activity.

2. The method of claim 1, wherein the activity of the CTGF receptor is binding to the CTGF polypeptide.

3. The method of claim 1, wherein the contacting is in vivo.

4. The method of claim 1, wherein the contacting is in vitro.

5. The method of claim 4, wherein the contacting is in cell culture.

6. The method of claim 5, wherein the activity of the CTGF receptor is internalization of the CTGF polypeptide.

7. The method of claim 4, wherein detecting comprises detection of degradation of the CTGF polypeptide.

* * * * *

SEQUENCE LISTING

<160> NUMBER OF SEQ ID NOS: 17

<210> SEQ ID NO 1
<211> LENGTH: 17
<212> TYPE: PRT
<213> ORGANISM: Mus musculus

<400> SEQUENCE: 1

Ala Ala Leu Ser Gly Ala Asn Val Leu Thr Leu Ile Glu Lys Asp Ile
1               5                   10                  15

Arg

<210> SEQ ID NO 2
<211> LENGTH: 19
<212> TYPE: PRT
<213> ORGANISM: Mus musculus

<400> SEQUENCE: 2

Asn Ala Val Val Gln Gly Leu Glu Gln Pro His Gly Leu Val Val His
1               5                   10                  15

Pro Leu Arg

<210> SEQ ID NO 3
<211> LENGTH: 10
<212> TYPE: PRT
<213> ORGANISM: Mus musculus

<400> SEQUENCE: 3

Ser Glu Arg Pro Pro Ile Phe Glu Ile Arg
1               5                   10

<210> SEQ ID NO 4
<211> LENGTH: 16
<212> TYPE: PRT
<213> ORGANISM: Mus musculus

<400> SEQUENCE: 4

Thr Val Leu Trp Pro Asn Gly Leu Ser Leu Asp Ile Pro Ala Gly Arg
1               5                   10                  15

<210> SEQ ID NO 5
<211> LENGTH: 12
<212> TYPE: PRT
<213> ORGANISM: Mus musculus

<400> SEQUENCE: 5

Thr Thr Leu Leu Ala Gly Asp Ile Glu His Pro Arg
1               5                   10

<210> SEQ ID NO 6
<211> LENGTH: 12
<212> TYPE: PRT
<213> ORGANISM: Mus musculus

<400> SEQUENCE: 6

Tyr Val Val Ile Ser Gln Gly Leu Asp Lys Pro Arg
1               5                   10

<210> SEQ ID NO 7
<211> LENGTH: 15
<212> TYPE: PRT
<213> ORGANISM: Mus musculus

```
<400> SEQUENCE: 7

Asp Gly Ile Leu Phe Trp Thr Asp Trp Asp Ala Ser Leu Pro Arg
1               5                   10                  15

<210> SEQ ID NO 8
<211> LENGTH: 17
<212> TYPE: PRT
<213> ORGANISM: Mus musculus

<400> SEQUENCE: 8

Gly Trp Asp Thr Leu Tyr Trp Thr Ser Tyr Thr Thr Ser Thr Ile Thr
1               5                   10                  15

Arg

<210> SEQ ID NO 9
<211> LENGTH: 21
<212> TYPE: PRT
<213> ORGANISM: Mus musculus

<400> SEQUENCE: 9

Ile Phe Phe Ser Asp Ile His Phe Gly Asn Ile Gln Gln Ile Asn Asp
1               5                   10                  15

Asp Gly Ser Gly Arg
            20

<210> SEQ ID NO 10
<211> LENGTH: 7
<212> TYPE: PRT
<213> ORGANISM: Mus musculus

<400> SEQUENCE: 10

Ile Leu Trp Ile Asp Ala Arg
1               5

<210> SEQ ID NO 11
<211> LENGTH: 15
<212> TYPE: PRT
<213> ORGANISM: Mus musculus

<400> SEQUENCE: 11

Ile Thr Trp Pro Asn Gly Leu Thr Val Asp Tyr Val Thr Glu Arg
1               5                   10                  15

<210> SEQ ID NO 12
<211> LENGTH: 19
<212> TYPE: PRT
<213> ORGANISM: Mus musculus

<400> SEQUENCE: 12

Asn Ala Val Val Gln Gly Leu Glu Gln Pro His Gly Leu Val Val His
1               5                   10                  15

Pro Leu Arg

<210> SEQ ID NO 13
<211> LENGTH: 10
<212> TYPE: PRT
<213> ORGANISM: Mus musculus

<400> SEQUENCE: 13

Ser Glu Arg Pro Pro Ile Phe Glu Ile Arg
1               5                   10
```

```
<210> SEQ ID NO 14
<211> LENGTH: 12
<212> TYPE: PRT
<213> ORGANISM: Mus musculus

<400> SEQUENCE: 14

Thr Thr Leu Leu Ala Gly Asp Ile Glu His Pro Arg
1               5                   10

<210> SEQ ID NO 15
<211> LENGTH: 16
<212> TYPE: PRT
<213> ORGANISM: Mus musculus

<400> SEQUENCE: 15

Thr Val Leu Trp Pro Asn Gly Leu Ser Leu Asp Ile Pro Ala Gly Arg
1               5                   10                  15

<210> SEQ ID NO 16
<211> LENGTH: 33
<212> TYPE: DNA
<213> ORGANISM: Homo sapiens

<400> SEQUENCE: 16
gctccgcccg cagtgggatc catgaccgcc gcc                              33

<210> SEQ ID NO 17
<211> LENGTH: 30
<212> TYPE: DNA
<213> ORGANISM: Homo sapiens

<400> SEQUENCE: 17
ggatccggat cctcatgcca tgtctccgta                                  30
```